US007718628B2

(12) United States Patent
Dobie et al.

(10) Patent No.: US 7,718,628 B2

(45) **Date of Patent: *May 18, 2010**

(54) ANTISENSE MODULATION OF KINESIN-LIKE 1 EXPRESSION

(75) Inventors: Kenneth W. Dobie, Del Mar, CA (US); Erich Koller, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/618,167

(22) Filed: Dec. 29, 2006

(65) Prior Publication Data

US 2008/0009456 A1 Jan. 10, 2008

Related U.S. Application Data

(63) Continuation of application No. 10/714,796, filed on Nov. 17, 2003, now Pat. No. 7,199,107, which is a continuation-in-part of application No. 10/156,603, filed on May 23, 2002, now Pat. No. 7,163,927.

(51) Int. Cl.

| | |
|---|---|
| ***C07H 21/02*** | (2006.01) |
| ***C07H 21/04*** | (2006.01) |
| ***A61K 31/70*** | (2006.01) |
| ***C12N 5/00*** | (2006.01) |
| *C12Q 1/68* | (2006.01) |

(52) U.S. Cl. ............................ 514/44; 436/6; 436/375; 436/377; 536/23.1; 536/24.1; 536/24.5

(58) Field of Classification Search ....................... None
See application file for complete search history.

(56) References Cited

U.S. PATENT DOCUMENTS

| | | | |
|---|---|---|---|
| 5,801,154 | A | 9/1998 | Baracchini et al. |
| 6,468,796 | B1 | 10/2002 | Watt |
| 6,472,521 | B1 | 10/2002 | Uhlmann et al. |
| 6,582,908 | B2 | 6/2003 | Fodor et al. |
| 7,163,927 | B2 | 1/2007 | Dobie et al. |
| 2001/0053519 | A1 | 12/2001 | Fodor et al. |
| 2002/0165240 | A1 | 11/2002 | Kimball et al. |
| 2003/0228597 | A1 | 12/2003 | Cowsert et al. |
| 2004/0009156 | A1 | 1/2004 | Reinhard et al. |

FOREIGN PATENT DOCUMENTS

| | | |
|---|---|---|
| WO | WO 93/13121 | 7/1993 |
| WO | WO 01/07602 | 2/2001 |
| WO | WO 03/030832 | 4/2003 |
| WO | WO 03/099224 | 12/2003 |

OTHER PUBLICATIONS

Agrawal, S. et al., "Antisense therapeutics: is it as simple as complementary base recognition" *Molecular Med. Today* (2000) 6:72-81.

Blangy et al., "Phosphorylation by p34cdc2 regulates spindle association of human Eg5, a kinesin-related motor essential for bipolar spindle formation in vivo" *Cell* (1995) 83:1159-1169.

Branch, A.D. et al., "A good antisense molecule is hard to find" *TIBS* (1998) 23:45-50.

Ferhat et al., "Expression of the mitotic motor protein Eg5 in postmitotic neurons: implications for neuronal development" *J. Neurosci.* (1998) 18:7822-7835.

Hansen et al., "Activation of Hex and mEg5 by retroviral insertion may contribute to mouse B-cell leukemia" *Oncogene* (1999) 18:6531-6539.

Jen, K.Y. et al., "Suppression of gene expression by targeted disruption of messenger RNA: available options and current strategies" *Stem Cells* (2000) 18:307-319.

Kaiser et al., "All-trans-retinoic acid-mediated growth inhibition involves inhibition of human kinesin-related protein HsEg5" *J. Biol. Chem.* (1999) 274:18925-18931.

Kapoor et al., "Probing spindle assembly mechanisms with monastrol, a small molecule inhibitor of the mitotic kinesin, Eg5" *J. Cell Biol.* (2000) 150:975-988.

Mayer et al. "Small molecule inhibitor of mitotic spindle bipolarity identified in a phenotype-based screen" *Science* (1999) 286:971-974.

Miki et al., "All kinesin superfamily protein, KIF, genes in mouse and human" *Proc. Natl. Acad. Sci. U. S. A.* (2001) 98:7004-7011.

Weil, D. et al., "Targeting the kinesin Eg5 to monitor siRNA transfection in mammalian cells" *Short Technical Reports, BioTechniques* (2002) 33:1244-1248.

Whitehead et al., "Expanding the role of HsEg5 within the mitotic and post-mitotic phases of the cell cycle" *J. Cell Sci.* (1998) 111:2551-2561.

Whitehead et al., "The spindle kinesin-like protein HsEg5 is an autoantigen in systemic lupus erythematosus" *Arthritis Rheum.* (1996) 39:1635-1642.

Elbashir, et al. (2002), "Analysis of gene function in somatic mammalian cells using small interfering RNAs" Methods: A companion to methods in enzymology 26: 199-213.

Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

New England BioLabs, Inc. Catalogue (1998): 121, 284.

Reynolds et al., Rational siRNA design for Rna interference, Mar. 2004, Nature Biotechnology, vol. 22, pp. 326-330.

Crooke, S, "Basic Principles of Antisense Therapeutics," Antisense Research and Applications, Chapter 1, Springer-Verlag Press, Berlin, Heidelberg, New York, p. 3, Jun. 1998.

(Continued)

*Primary Examiner*—Sean R McGarry
(74) *Attorney, Agent, or Firm*—Knobbe Martens Olson & Bear LLP

(57) ABSTRACT

Antisense compounds, compositions and methods are provided for modulating the expression of kinesin-like 1. The compositions comprise antisense compounds, particularly antisense oligonucleotides, targeted to nucleic acids encoding kinesin-like 1. Methods of using these compounds for modulation of kinesin-like 1 expression and for treatment of diseases associated with expression of kinesin-like 1 are provided.

19 Claims, No Drawings

OTHER PUBLICATIONS

Sanghvi, Y. Antisense Research & Applications, CH 15, pp. 274-285, CRC Press, 1993.

Supplementary European Search Report from EP 04 81 1304 dated Jul. 13, 2007.

Supplementary European Search Report from EP 03 73 4171 dated Jul. 12, 2007.

International Search Report from PCT/US04/38545 dated Dec. 27, 2005.

International Search Report from PCT/US03/16467 dated Apr. 22, 2004.

ANTISENSE MODULATION OF KINESIN-LIKE 1 EXPRESSION

CROSS-REFERENCE TO RELATED APPLICATIONS

This application is a continuation of U.S. patent application Ser. No. 10/714,796, filed Nov. 17, 2003, which is a continuation-in-part of U.S. patent application Ser. No. 10/156,603, filed May 23, 2002. This is application is related to PCT Publication No. WO 2005/049630, filed Nov. 17, 2004. The contents of each application are incorporated herein in their entirety.

INCORPORATION OF SEQUENCE LISTING

The present application is being filed along with a Sequence Listing in electronic format. The Sequence Listing is provided as a file entitled HTS0016USC1SEQ.txt, created Dec. 28, 2006, which is 148 Kb in size. The information in the electronic format of the sequence listing is incorporated herein by reference in its entirety.

FIELD OF THE INVENTION

The present invention provides compositions and methods for modulating the expression of kinesin-like 1. In particular, this invention relates to compounds, particularly oligonucleotides, specifically hybridizable with nucleic acids encoding kinesin-like 1. Such compounds have been shown to modulate the expression of kinesin-like 1.

BACKGROUND OF THE INVENTION

The intracellular transport of proteins, lipids, and mRNA to specific locations within the cell, as well as the proper alignment and separation of chromosomes in dividing cells, is essential to the functioning of the cell. The superfamily of proteins called kinesins (KIF), along with the myosins and dyneins, function as molecular engines to bind and transport vesicles and organelles along microtubules with energy supplied by ATP. KIFs have been identified in many species ranging from yeast to humans. The amino acid sequences which comprise the motor domain are highly conserved among eukaryotic phyla, while the region outside of the motor domain serves to bind to the cargo and varies in amino acid sequence among KIFs. The movement of a kinesin along a microtubule can occur in either the plus or minus direction, but any given kinesin can only travel in one direction, an action that is mediated by the polarity of the motor and the microtubule. The KIFs have been grouped into three major types depending on the position of the motor domain: the amino-terminal domain, the middle motor domain, and the carboxyl-terminal domain, referred to respectively as N-kinesin, M-kinesin, and C-kinesins. These are further classified into 14 classes based on a phylogenetic analysis of the 45 known human and mouse kinesin genes (Miki et al., *Proc. Natl. Acad. Sci. U.S.A.,* 2001, 98, 7004-7011).

One such kinesin, kinesin-like 1, a member of the N-2 (also called bimC) family of kinesins and is involved in separating the chromosomes by directing their movement along microtubules in the bipolar spindle. During mitosis, the microtubule bipolar spindle functions to distribute the duplicated chromosomes equally to daughter cells. Kinesin-like 1 is first phosphorylated by the kinase $p34^{cdc2}$ and is essential for centrosome separation and assembly of bipolar spindles at prophase (Blangy et al., *Cell,* 1995, 83, 1159-1169). In rodent neurons, kinesin-like 1 is expressed well past their terminal mitotic division, and has been implicated in regulating microtubule behaviors within the developing axons and dendrites (Ferhat et al., *J. Neurosci.,* 1998, 18, 7822-7835). The gene encoding human kinesin-like 1 (also called KNSL1, EgS, HsEg5, HKSP, KIF11, thyroid interacting protein 5, and TRIP5) was cloned in 1995 (Blangy et al., *Cell,* 1995, 83, 1159-1169).

Inhibition of kinesin-like 1 has been suggested as a target for arresting cellular proliferation in cancer because of the central role kinesin-like 1 holds in mitosis. Expression of kinesin-like 1 may also contribute to other disease states. A contribution of kinesin-like 1 to B-cell leukemia has been demonstrated in mice as a result of upregulated expression of kinesin-like 1 following a retroviral insertion mutation in the proximity of the kinesin-like 1 gene (Hansen and Justice, *Oncogene,* 1999, 18, 6531-6539). Autoantibodies to a set of proteins in the mitotic spindle assembly have been detected in human sera and these autoantibodies have been associated with autoimmune diseases including carpal tunnel syndrome, Raynaud's phenomenon, systemic sclerosis, Sjorgren's syndrome, rheumatoid arthritis, polymyositis, and polyarteritis. One of these autoantigens is kinesin-like 1 and has been identified in systemic lupus erythematosus (Whitehead et al., *Arthritis Rheum.,* 1996, 39, 1635-1642).

Currently, there are no known therapeutic agents which effectively inhibit the synthesis of kinesin-like 1. The use of antibodies to kinesin-like 1 has been reported several times in the art as a method to examine the participation of kinesin-like 1 during different stages of mitosis (Blangy et al., *Cell,* 1995, 83, 1159-1169.; Kapoor et al., *J. Cell Biol.,* 2000, 150, 975-988.; Whitehead and Rattner, *J. Cell Sci.,* 1998, 111, 2551-2561). For instance, in the presence of antibodies specific to kinesin-like 1, microtubule arrays responsible for pre- and post-mitotic centrosome movement never form, confirming the recurring role of kinesin-like 1 in establishing the microtubule arrays that form during cell division. This role may also encompass the ability of kinesin-like 1 to influence the distribution of other protein components associated with cell division (Whitehead and Rattner, *J. Cell Sci.,* 1998, 111, 2551-2561).

The small molecule monastrol has been used in vitro as a useful and specific tool to probe the involvement of kinesin-like 1 in the mitotic process (Kapoor et al., *J. Cell Biol.,* 2000, 150, 975-988). Like the anti-kinesin-like 1 antibodies, the small molecule monastrol produces a monoastral phenotype, as opposed to the bipolar spindle, and subsequently arrests mitosis. The formation of the monastral spindle is reversible when monastrol is washed away, and the mechanism of monastrol action is presumed to be inhibition of kinesin-like 1 (Mayer et al., *Science,* 1999, 286, 971-974).

Another small molecule, all-trans-retinoic acid (ATRA) is able to arrest growth in a number of different cell types such as melanoma, lymphoma, neuroblastoma, embryonic stem, and carcinoma cells by modulating gene expression. Kinesin-like 1 is one of these target genes and the expression of kinesin-like 1 in pancreatic carcinoma cell lines is inhibited by ATRA at the posttranscriptional level. These anti-proliferative effects arising from ATRA inhibition of kinesin-like 1 was further confirmed by the use of an antisense expression vector directed against kinesin-like 1 (Kaiser et al., *J. Biol. Chem.,* 1999, 274, 18925-18931).

U.S. Patent Application Publication No. 2002/0165240, published Nov. 7, 2002 (Kimball et al.), discloses methods for treating a condition via modulation of Eg5 protein activity comprising administering a small molecule Eg5 inhibitor.

There remains a long felt need for additional agents capable of effectively inhibiting kinesin-like 1 function.

Antisense technology is emerging as an effective means for reducing the expression of specific gene products and may therefore prove to be uniquely useful in a number of therapeutic, diagnostic, and research applications for the modulation of kinesin-like 1 expression. A small interfering RNA (siRNA) targeting the mRNA of the kinesin has been used to assay for the optimization of siRNA transfection, and was found to induce mitotic arrest. D. Weil et al., 2002, BioTechniques 33:1244-1248. U.S. Pat. No. 6,472,521, issued Oct. 29, 2002 (Uhlmann et al.), discloses and claims oligonucleotides for the inhibition of human Eg5 expression. PCT Publication WO 03/030832, published Apr. 17, 2003 (Reinhard et al.), discloses use of antisense oligonucleotides that target human kinesin genes for treating diseases involving aberrant cell proliferation. The kinesin gene may be human Eg5.

The present invention provides compositions and methods for modulating kinesin-like 1 expression.

SUMMARY OF THE INVENTION

The present invention is directed to antisense compounds, especially nucleic acid and nucleic acid-like oligomers, which are targeted to a nucleic acid encoding kinesin-like 1, and which modulate the expression of kinesin-like 1. Pharmaceutical and other compositions comprising the compounds of the invention are also provided. Further provided are methods of screening for modulators of kinesin-like 1 and methods of modulating the expression of kinesin-like 1 in cells, tissues or animals comprising contacting said cells, tissues or animals with one or more of the compounds or compositions of the invention. Methods of treating an animal, particularly a human, suspected of having or being prone to a disease or condition associated with expression of kinesin-like 1 are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs antisense compounds, preferably oligonucleotides and similar species for use in modulating the function or effect of nucleic acid molecules encoding kinesin-like 1. This is accomplished by providing oligonucleotides which specifically hybridize with one or more nucleic acid molecules encoding kinesin-like 1. As used herein, the terms “target nucleic acid” and “nucleic acid molecule encoding kinesin-like 1” have been used for convenience to encompass DNA encoding kinesin-like 1, RNA (including pre-mRNA and mRNA or portions thereof) transcribed from such DNA, and also cDNA derived from such RNA. The hybridization of a compound of this invention with its target nucleic acid is generally referred to as “antisense”. Consequently, the preferred mechanism believed to be included in the practice of some preferred embodiments of the invention is referred to herein as “antisense inhibition.” Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of kinesin-like 1. In the context of the present invention, “modulation” and “modulation of expression” mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, “hybridization” means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase “stringent hybridization conditions” or “stringent conditions” refers to conditions under which a compound of the invention will hybridize to its target sequence, but to a minimal number of other sequences. Stringent conditions are sequence-dependent and will be different in different circumstances and in the context of this invention, “stringent conditions” under which oligomeric compounds hybridize to a target sequence are determined by the nature and composition of the oligomeric compounds and the assays in which they are being investigated.

“Complementary,” as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, “specifically hybridizable” and “complementary” are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403-410; Zhang and Madden, *Genome Res.,* 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

B. Compounds of the Invention

According to the present invention, antisense compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell,* 1995, 81, 611-620).

Montgomery et al. have shown that the primary interference effects of dsRNA are posttranscriptional (Montgomery et al., *Proc. Natl. Acad. Sci. USA,* 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature,* 1998, 391, 806-811). Recently, it has been shown that it is, in fact, the single-stranded RNA oligomers of antisense polarity of the dsRNAs which are the potent inducers of RNAi (Tijsterman et al., *Science,* 2002, 295, 694-697).

The antisense compounds of the present invention also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to inhibit expression of kinesin-like 1 mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the antisense compounds of this invention, the present invention comprehends other families of antisense compounds as well, including but not limited to oligonucleotide analogs and mimetics such as those described herein.

The antisense compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the antisense compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the antisense compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that preferred antisense compounds may be represented by oligonucleotide sequences that comprise at least 8 consecutive nucleobases from an internal portion of the sequence of an illustrative preferred antisense compound, and may extend in either or both directions until the oligonucleotide contains about 8 to about 80 nucleobases.

One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes kinesin-like 1.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding kinesin-like 1, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). It is also understood that preferred antisense target segments may be represented by DNA or RNA sequences that comprise at least 8 consecutive nucleobases from an internal portion of the sequence of an illustrative preferred target segment, and may extend in either or both directions until the oligonucleotide contains about 8 to about 80 nucleobases. One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds may also be targeted to regions of the target nucleobase sequence (e.g., such as those disclosed in Examples below) comprising nucleobases 1-80, 81-160, 161-240, 241-320, 321-400, 401-480, . . . , etc, or any combination thereof.

D. Screening and Target Validation

In a further embodiment, the "preferred target segments" identified herein may be employed in a screen for additional compounds that modulate the expression of kinesin-like 1. "Modulators" are those compounds that decrease or increase the expression of a nucleic acid molecule encoding kinesin-like 1 and which comprise at least an 8-nucleobase portion which is complementary to a preferred target segment. The screening method comprises the steps of contacting a preferred target segment of a nucleic acid molecule encoding kinesin-like 1 with one or more candidate modulators, and selecting for one or more candidate modulators which decrease or increase the expression of a nucleic acid molecule encoding kinesin-like 1. Once it is shown that the candidate modulator or modulators are capable of modulating (e.g. either decreasing or increasing) the expression of a nucleic acid molecule encoding kinesin-like 1, the modulator may then be employed in further investigative studies of the function of kinesin-like 1, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature,* 1998, 391, 806-811; Timmons and Fire, *Nature* 1998, 395, 854; Timmons et al., *Gene,* 2001, 263, 103-112; Tabara et al., *Science,* 1998, 282, 430-431; Montgomery et al., *Proc. Natl. Acad. Sci. USA,* 1998, 95, 15502-15507; Tuschl et al., *Genes Dev.,* 1999, 13, 3191-3197; Elbashir et al., *Nature,* 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science,* 2002, 295, 694-697).

The antisense compounds of the present invention can also be applied in the areas of drug discovery and target validation. The present invention comprehends the use of the compounds and preferred target segments identified herein in drug discovery efforts to elucidate relationships that exist between kinesin-like 1 and a disease state, phenotype, or condition. These methods include detecting or modulating kinesin-like 1 comprising contacting a sample, tissue, cell, or organism with the compounds of the present invention, measuring the nucleic acid or protein level of kinesin-like 1 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The antisense compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.,* 2000, 480, 17-24; Celis, et al., *FEBS Lett.,* 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

The antisense compounds of the invention are useful for research and diagnostics, because these compounds hybridize to nucleic acids encoding kinesin-like 1. For example, oligonucleotides that are shown to hybridize with such efficiency and under such conditions as disclosed herein as to be effective kinesin-like 1 inhibitors will also be effective primers or probes under conditions favoring gene amplification or detection, respectively. These primers and probes are useful in methods requiring the specific detection of nucleic acid molecules encoding kinesin-like 1 and in the amplification of said nucleic acid molecules for detection or for use in further studies of kinesin-like 1. Hybridization of the antisense oligonucleotides, particularly the primers and probes, of the invention with a nucleic acid encoding kinesin-like 1 can be detected by means known in the art. Such means may include conjugation of an enzyme to the oligonucleotide, radiolabelling of the oligonucleotide or any other suitable detection means. Kits using such detection means for detecting the level of kinesin-like 1 in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of kinesin-like 1 is treated by administering antisense compounds in accordance with this invention. For example, in one non-limiting embodiment, the methods comprise the step of administering to the animal in need of treatment, a therapeutically effective amount of a kinesin-like 1 inhibitor. The kinesin-like 1 inhibitors of the present invention effectively inhibit the activity of the kinesin-like 1 protein or inhibit the expression of the kinesin-like 1 protein. In one embodiment, the activity or expression of kinesin-like 1 in an animal is inhibited by about 10%. Preferably, the activity or expression of kinesin-like 1 in an animal is inhibited by about 30%. More preferably, the activity or expression of kinesin-like 1 in an animal is inhibited by 50% or more. Thus, the oligomeric antisense compounds modulate expression of kinesin-like 1 mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of kinesin-like 1 may be measured in serum, adipose tissue, liver or any other body fluid, tissue or organ of the animal. Preferably, the cells contained within said fluids, tissues or organs being analyzed contain a nucleic acid molecule encoding kinesin-like 1 protein and/or the kinesin-like 1 protein itself.

The antisense compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriaminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred antisense compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—$N(CH_3)$—O—$CH_2$— [known as a methylene (methylimino) or MMI backbone], —$CH_2$—O—$N(CH_3)$—$CH_2$—, —$CH_2$—$N(CH_3)$—$N(CH_3)$—$CH_2$— and —O—$N(CH_3)$—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified antisense compounds may also contain one or more substituted sugar moieties. Preferred are antisense compounds, preferably antisense oligonucleotides, comprising one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$-O—$CH_2$-$N(CH_3)_2$, also described in examples hereinbelow.

Other preferred modifications include 2'-methoxy (2'-O—$CH_3$), 2'-aminopropoxy (2'-$OCH_2CH_2CH_2NH_2$), 2'-allyl (2'-$CH_2$—CH═$CH_2$), 2'-O-allyl (2'-O—$CH_2$—CH═$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3'terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene $(—CH_2—)_n$ group bridging the 2' oxygen atom and the 4' carbon atom wherein n is 1 or 2. LNAs and preparation thereof are described in WO 98/39352 and WO 99/14226.

Natural and Modified Nucleobases

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750, 692, which is commonly owned with the instant application and also herein incorporated by reference.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodo-benzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. Chimeric antisense oligonucleotides are thus a form of anti sense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2- methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl] -2-cyanoethyl-N,N-diisopropylphosphoramidite (MOE G amidite), 2'-O-(Aminooxyethyl) nucleoside amidites and 2'-O-(dimethylaminooxy-ethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P═O) oligonucleotides are synthesized on an automated DNA synthesizer (Applied Biosystems model 394) using standard phosphoramidite chemistry with oxidation by iodine.

Phosphorothioates (P═S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or U.S. Pat. No. 5,625,050, herein incorporated by reference.

Phosphoramidite oligonucleotides are prepared as described in U.S. Pat. No., 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand,.* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 μM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting Kinesin-Like 1

In accordance with the present invention, a series of nucleic acid duplexes comprising the antisense compounds of the present invention and their complements can be designed to target kinesin-like 1. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 238) and having a two-nucleobase overhang of deoxythymidine(dT) would have the following structure:

```
  cgagaggcggacgggaccgTT    Antisense Strand
  |||||||||||||||||||      (SEQ ID NO: 239)
TTgcucuccgccugcccuggc      Complement
                           (SEQ ID NO: 240)
```

In another embodiment, a duplex comprising an antisense strand having the same sequence CGAGAGGCGGACGGGACCG (SEQ ID NO: 238) may be prepared with blunt ends (no single stranded overhang) as shown:

```
cgagaggcggacgggaccg    Antisense Strand
|||||||||||||||||||    (SEQ ID NO: 238)
gcucuccgccugcccuggc    Complement
                       (SEQ ID NO: 241)
```

RNA strands of the duplex can be synthesized by methods disclosed herein or purchased from Dharmacon Research Inc., (Lafayette, Colo.). Once synthesized, the complementary strands are annealed. The single strands are aliquotted and diluted to a concentration of 50 μM. Once diluted, 30 μL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 μM. This solution can be stored frozen (−20° C.) and freeze-thawed up to 5 times.

Once prepared, the duplexed antisense compounds are evaluated for their ability to modulate kinesin-like 1 expression. When cells reach 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

T47D Cells:

The T47D breast adenocarcinoma cells were obtained from the American Type Culture Collection (ATCC) (Manassas, Va.). Cells were cultured in Gibco DMEM High glucose media supplemented with 10% FBS.

For cell cycle assays, cells are plated in 24-well plates at 170,000 cells per well.

MCF7:

The human breast carcinoma cell line MCF-7 was obtained from the American Type Culture Collection (Manassas, Va.). MCF-7 cells were routinely cultured in DMEM low glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For cell cycle assays, cells are plated in 24-well plates at 140,000 cells per well. HMEC:

The human mammary epithelial cell line HMEC was obtained from BioWhittacker (Clonetics). HMEC cells were routinely cultured in Mammary Epithelial Growth Medium, BioWhittacker (Clonetics). Cells were routinely passaged by trypsinization and dilution when they reached 70% confluence. Cells were seeded into 24-well plates (Nunc-Nuncolon cat. #143982) at a density of 60,000 cells/well for use in subsequent analyses. b.END cells:

The mouse brain endothelial cell line b.END was obtained from Dr. Werner Risau at the Max Plank Institute (Bad Nauheim, Germany). b.END cells were routinely cultured in DMEM supplemented with 10% fetal bovine serum (Gibco/Life Technologies, Gaithersburg, Md.). Cells were routinely passaged by trypsinization and dilution when they reached 90% confluence. Cells were seeded into 24-well plates (Falcon-Primaria #3047) at a density of 40,000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment With Antisense Compounds:

When cells reached 70% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. After 4-7 hours of treatment, the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Kinesin-Like 1 Expression

Antisense modulation of kinesin-like 1 expression can be assayed in a variety of ways known in the art. For example, kinesin-like 1 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of kinesin-like 1 can be quantitated in a variety of ways well known in the art, such as immunoprecipitation, Western blot analysis (immunoblotting), ELISA or fluorescence-activated cell sorting (FACS). Antibodies directed to kinesin-like 1 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., (*Current Protocols in Molecular Biology*, Volume 2, pp. 11.12.1-11.12.9, John Wiley & Sons, Inc., 1997). Preparation of monoclonal antibodies is taught in, for example, Ausubel, F. M. et al., (*Current Protocols in Molecular Biology*, Volume 2, pp. 11.4.1-11.11.5, John Wiley & Sons, Inc., 1997).

Immunoprecipitation methods are standard in the art and can be found at, for example, Ausubel, F. M. et al., (*Current Protocols in Molecular Biology*, Volume 2, pp. 10.16.1-10.16.11, John Wiley & Sons, Inc., 1998). Western blot (immunoblot) analysis is standard in the art and can be found at, for example, Ausubel, F. M. et al., (*Current Protocols in Molecular Biology*, Volume 2, pp. 10.8.1-10.8.21, John Wiley & Sons, Inc., 1997). Enzyme-linked immunosorbent assays (ELISA) are standard in the art and can be found at, for example, Ausubel, F. M. et al., (*Current Protocols in Molecular Biology*, Volume 2, pp. 11.2.1-11.2.22, John Wiley & Sons, Inc., 1991).

Example 11

Poly(A)+mRNA Isolation

Poly(A)+mRNA was isolated according to Miura et al., (*Clin. Chem.*, 1996, 42, 1758-1764). Other methods for poly (A)+mRNA isolation are taught in, for example, Ausubel, F. M. et al., (*Current Protocols in Molecular Biology*, Volume 1, pp. 4.5.1-4.5.3, John Wiley & Sons, Inc., 1993). Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY 96™ plate and incubated for 15 minutes and the vacuum was again applied for 1 minute. An additional 500 μL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 170 μL water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Kinesin-Like 1 mRNA Levels

Quantitation of kinesin-like 1 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5× PCR buffer (—MgCl2), 6.6 mM MgCl2, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution. The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 480 nm and emission at 520 nm.

Probes and primers to human kinesin-like 1 were designed to hybridize to a human kinesin-like 1 sequence, using published sequence information (GenBank accession number NM_004523.1, incorporated herein as SEQ ID NO:3 and 4). For human kinesin-like 1 the PCR primers were:

forward primer: GTGGTGAGATGCAGACCATTTAAT (SEQ ID NO: 5)

reverse primer: CTTTTCGTACAGGATCACATTCTACTATTG (SEQ ID NO: 6) and the PCR probe was: FAM-TGGCAGAGCGGAAAGCTAGCGC-TAMRA (SEQ ID NO: 7) where FAM is the fluorescent dye and TAMRA is the quencher dye. For human GAPDH the PCR primers were:

forward primer: GAAGGTGAAGGTCGGAGTC(SEQ ID NO:8)

reverse primer: GAAGATGGTGATGGGATTTC (SEQ ID NO:9) and the PCR probe was: 5'JOE-CAAGCTTCCCGTTCTCAGCC-TAMRA 3' (SEQ ID NO: 10) where JOE is the fluorescent reporter dye and TAMRA is the quencher dye.

Example 14

Northern Blot Analysis of Kinesin-Like 1 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human kinesin-like 1, a human kinesin-like 1 specific probe was prepared by PCR using the forward primer GTGGTGAGATGCAGACCATTTAAT (SEQ ID NO: 5) and the reverse primer CTTTTCGTACAGGATCACATTCTACTATTG (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Kinesin-Like 1 Expression by Chimeric Phosphorothioate Oligonucleotides Having 2'-MOE Wings and a Deoxy Gap In accordance with the present invention, a series of oligonucleotides were designed to target different regions of the human kinesin-like 1 RNA, using published sequences (GenBank accession number NM_004523.1, incorporated herein as SEQ ID NO: 3 and 4). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethoxy (2'-MOE) nucleotides. The internucleoside (backbone) linkages are phosphorothioate (P═S) throughout the oligonucleotide. All cytidine residues are 5-methylcytidines. The compounds were analyzed for their effect on human kinesin-like 1 mRNA levels by quantitative real-time PCR as described in other examples herein. Data are averages from two experiments in which T-24 cells were treated with the antisense oligonucleotides of the present invention. If present, "N.D." indicates "no data".

TABLE 1

Inhibition of human kinesin-like 1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 183876 | Coding | 3 | 2284 | tgttgactatatccttagat | 44 | 11 |
| 183877 | Coding | 3 | 1838 | tctgctgctaatgattgttc | 79 | 12 |
| 183878 | Coding | 3 | 1771 | ctggaatagatgtgagagat | 78 | 13 |
| 183879 | Coding | 3 | 875 | aaagtcaacagggattgatt | 69 | 14 |
| 183880 | Coding | 3 | 2641 | gatcaagaaaaatgttatgc | 62 | 15 |
| 183881 | Coding | 3 | 1753 | atccaagtgctactgtagta | 86 | 16 |
| 183882 | Coding | 3 | 1027 | tttcctcaagattgagagat | 78 | 17 |
| 183883 | Coding | 3 | 2202 | caaagcacagaatctctctg | 68 | 18 |
| 183884 | Coding | 3 | 2172 | cattaacttgcaaagttcct | 58 | 19 |
| 183885 | Coding | 3 | 1545 | atccagtttggaatggagac | 43 | 20 |
| 183886 | Coding | 3 | 2881 | ttagcatcattaacagctca | 72 | 21 |
| 183887 | Coding | 3 | 1312 | taaacaactctgtaacccta | 41 | 22 |
| 183888 | Coding | 3 | 528 | agaaacatcagatgatggat | 82 | 23 |
| 183889 | Coding | 3 | 1898 | agtgaacttagaagatcagt | 66 | 24 |
| 183890 | Coding | 3 | 2849 | ttcagctgatcaaggagatg | 64 | 25 |
| 183891 | Coding | 3 | 840 | ccgagctctcttatcaacag | 81 | 26 |
| 183892 | Coding | 3 | 1581 | agcttctgcattgtgttggt | 76 | 27 |
| 183893 | 3'UTR | 3 | 3597 | attcaactgaatttacagta | 56 | 28 |
| 183894 | Coding | 3 | 3144 | cagaggtaatctgctctttg | 66 | 29 |
| 183895 | Coding | 3 | 1341 | acactggtcaagttcatttt | 74 | 30 |
| 183896 | Coding | 3 | 1456 | cagtactttccaaagctgat | 40 | 31 |
| 183897 | Coding | 3 | 2119 | cagttaggtttccacattgc | 77 | 32 |
| 183898 | 3'UTR | 3 | 3707 | ctactttatatgaaaactag | 30 | 33 |
| 183899 | Coding | 3 | 1053 | atgagcatattccaatgtac | 76 | 34 |
| 183900 | Coding | 3 | 536 | agtctctcagaaacatcaga | 67 | 35 |
| 183901 | Coding | 3 | 394 | taccagccaagggatcctct | 79 | 36 |
| 183902 | Coding | 3 | 489 | ttcattatagatctccaaca | 39 | 37 |
| 183903 | Coding | 3 | 1619 | ttaaacagactattcaggtt | 64 | 38 |
| 183904 | Coding | 3 | 2960 | tcttcagtatactgccccag | 72 | 39 |
| 183905 | Coding | 3 | 2301 | actgtgaaaagtcattttgt | 48 | 40 |
| 183906 | Coding | 3 | 1159 | caagatctcgttttaaacgt | 76 | 41 |
| 183907 | Coding | 3 | 308 | tggccatacgcaaagatagt | 34 | 42 |
| 183908 | Coding | 3 | 2260 | gctgtatattttcctggaca | 76 | 43 |
| 183909 | Coding | 3 | 1659 | ttgctttgagctgccatcct | 0 | 44 |
| 183910 | Coding | 3 | 2333 | gagaagccatcagaatcagc | 71 | 45 |
| 183911 | Coding | 3 | 1023 | ctcaagattgagagatgcag | 79 | 46 |
| 183912 | Coding | 3 | 2620 | gtttctcatgagctgcctta | 71 | 47 |

As shown in Table 1, SEQ ID NOs 12, 13, 14, 15, 16, 17, 18, 21, 23, 24, 25, 26, 27, 29, 30, 32, 34, 35, 36, 38, 39, 41, 43, 45, 46 and 47 demonstrated at least 61% inhibition of human kinesin-like 1 expression in this assay and are therefore preferred. The target sites to which these preferred sequences are complementary are herein referred to as "preferred target regions" and are therefore preferred sites for targeting by compounds of the present invention.

TABLE 2

Sequence and position of preferred target regions identified in kinesin-like 1

| SITE ID | TARGET SEQ ID NO | TARGET SITE | SEQUENCE | REV COMP OF SEQ ID | ACTIVE IN | SEQ ID NO |
|---|---|---|---|---|---|---|
| 99215 | 3 | 1838 | gaacaatcattagcagcaga | 12 | *H. sapiens* | 48 |
| 99216 | 3 | 1771 | atctctcacatctattccag | 13 | *H. sapiens* | 49 |
| 99217 | 3 | 875 | aatcaatccctgttgacttt | 14 | *H. sapiens* | 50 |
| 99218 | 3 | 2641 | gcataacatttttcttgatc | 15 | *H. sapiens* | 51 |
| 99219 | 3 | 1753 | tactacagtagcacttggat | 16 | *H. sapiens* | 52 |
| 99220 | 3 | 1027 | atctctcaatcttgaggaaa | 17 | *H. sapiens* | 53 |
| 99221 | 3 | 2202 | cagagagattctgtgctttg | 20 | *H. sapiens* | 54 |
| 99224 | 3 | 2881 | tgagctgttaatgatgctaa | 22 | *H. sapiens* | 55 |
| 99226 | 3 | 528 | atccatcatctgatgtttct | 23 | *H. sapiens* | 56 |
| 99227 | 3 | 1898 | actgatcttctaagttcact | 24 | *H. sapiens* | 57 |
| 99228 | 3 | 2849 | catctccttgatcagctgaa | 25 | *H. sapiens* | 58 |
| 99229 | 3 | 840 | ctgttgataagagagctcgg | 26 | *H. sapiens* | 59 |
| 99230 | 3 | 1581 | accaacacaatgcagaagct | 28 | *H. sapiens* | 60 |
| 99232 | 3 | 3144 | caaagagcagattacctctg | 29 | *H. sapiens* | 61 |
| 99233 | 3 | 1341 | aaaatgaacttgaccagtgt | 31 | *H. sapiens* | 62 |
| 99235 | 3 | 2119 | gcaatgtggaaacctaactg | 33 | *H. sapiens* | 63 |
| 99237 | 3 | 1053 | gtacattggaatatgctcat | 34 | *H. sapiens* | 64 |
| 99238 | 3 | 536 | tctgatgtttctgagagact | 35 | *H. sapiens* | 65 |
| 99239 | 3 | 394 | agaggatcccttggctggta | 37 | *H. sapiens* | 66 |
| 99241 | 3 | 1619 | aacctgaatagtctgtttaa | 38 | *H. sapiens* | 67 |
| 99242 | 3 | 2960 | ctggggcagtatactgaaga | 40 | *H. sapiens* | 68 |
| 99244 | 3 | 1159 | acgtttaaaacgagatcttg | 42 | *H. sapiens* | 69 |
| 99246 | 3 | 2260 | tgtccaggaaaatatacagc | 44 | *H. sapiens* | 70 |
| 99248 | 3 | 2333 | gctgattctgatggcttctc | 45 | *H. sapiens* | 71 |
| 99249 | 3 | 1023 | ctgcatctctcaatcttgag | 46 | *H. sapiens* | 72 |
| 99250 | 3 | 2620 | taaggcagctcatgagaaac | 47 | *H. sapiens* | 73 |

As these "preferred target regions" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these sites and consequently inhibit the expression of kinesin-like 1.

Example 16

Western Blot Analysis of Kinesin-Like 1 Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to kinesin-like 1 is used, with a radiolabeled or fluorescently labeled secondary antibody directed against the primary antibody species. Bands are visualized using a PHOSPHORIMAGER™ (Molecular Dynamics, Sunnyvale Calif.).

Example 17

Cell Cycle Assay and Flow Cytometry Analysis

The measurement of the DNA content of cells can provide a great deal of information about the cell cycle, and consequently the effect on the cell cycle of added stimuli (e.g. transfected genes or drug treatment). Therefore, in a further embodiment of the invention, antisense compounds were analyzed for their effects on the cell cycle (DNA content) by fluorescence-activated cell sorting (FACS) analysis in MCF-7, T47D and HMEC cells. This analysis is based on the principle that the DNA content of a cell changes through the progression of the cell cycle and that this change can be quantitated by staining the DNA and measuring the amount of stain over a period of time. Flow cytometry (FACS) is a means of measuring certain physical and chemical characteristics, such as the DNA content, of cells or particles as they travel in suspension one by one past a sensing point.

When cells reached 70% confluency, they were treated with antisense oligonucleotide (ISIS 183881, SEQ ID NO: 16) or a control oligonucleotide, ISIS 29848, a 20-mer random oligonucleotide (NNNNNNNNNNNNNNNNNNNN, wherein each N can be A, C, G or T; herein incorporated as SEQ ID NO: 74) as described in other examples herein. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. After 4-7 hours of treatment, the medium was replaced with fresh medium. Cells were harvested 16-24 hours after oligonucleotide treatment and the growth medium (including floating cells) were transferred to fluorescence-activated cell sorting (FACS) tubes. The remaining cells were detached from the plates with gentle tapping and were washed with 250 μl PBS/5 mM EDTA. Following the wash, 250 μl trypsin was added to the cells and incubated at room temperature for 5 minutes. These cells were then added to the FACS tubes. Tubes were spun in a tabletop centrifuge at 2000 rpm for 5 minutes and the supernatant was decanted.

Cells were then washed with 2 ml PBS/5 mM EDTA and the tubes were spun again at 2000 rpm for 5 minutes with the supernatant being decanted after centrifugation. Cells were then resuspended with 0.4 ml PBS/5mM EDTA and briefly vortexed. Following resuspension and vortexing, 1.6 mL cold ethanol was added while the tube was again gently vortexed.

Cells were stored at −20° C. overnight. The following day, tubes were spun at 2000 rpm and the supernatant was decanted. Cells were then washed with 2 mL PBS/5 mM EDTA and resuspended with 0.15 ml PI mix (100 μg/ml propidium iodide, 1:200 RNAse cocktail; Ambion, Inc. (Austin, Tex.), Catalog Number #2286). Samples were then run on a flow cytometer and the data were analyzed via the ModFit™ algorithm (AMPL Software Pty Ltd, Turramurra, Australia) to determine the distribution of cells in subG1, G1-, S- and G2/M-phases of mitosis. The percent of cells arrested in the G2/M phase of the cell cycle for each cell line is shown in Table 3. Data are compared to untreated controls (UTC) and the control antisense oligonucleotide, ISIS 29848. Data are an average of two assays.

TABLE 3a

Percent Arrest in G2/M phase of the cell cycle by ISIS 183881

| Cell line | Percent G2/M Arrest UTC | Control; ISIS 29848 | ISIS 183881 |
|---|---|---|---|
| MCF-7 | 7 | 8 | 23 |
| T47D | 15 | 20 | 45 |
| HMEC | 14 | 15 | 28 |

These data indicate that ISIS 183881 was able to arrest cancer cells in the G2/M phase of the cell cycle. This experiment was repeated with the cancer cell lines; data are shown in Table 3b.

TABLE 3b

Percent Arrest in G2/M phase of the cell cycle by ISIS 183881

| Cell line | Percent G2/M Arrest UTC | Control; ISIS 29848 | ISIS 183881 |
|---|---|---|---|
| MCF-7 | 13 | 15 | 34 |
| T47D | 15 | 20 | 41 |

It was also demonstrated that this antisense compound had no effect on cell polyploidy. These data are shown in Table 4.

TABLE 4

Percent Polyploidy after treatment with ISIS 183881

| Cell line | Percent Polyploidy UTC | Control; ISIS 29848 | ISIS 183881 |
|---|---|---|---|
| MCF-7 | 12 | 13 | 14 |
| T47D | 19 | 23 | 20 |
| HMEC | 3 | 4 | 5 |

These data indicate that the antisense compound, ISIS 183881 did not induce the production of multiple nuclei, but in fact arrested cells in mitosis.

Treatment of T47D cells with ISIS 183891 also caused rounding of cells, which was not seen with a control oligonucleotide or in untreated controls.

Example 18

Dose Responsiveness and Time Course of the Arrest of T47D Cells in G2/M by Treatment With Antisense to Kinesin-Like 1

T47D cells were cultured and treated with ISIS 183891 as described above, using oligonucleotide concentrations of 0, 50, 100, 150 and 200 nM. At these doses, the percentage of cells in G2/M was approximately 23%, 40%, 47%, 50% and 54%, respectively.

In a time course using 150 nM ISIS 183891, the percentage of T47D cells in G2M was observed to increase from 20% at time 0 to 55% at 24 hours after treatment, 50% at 48 hours and 32% at 72 hours.

Example 19

G2/M Arrest by Antisense Knockdown of Kinesin-Like 1 Compared to Knockdown of Other Genes in Breast Cancer Cell Lines or Normal Breast Cell Lines Several breast cell lines were treated with an antisense inhibitor of kinesin-like 1 or with an antisense inhibitor of one of 19 other randomly selected cellular genes. In the MCF7 human breast cancer cell line, the percentage of cells in G2/M after treatment with antisense to kinesin-like 1 (ISIS 183881) was over triple the percentage of control-treated cells in G2M. In contrast, cells treated with antisense inhibitors of the other genes showed no increase or an increase of less than 1.3 fold.

In HMEC (normal human mammary epithelial) cells the percentage of cells in G2/M after treatment with antisense to kinesin-like 1 (ISIS 183881) was increased to approximately 1.5 fold the percentage of control-treated cells in G2M. In contrast, cells treated with antisense inhibitors of the other genes showed no increase or an increase of less than 1.3 fold.

In T47D human breast carcinoma cells, the percentage of cells in G2/M after treatment with antisense to kinesin-like 1 (ISIS 183881) was increased to approximately 2.1 fold the percentage of control-treated cells in G2M. In contrast, cells treated with antisense inhibitors of the other genes showed no increase or an increase of less than 1.2 fold.

Example 20

Expression of Kinesin-Like 1 in Transformed vs. Primary Cultured Cells

Relative levels of kinesin-like 1 RNA were determined by RT-PCR in 14 transformed human cell lines and 5 primary (non-transformed) human cell cultures. Relative kinesin-like RNA levels in each cell type were normalized to levels in T47D cells. Results are shown in Table 5.

TABLE 5

Relative kinesin-like 1 RNA levels in cultured cells

| Cell name | Cell type | Transformed or primary | Kinesin-like 1 RNA level (as % of levels in T47D cells) |
|---|---|---|---|
| T47D | Breast adenocarcinoma | Transformed | 100% |
| T47Dp53 | Breast adenocarcinoma | Transformed | 38 |
| MCF7 | Breast carcinoma | Transformed | 100 |
| A549 | Lung carcinoma | Transformed | 125 |
| 769-P | Kidney epithelial carcinoma | Transformed | 82 |
| T24 | Bladder carcinoma | Transformed | 142 |
| HepG2 | Liver Carcinoma | Transformed | 34 |
| Hep3B | Hepatocellular carcinoma | Transformed | 70 |
| HeLa | Cervical carcinoma | Transformed | 83 |
| SK-OV-3 | Ovarian carcinoma | Transformed | 37 |
| DU145 | Prostate carcinoma | Transformed | 131 |
| PC3 | Prostate cancer | Transformed | 52 |
| U87-MG | Glioblastoma | Transformed | 92 |
| Jurkat | T-cell leukemia | Transformed | 130 |
| Huvec | Normal vascular endothelium | Primary | 80 |
| HMEC | Normal mammary epithelium | Primary | 20 |
| PreD | Normal pre-adipocyte | Primary | 20 |
| D3 | Normal differentiated adipocyte | Primary | 1 |
| Dendritic | Normal dendritic | Primary | undetectable |

Example 21

Kinesin-like 1 Protein Expression in Cultured Cells

Levels of kinesin-like 1 protein were measured in cultured cells by western blotting and normalized to GAPDH. Results are shown in Table 6 relative to kinesin-like 1 levels in T47D cells.

TABLE 6

Kinesin-like 1 protein levels in cultured cells

| Cell name | Cell type | Transformed or primary | Relative kinesin-like 1 protein levels |
|---|---|---|---|
| T47D | Breast adenocarcinoma | Transformed | 100% |
| T47Dp53 | Breast adenocarcinoma | Transformed | 141 |
| MCF7 | Breast carcinoma | Transformed | 141 |
| U266 | Multiple myeloma | Transformed | 97 |
| 769-P | Kidney epithelial carcinoma | Transformed | 58 |
| T24 | Bladder carcinoma | Transformed | 151 |
| Hep3B | Hepatocellular carcinoma | Transformed | 69 |
| HeLa | Cervical carcinoma | Transformed | 73 |
| SK-OV-3 | Ovarian carcinoma | Transformed | 61 |
| DU145 | Prostate carcinoma | Transformed | 51 |
| PC3 | Prostate cancer | Transformed | 107 |
| U87-MG | Glioblastoma | Transformed | 116 |
| Huvec | Normal vascular endothelium | Primary | 54 |

Example 22

Antisense Inhibition of Kinesin-Like 1 Expression Arrests Many Cell Types in G2/M A panel of cell types was treated with ISIS 183891, an antisense inhibitor of kinesin-like 1, or with an unrelated control oligonucleotide, and the percentage of cells in G2/M was assayed, using methods described in previous examples. Results are shown in Table 7 as approximate percentage of cells in G2/M.

TABLE 7

Antisense inhibition of kinesin-like 1 causes G2/M arrest

| Cell name | Cell type | % of cells in G2/M (control oligo) | % of cells in G2/M (ISIS 183891) |
|---|---|---|---|
| T47D | Breast adenocarcinoma | 20 | 32 |
| T47Dp53 | Breast adenocarcinoma | 13 | 32 |
| MCF7 | Breast carcinoma | 14 | 25 |
| MDA-MB231 | Breast carcinoma | 14 | 47 |
| A549 | Lung carcinoma | 15 | 90 |
| T24 | Bladder carcinoma | 15 | 32 |
| DU145 | Prostate carcinoma | 16 | 32 |
| PC3 | Prostate carcinoma | 17 | 91 |
| MiaPaca | Pancreatic carcinoma | 16 | 47 |
| Panc 1 | Pancreatic carcinoma | 18 | 52 |
| HeLa | Cervical carcinoma | 20 | 60 |
| SK-OV-3 | Ovarian carcinoma | 27 | 68 |
| U87-MG | Glioblastoma | 16 | 42 |
| Hep3B | Hepatocellular carcinoma | 30 | 54 |
| 769-P | Kidney carcinoma | 46 | 69 |
| Huvec | Normal human vascular endothelium | 16 | 47 |
| HMEC | Normal mammary epithelium | 31 | 51 |

Example 23

Inhibition of Kinesin-Like 1 mRNA Expression in MCF7 Breast Cancer Cells is Dose-Dependent MCF7 cells were cultured as described in previous examples and treated with ISIS 183881 at concentrations of 30 nM and 100 nM. At 30 nM ISIS 183881, kinesin-like 1 expression as measured by RT-PCR was reduced by almost 80% compared to untreated control. At 100 nM ISIS 183881, kinesin-like 1 expression was reduced by approximately 90% compared to untreated control. The IC50 was 20 nM. In contrast, kinesin-like 1 in cells treated with an unrelated control oligonucleotide was not reduced by more than 10% at either concentration of oligonucleotide.

Example 24

Effect of Kinesin-Like 1 Antisense Oligonucleotides on Kinesin-Like 1 mRNA Levels and G2/M Arrest in T47D Human Breast Carcinoma Cells The kinesin-like 1 antisense oligonucleotides ISIS 183881 and ISIS 183891 were tested for dose-dependent effects on kinesin-like 1 expression and G2/M arrest in T47D human breast carcinoma cells. The negative control oligonucleotide used, ISIS 335395 (CCAGGCCTTCTATTCACAAG; SEQ ID NO: 75), is an 8-base mismatch of ISIS 183891.

Cells were treated with oligonucleotides for 24 hours at concentrations of 0, 0.5, 1, 5, 10, 25, 50 and 100 nM. Dose-dependent reduction in kinesin-like 1 mRNA was measured by RT-PCR and results are shown in Table 8.

TABLE 8

| Antisense inhibition of kinesin-like 1 expression in T47D breast carcinoma cells | | | |
|---|---|---|---|
| | Percent inhibition after treatment with: | | |
| Oligonucleotide dose (nM) | ISIS 335395 | ISIS 183881 | ISIS 183891 |
| 0 | 0 | 0% | 0 |
| 0.5 | 34 | 14 | 12 |
| 1 | 30 | 30 | 21 |
| 5 | 30 | 20 | 41 |
| 10 | 28 | 24 | 46 |
| 25 | 14 | 42 | 53 |
| 50 | 13 | 43 | 61 |
| 100 | 20 | 40 | 75 |

Inhibition of kinesin-like 1 expression was dose dependent. The percentage of cells in G2/M was also determined for these treated cells. Data are shown in Table 9.

TABLE 9

| Percentage of T47D breast carcinoma cells in G2/M after inhibition of kinesin-like 1 expression | | | | | | |
|---|---|---|---|---|---|---|
| | Percent of cells in G2/M after treatment with: | | | | | |
| Oligo | ISIS 335395 | | ISIS 183881 | | ISIS 183891 | |
| dose (nM) | 24 hr | 48 hr | 24 hr | 48 hr | 24 hr | 48 hr |
| 0 | 13 | 30 | 13 | 30 | 13 | 30 |
| 25 | 13 | 31 | 20 | 32 | 26 | 43 |
| 50 | 14 | 31 | 21 | 39 | 32 | 53 |
| 100 | 16 | 30 | 28 | 48 | 34 | 54 |

Example 25

Inhibition of Kinesin-Like 1 Protein Expression in T47D Cells

T47 cells were cultured as in previous examples. Cells were treated with ISIS 183891 at 200 nM for 48 hours. Kinesin-like 1 protein levels were quantitated by western blot analysis using mouse anti-human Eg5 (kinesin-like 1) antibody (BD Biosciences Pharmingen, San Diego Calif., catalog #611187) and normalized to G3PDH. Treatment with ISIS 183891 reduced kinesin-like 1 protein levels by 85%.

Example 26

Kinesin-Like 1 Antisense Oligonucleotide Inhibits T47D Cell Proliferation

T47D cells were cultured as in previous examples. Cells were treated with the kinesin-like 1 antisense oligonucleotide ISIS 183891 and an unrelated control oligonucleotide at 200 nM for 24, 48 or 72 hours. Results are shown in Table 10.

TABLE 10

| Antisense to kinesin-like 1 (ISIS 183891) inhibits T47D cell proliferation (expressed in relative cell number) | | | |
|---|---|---|---|
| Time | Untreated control | Control oligonucleotide | ISIS 183891 |
| 24 hr | 50 | 60 | 30 |
| 48 hr | 85 | 100 | 28 |
| 72 hr | 220 | 200 | 30 |

Example 27

Effect of Kinesin-Like 1 Antisense Oligonucleotides on Kinesin-Like 1 mRNA Levels and G2/M Arrest in MDA-MB231 Human Breast Carcinoma Cells The kinesin-like 1 antisense oligonucleotides ISIS 183881 and ISIS 183891 were tested for dose-dependent effects on kinesin-like 1 expression and G2/M arrest in MDA-MB231 human breast carcinoma cells. The negative control oligonucleotide used, ISIS 335395 (CCAGGCCTTCTATTCACAAG; SEQ ID NO: 75), is an 8-base mismatch of ISIS 183891.

Cells were treated with oligonucleotides for 24 hours at concentrations of 0, 0.5, 1, 5, 10, 25, 50 and 100 nm. Dose-dependent reduction in kinesin-like 1 mRNA was measured by RT-PCR and results are shown in Table 11.

TABLE 11

| Antisense inhibition of kinesin-like 1 expression in MDA-MB231 breast carcinoma cells | | | |
|---|---|---|---|
| | Percent inhibition after treatment with: | | |
| Oligonucleotide dose (nM) | ISIS 335395 | ISIS 183881 | ISIS 183891 |
| 0 | 0 | 0 | 0 |
| 0.5 | 4 | 5 | 0 |
| 1 | 0 | 4 | 4 |
| 5 | 18 | 18 | 34 |
| 10 | 5 | 2 | 43 |
| 25 | 16 | 36 | 54 |
| 50 | 7 | 61 | 73 |
| 100 | 18 | 63 | 69 |

Inhibition of kinesin-like 1 expression was dose dependent. The percentage of cells in G2/M was also determined for these treated cells. Data are shown in Table 12.

TABLE 12

| Percentage of MDA-MB231 breast carcinoma cells in G2/M after inhibition of kinesin-like 1 expression | | | | | | |
|---|---|---|---|---|---|---|
| | Percent of cells in G2/M after treatment with: | | | | | |
| Oligo | ISIS 335395 | | ISIS 183881 | | ISIS 183891 | |
| dose (nM) | 24 hr | 48 hr | 24 hr | 48 hr | 24 hr | 48 hr |
| 0 | 13 | 15 | 13 | 15 | 13 | 15 |
| 25 | 11 | 15 | 23 | 24 | 32 | 37 |
| 50 | 9 | 14 | 35 | 30 | 34 | 46 |
| 100 | 11 | 15 | 44 | 48 | 30 | 40 |

Example 28

Effect of Kinesin-Like 1 Antisense Oligonucleotides on Kinesin-Like 1 mRNA Levels and G2/M Arrest in HeLa Human Cervical Carcinoma Cells The kinesin-like 1 antisense oligonucleotides ISIS 183881 and ISIS 183891 were tested for dose-dependent effects on kinesin-like 1 expression and G2/M arrest in HeLa human cervical carcinoma cells. The negative control oligonucleotide used, ISIS 335395 (CCAGGCCTTCTATTCACAAG; SEQ ID NO: 75), is an 8-base mismatch of ISIS 183891.

Cells were treated with oligonucleotides for 24 hours at concentrations of 0, 0.5, 1, 5, 10, 25, 50 and 100 nM. Dose-dependent reduction in kinesin-like 1 mRNA was measured by RT-PCR and results are shown in Table 13.

TABLE 13

Antisense inhibition of kinesin-like 1 expression in HeLa cervical carcinoma cells

| Oligonucleotide dose (nM) | Percent inhibition after treatment with: ISIS 335395 | ISIS 183881 | ISIS 183891 |
|---|---|---|---|
| 0 | 0 | 0 | 0 |
| 0.5 | 0 | 3 | 12 |
| 1 | 0 | 0 | 0 |
| 5 | 0 | 1 | 30 |
| 10 | 5 | 2 | 33 |
| 25 | 17 | 46 | 61 |
| 50 | 5 | 65 | 84 |
| 100 | 0 | 56 | 84 |

Inhibition of kinesin-like 1 expression was dose dependent.

The percentage of cells in G2/M was also determined for these treated cells. Data are shown in Table 14.

TABLE 14

Percentage of HeLa cervical carcinoma cells in G2/M after inhibition of kinesin-like 1 expression

| Oligo | Approx. percentage of cells in G2/M after treatment with: ISIS 335395 | | ISIS 183881 | | ISIS 183891 | |
|---|---|---|---|---|---|---|
| dose (nM) | 24 hr | 48 hr | 24 hr | 48 hr | 24 hr | 48 hr |
| 0 | 17 | 15 | 17 | 15 | 17 | 15 |
| 25 | 17 | 16 | 16 | 14 | 56 | 39 |
| 50 | 18 | 17 | 23 | 16 | 70 | 67 |
| 100 | 16 | 17 | 48 | 33 | 68 | 68 |

Example 29

Kinesin-like 1 Expression in Tumor and Normal Tissues from Individual Patients

Kinesin-like 1 expression was compared between normal and tumor tissues from over 240 individuals using BD CLONTECH™ Cancer Profiling Array I (Palo Alto Calif.) according to manufacturer's instructions. This array contains matched pairs of cDNA (normal and tumor, each pair from a single patient) spotted side by side on a nylon membrane. A $^{32}$P-labeled probe (nucleotides 1902-3152 of SEQ ID NO: 77) for kinesin-like 1 was hybridized to the array according to manufacturer's instructions.

Results are shown in tabular form in Table 15.

TABLE 15

Human kinesin-like 1 expression in tumor vs. normal tissues

| Tumor type | # Sample Pairs | Detected in Normal Tissue Number | Per-cent | Detected in Tumor Tissue Number | Per-cent | >2 fold in Tumor Number | Per-cent |
|---|---|---|---|---|---|---|---|
| Breast | 53 | 25 | 47 | 41 | 77 | 26 | 49 |
| Colon | 38 | 27 | 71 | 34 | 89 | 10 | 26 |
| Kidney | 21 | 3 | 14 | 5 | 24 | 1 | 5 |
| Lung | 21 | 7 | 33 | 15 | 71 | 12 | 57 |
| Ovary | 16 | 6 | 38 | 15 | 94 | 9 | 56 |
| Rectum | 19 | 14 | 74 | 16 | 84 | 5 | 26 |
| Stomach | 28 | 15 | 54 | 22 | 79 | 11 | 39 |
| Thyroid | 6 | 4 | 67 | 4 | 67 | 1 | 17 |
| Uterus | 44 | 14 | 32 | 33 | 75 | 23 | 52 |

Thus it can be seen that kinesin-like 1 expression is increased twofold in approximately 25-60% of breast, colon, lung, ovary, rectum, stomach and uterus tumor samples, and also (to a lesser extent) in kidney and thyroid tumor samples.

Example 30

Antisense Inhibition of Human Kinesin-Like 1 Expression by Additional Chimeric Phosphorothioate Oligonucleotides Having 2'-MOE Wings and a Deoxy Gap In accordance with the present invention, a series of oligonucleotides were designed to target different regions of the human kinesin-like 1 RNA, using published sequences (GenBank accession number NM_004523.1, incorporated herein as SEQ ID NO: 3; GenBank accession number NT_030059, incorporated herein as SEQ ID NO: 76; GenBank accession number NM_004523.2, incorporated herein as SEQ ID NO: 77; GenBank accession number BL050421.1, incorporated herein as SEQ ID NO: 78; and GenBank accession number BX103943.1, incorporated herein as SEQ ID NO: 79). The oligonucleotides are shown in Table 16. "Target site" indicates the first (5'-most) nucleotide number on the particular target sequence to which the oligonucleotide binds. All compounds in Table 16 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethoxy (2'-MOE) nucleotides. The internucleoside (backbone) linkages are phosphorothioate (P=S) throughout the oligonucleotide. All cytidine residues are 5-methylcytidines. The compounds were analyzed for their effect on human kinesin-like 1 mRNA levels by quantitative real-time PCR as described in other examples herein. Data are averages from two experiments in which T-24 cells were treated with the antisense oligonucleotides of the present invention. As noted, some of the compounds were designed to be fully complementary to more than one animal species (human, mouse, and/or rat).

TABLE 16

Inhibition of human kinesin-like 1 mRNA levels by chimeric phosphorothioate oligonucleotides having 2'-MOE wings and a deoxy gap

| Isis No | Region | Target SEQ ID NO | Target site | Sequence | % inhib | SEQ ID NO | Species |
|---|---|---|---|---|---|---|---|
| 183881 | Coding | 3 | 1753 | atccaagtgctactgtagta | 89 | 16 | Human |
| 183883 | Coding | 3 | 2202 | caaagcacagaatctctctg | 81 | 18 | Human, Mouse |
| 183891 | Coding | 3 | 840 | ccgagctctcttatcaacag | 86 | 26 | Human |
| 285688 | Coding | 3 | 212 | gctccaaacaccatatcaaa | 45 | 80 | Human, Mouse |
| 285689 | Coding | 3 | 217 | tagatgctccaaacaccata | 38 | 81 | Human, Mouse |
| 285694 | Coding | 3 | 936 | tttagattctcgataaggaa | 60 | 82 | Human, Mouse |
| 285695 | Coding | 3 | 941 | gttagtttagattctcgata | 73 | 83 | Human, Mouse |
| 285696 | Coding | 3 | 949 | ggattctagttagtttagat | 43 | 84 | Human, Mouse |
| 285698 | Coding | 3 | 989 | attatagatgttcttgtacg | 73 | 85 | Human, Mouse |
| 285699 | Coding | 3 | 995 | gttgcaattatagatgttct | 88 | 86 | Human, Mouse |
| 285700 | Coding | 3 | 1032 | cagagtttcctcaagattga | 45 | 87 | Human, Mouse |
| 285701 | Coding | 3 | 1037 | gtactcagagtttcctcaag | 75 | 88 | Human, Mouse |
| 285702 | Coding | 3 | 1042 | ccaatgtactcagagtttcc | 58 | 89 | Human, Mouse |
| 285703 | Coding | 3 | 1047 | atattccaatgtactcagag | 37 | 90 | Human, Mouse |
| 285704 | Coding | 3 | 1052 | tgagcatattccaatgtact | 73 | 91 | Human, Mouse |
| 285705 | Coding | 3 | 1122 | ctccttaataagagcttttt | 60 | 92 | Human, Mouse |
| 285706 | Coding | 3 | 1127 | gtatactccttaataagagc | 58 | 93 | Human, Mouse |
| 285708 | Coding | 3 | 1187 | tacactccatttttctcacg | 9 | 94 | Human, Mouse |
| 285712 | Coding | 3 | 1346 | gatttacactggtcaagttc | 58 | 95 | Human, Mouse |
| 285713 | Coding | 3 | 1351 | ggtcagatttacactggtca | 89 | 96 | Human, Mouse |
| 285714 | Coding | 3 | 1356 | ttgcaggtcagatttacact | 77 | 97 | Human, Mouse |
| 344870 | Coding | 3 | 67 | tgcatctcaccaccacctgg | 76 | 98 | Human, Mouse |
| 344871 | Intron 1 | 76 | 10298 | gaagtaaaagcaggtagatg | 19 | 99 | Human |
| 344872 | Intron 1 | 76 | 12002 | acctgagttcatttttccca | 70 | 100 | Human |
| 344873 | Intron 9 | 76 | 28627 | ccgtatactcctacacaaga | 71 | 101 | Human |
| 344874 | Intron 16 | 76 | 46149 | aaaatgcatccaacattctt | 73 | 102 | Human |
| 344875 | Intron 17 | 76 | 51266 | gaaatccatcagtctagata | 28 | 103 | Human |
| 344876 | Intron 20:Exon 21 junction | 76 | 57643 | catccacatcctaaaagaag | 41 | 104 | Human |
| 344877 | Intron 6a:Exon 22a junction | 76 | 61939 | ggatacaactagggttagat | 50 | 105 | Human |
| 344878 | 5' UTR | 77 | 13 | tgcgtggcctggaggaccga | 51 | 106 | Human |
| 344879 | 5' UTR | 77 | 39 | ggagtctccctggtactctc | 22 | 107 | Human |
| 344880 | Start codon | 77 | 126 | gccatgacggtccccgccaa | 69 | 108 | Human |
| 344881 | Coding | 3 | 79 | aattaaatggtctgcatctc | 45 | 109 | Human |
| 344882 | Coding | 3 | 136 | cttttcgtacaggatcacat | 62 | 110 | Human |
| 344883 | Coding | 3 | 245 | acacttcggtaaacatcaat | 25 | 111 | Human, Mouse |
| 344884 | Coding | 3 | 251 | caaacaacacttcggtaaac | 31 | 112 | Human, Mouse |
| 344885 | Coding | 3 | 256 | ttggacaaacaacacttcgg | 68 | 113 | Human, Mouse |
| 344886 | Coding | 3 | 281 | tagcccataataacttcatc | 35 | 114 | Human, Mouse |
| 344887 | Coding | 3 | 286 | aattatagcccataataact | 9 | 115 | Human, Mouse |
| 344888 | Coding | 3 | 329 | aaagtttttccagtgccagt | 78 | 116 | Human, Mouse, Rat |
| 344889 | Coding | 3 | 334 | ttgtaaaagtttttccagtg | 50 | 117 | Human, Mouse, Rat |

TABLE 16-continued

Inhibition of human kinesin-like 1 mRNA levels by chimeric phosphorothioate oligonucleotides having 2'-MOE wings and a deoxy gap

| Isis No | Region | Target SEQ ID NO | Target site | Sequence | % inhib | SEQ ID NO | Species |
|---|---|---|---|---|---|---|---|
| 344890 | Coding | 3 | 346 | tttcaccttccattgtaaaa | 6 | 118 | Human, Mouse, Rat |
| 344891 | Coding | 3 | 351 | tgacctttcaccttccattg | 46 | 119 | Human, Mouse, Rat |
| 344892 | Coding | 3 | 356 | ttaggtgacctttcaccttc | 51 | 120 | Human, Mouse, Rat |
| 344893 | Coding | 3 | 361 | cttcattaggtgacctttca | 39 | 121 | Human, Mouse, Rat |
| 344894 | Coding | 3 | 405 | acgtggaattataccagcca | 93 | 122 | Human, Rat |
| 344895 | Coding | 3 | 428 | ttctcaaaaatttgatgaag | 22 | 123 | Human, Mouse |
| 344896 | Coding | 3 | 437 | tcagtaagtttctcaaaaat | 9 | 124 | Human, Mouse, Rat |
| 344897 | Coding | 3 | 442 | cattatcagtaagtttctca | 38 | 125 | Human, Mouse, Rat |
| 344898 | Coding | 3 | 662 | gcagttgtcctttttgctgc | 78 | 126 | Human, Mouse |
| 344899 | Coding | 3 | 758 | acaagctcttctccatcaat | 45 | 127 | Human, Mouse, Rat |
| 344900 | Coding | 3 | 763 | ttttaacaagctcttctcca | 76 | 128 | Human, Mouse, Rat |
| 344901 | Coding | 3 | 805 | tgttttcacttcctgcaaga | 44 | 129 | Human, Rat |
| 344902 | Coding | 3 | 1218 | actcatgactctaaaatttt | 59 | 130 | Human |
| 344903 | Coding | 3 | 1306 | actctgtaaccctattcagc | 70 | 131 | Human |
| 344904 | Coding | 3 | 1628 | tccatattattaaacagact | 36 | 132 | Human, Mouse |
| 344905 | Coding | 3 | 1781 | gacacattttctggaataga | 69 | 133 | Human, Mouse |
| 344906 | Coding | 3 | 1876 | tgagtacattaatcaattcc | 41 | 134 | Human |
| 344907 | Coding | 3 | 2130 | cttcaggtcttcagttaggt | 62 | 135 | Human, Mouse |
| 344908 | Coding | 3 | 2135 | attgtcttcaggtcttcagt | 25 | 136 | Human, Mouse |
| 344909 | Stop codon | 3 | 3173 | caagtgaattaaaggttgat | 25 | 137 | Human |
| 344910 | 3' UTR | 3 | 3598 | aattcaactgaatttacagt | 10 | 138 | Human |
| 344911 | 3' UTR | 3 | 3641 | caaagtgaactatagggatg | 30 | 139 | Human |
| 344912 | 3' UTR | 77 | 4125 | taaaattctgactactgaaa | 0 | 140 | Human |
| 344913 | 3' UTR | 77 | 4180 | ttgttgacagtgattttaga | 48 | 141 | Human |
| 344914 | 3' UTR | 77 | 4211 | taaaggagggatacaactag | 31 | 142 | Human |
| 344915 | 3' UTR | 77 | 4351 | agtcagatgtctgggtggtc | 61 | 143 | Human |
| 344916 | 3' UTR | 77 | 4367 | gtggcacagagccattagtc | 68 | 144 | Human |
| 344917 | 3' UTR | 77 | 4548 | tcctaagggttaagatttga | 47 | 145 | Human |
| 344918 | 3' UTR | 77 | 4599 | tgaaacatctcaacttccag | 22 | 146 | Human |
| 344919 | 3' UTR | 77 | 4651 | gagcagaaaatttattcttt | 45 | 147 | Human |
| 344920 | 3' UTR | 77 | 4670 | tacacactaaactcatcgtg | 56 | 148 | Human |
| 344921 | 3' UTR | 77 | 4865 | catggatttactgagggcag | 53 | 149 | Human |
| 344922 | 3' UTR | 77 | 4973 | ttattaaccatggatttact | 26 | 150 | Human |
| 344923 | Coding; Exon 1a:Exon 20 junction | 78 | 286 | ggtgtcgtaccaccacctgg | 22 | 151 | Human |
| 344924 | Intron 9 | 76 | 28230 | aaagcctactaggttaatca | 41 | 152 | Human |
| 344925 | Intron 10 | 76 | 28736 | tggaaattaactccatagcc | 45 | 153 | Human |
| 344926 | Coding; Exon 6:Exon 22a junction | 79 | 542 | agggatacaactagagtatg | 14 | 154 | Human |

As shown in Table 16, SEQ ID NOs: 82, 83, 85, 86, 88,89, 91, 92, 93, 95, 96, 97, 98, 100, 101, 102, 108, 110, 113, 116, 122, 126, 128, 130, 131, 133, 135, 143, 144 and 148 gave at least 56% inhibition of kinesin-like 1 and are therefore preferred.

Example 31

Antisense Inhibition of Mouse Kinesin-Like 1 Expression by Chimeric Phosphorothioate Oligonucleotides Having 2'-MOE Wings and a Deoxy Gap A series of oligonucleotides were designed to target different regions of the mouse kinesin-like 1 RNA, using published sequences (GenBank accession number AJ223293.1, incorporated herein as SEQ ID NO: 155; and GenBank accession number BB658933.1, incorporated herein as SEQ ID NO: 156). The oligonucleotides are shown in Table 17. "Target site" indicates the first (5'-most) nucleotide number on the particular target sequence to which the oligonucleotide binds. All compounds in Table 17 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethoxy (2'-MOE) nucleotides. The internucleoside (backbone) linkages are phosphorothioate (P=S) throughout the oligonucleotide. All cytidine residues are 5-methylcytidines. The compounds were analyzed for their effect on mouse kinesin-like 1 mRNA levels by quantitative real-time PCR as described in other examples herein. Data are averages from two experiments in which b.END cells were treated with the antisense oligonucleotides of the present invention. As noted, some of the compounds were designed to be fully complementary to more than one animal species (human, mouse, and/or rat).

TABLE 17

Inhibition of mouse kinesin-like 1 mRNA levels by chimeric phosphorothioate oligonucleotides having 2'-MOE wings and a deoxy gap

| Isis No | Region | Target SEQ ID NO | Target site | Sequence | % inhib | SEQ ID NO | Species |
|---|---|---|---|---|---|---|---|
| 285686 | Coding | 155 | 27 | tccgtacactgacttctttc | 66 | 157 | Mouse |
| 285687 | Coding | 155 | 32 | tgcagtccgtacactgactt | 75 | 158 | Mouse |
| 285688 | Coding | 155 | 88 | gctccaaacaccatatcaaa | 72 | 159 | Human Mouse |
| 285689 | Coding | 155 | 93 | tagatgctccaaacaccata | 70 | 160 | Human Mouse |
| 285690 | Coding | 155 | 677 | attttcacttcctgcaagat | 60 | 161 | Mouse |
| 285691 | Coding | 155 | 731 | gttgatatttccagcttccc | 75 | 162 | Mouse |
| 285692 | Coding | 155 | 744 | tcaagagggattggttgata | 58 | 163 | Mouse |
| 285693 | Coding | 155 | 760 | ataactcttcccagagtcaa | 68 | 164 | Mouse |
| 285694 | Coding | 155 | 809 | tttagattctcgataaggaa | 64 | 165 | Human Mouse |
| 285695 | Coding | 155 | 814 | gttagtttagattctcgata | 72 | 166 | Human Mouse |
| 285696 | Coding | 155 | 822 | ggattctagttagtttagat | 61 | 167 | Human Mouse |
| 285697 | Coding | 155 | 834 | gagaatcttgcaggattcta | 67 | 168 | Mouse |
| 285698 | Coding | 155 | 862 | attatagatgttcttgtacg | 49 | 169 | Human Mouse |
| 285699 | Coding | 155 | 868 | gttgcaattatagatgttct | 75 | 170 | Human Mouse |
| 285700 | Coding | 155 | 905 | cagagtttcctcaagattga | 67 | 171 | Human Mouse |
| 285701 | Coding | 155 | 910 | gtactcagagtttcctcaag | 78 | 172 | Human Mouse |
| 285702 | Coding | 155 | 915 | ccaatgtactcagagtttcc | 76 | 173 | Human Mouse |
| 285703 | Coding | 155 | 920 | atattccaatgtactcagag | 70 | 174 | Human Mouse |
| 285704 | Coding | 155 | 925 | tgagcatattccaatgtact | 70 | 175 | Human Mouse |
| 285705 | Coding | 155 | 995 | ctccttaataagagcttttt | 60 | 176 | Human Mouse |
| 285706 | Coding | 155 | 1000 | gtatactccttaataagagc | 65 | 177 | Human Mouse |
| 285707 | Coding | 155 | 1032 | caagatctcgcttcaaacgc | 76 | 178 | Mouse |
| 285708 | Coding | 155 | 1060 | tacactccatttttctcacg | 75 | 179 | Human Mouse |
| 285709 | Coding | 155 | 1091 | attcatggctctaaaacttt | 49 | 180 | Mouse |
| 285710 | Coding | 155 | 1160 | ctcctcctcaagaacagcga | 74 | 181 | Mouse |
| 285711 | Coding | 155 | 1204 | agttcgttcttactatccat | 73 | 182 | Mouse |
| 285712 | Coding | 155 | 1219 | gatttacactggtcaagttc | 66 | 183 | Human Mouse |
| 285713 | Coding | 155 | 1224 | ggtcagatttacactggtca | 77 | 184 | Human Mouse |
| 285714 | Coding | 155 | 1229 | ttgcaggtcagatttacact | 78 | 185 | Human Mouse |

TABLE 17-continued

Inhibition of mouse kinesin-like 1 mRNA levels by chimeric phosphorothioate oligonucleotides having 2'-MOE wings and a deoxy gap

| Isis No | Region | Target SEQ ID NO | Target site | Sequence | % inhib | SEQ ID NO | Species |
|---|---|---|---|---|---|---|---|
| 285715 | Coding | 155 | 1264 | tgtttctgagtggtttcaag | 67 | 186 | Mouse |
| 285716 | Coding | 155 | 1321 | tccaaggctgaagagacata | 59 | 187 | Mouse |
| 285717 | Coding | 155 | 1330 | tcggttctttccaaggctga | 77 | 188 | Mouse |
| 285718 | Coding | 155 | 1356 | tgctggccgtgtcatgcagt | 75 | 189 | Mouse |
| 285719 | Coding | 155 | 1379 | ttctttaaccgtgttaagca | 74 | 190 | Mouse |
| 285720 | Coding | 155 | 1742 | atcaatcaatccttgcagaa | 71 | 191 | Mouse |
| 285721 | Coding | 155 | 1818 | tatttatgttcaagatggaa | 58 | 192 | Mouse |
| 285722 | Coding | 155 | 1950 | aagaaactgtgttttctcgg | 66 | 193 | Mouse |
| 285723 | Coding | 155 | 1972 | agcttttgtgattcaaccaa | 73 | 194 | Mouse |
| 285724 | Coding | 155 | 2085 | catacttcttctccaaagca | 56 | 195 | Mouse |
| 285725 | Coding | 155 | 2139 | tagacctccgctctgtattt | 61 | 196 | Mouse |
| 285726 | Coding | 155 | 2208 | cttgtaataatccatcagat | 60 | 197 | Mouse |
| 285727 | Coding | 155 | 2224 | ttaaagtgtctgagttcttg | 61 | 198 | Mouse |
| 285728 | Coding | 155 | 2288 | caggttgctgttgagtgaac | 53 | 199 | Mouse |
| 285729 | Coding | 155 | 2295 | cagtctccaggttgctgttg | 61 | 200 | Mouse |
| 285730 | Coding | 155 | 2374 | aggcaggatgcccactgatc | 74 | 201 | Mouse |
| 285731 | Coding | 155 | 2412 | actccattaaattctcaagt | 71 | 202 | Mouse |
| 285732 | Coding | 155 | 2484 | caacacgtgcgctctgttct | 50 | 203 | Mouse |
| 285733 | Coding | 155 | 2496 | tgtgctggttcgcaacacgt | 43 | 204 | Mouse |
| 285734 | Coding | 155 | 2599 | aagcaattcagctttgttaa | 67 | 205 | Mouse |
| 285735 | Coding | 155 | 2606 | tttcagaaagcaattcagct | 61 | 206 | Mouse |
| 285736 | Coding | 155 | 2643 | gtgtcatacctgttgggata | 55 | 207 | Mouse |
| 285737 | Coding | 155 | 2652 | tcctctctggtgtcatacct | 76 | 208 | Mouse |
| 285738 | Coding | 155 | 2683 | ctcacaagtgttgttggata | 76 | 209 | Mouse |
| 285739 | Coding | 155 | 2754 | ctgagctgtttagcatcatt | 67 | 210 | Mouse |
| 285740 | Coding | 155 | 2840 | tgtctctggacttacaagtt | 55 | 211 | Mouse |
| 285741 | Coding | 155 | 2852 | gggtagttcagttgtctctg | 31 | 212 | Mouse |
| 285742 | Coding | 155 | 2888 | aaatggaagacctctgctgg | 40 | 213 | Mouse |
| 285743 | Coding | 155 | 2895 | gctggaaaaatggaagacct | 56 | 214 | Mouse |
| 285744 | Coding | 155 | 3036 | ctcagatcagctagaggttt | 64 | 215 | Mouse |
| 285745 | Coding | 155 | 3041 | taagcctcagatcagctaga | 71 | 216 | Mouse |
| 285746 | 3' UTR | 155 | 3064 | gttgtattttaaagatgaca | 70 | 217 | Mouse |
| 285747 | 3' UTR | 155 | 3152 | agactttcagttcaactaca | 79 | 218 | Mouse |
| 285748 | 3' UTR | 155 | 3228 | acacacacacatattcaatg | 64 | 219 | Mouse |
| 285749 | 3' UTR | 155 | 3272 | atacttacttgttacagaag | 42 | 220 | Mouse |
| 285750 | 3' UTR | 155 | 3429 | aaaagggagacaggagtcga | 59 | 221 | Mouse |
| 285751 | 3' UTR | 155 | 3500 | ttccaggtaaaaccctgcgt | 58 | 222 | Mouse |
| 285752 | 3' UTR | 155 | 3702 | agacttaaagaccttttaag | 48 | 223 | Mouse |
| 285753 | 3' UTR | 155 | 3921 | ctctctgcatacacttttag | 62 | 224 | Mouse |
| 285754 | 3' UTR | 155 | 3979 | ctgtgccaaaaccacatcac | 65 | 225 | Mouse |
| 285755 | 3' UTR | 155 | 4016 | tagtgagtccaaagccagcc | 59 | 226 | Mouse |
| 285756 | 3' UTR | 155 | 4035 | ggatgactgtcctgctgcat | 73 | 227 | Mouse |
| 285757 | 3' UTR | 155 | 4058 | gtctgtattcccaggccttg | 73 | 228 | Mouse |
| 285758 | 3' UTR | 155 | 4175 | agatcaggctggcctcgaaa | 90 | 229 | Mouse |
| 285759 | 3' UTR | 155 | 4258 | ctctttgttacaaagttcta | 73 | 230 | Mouse |
| 285760 | 3' UTR | 155 | 4366 | taatttttattaaaataacg | 0 | 231 | Mouse |
| 285761 | 5' UTR | 156 | 223 | tcctctttcttcttcaaaga | 66 | 232 | Mouse |
| 285762 | 5' UTR | 156 | 255 | atctcaccaccacctggatg | 64 | 233 | Human Mouse |
| 285763 | 5' UTR | 156 | 301 | actgagtgggcattagcttt | 66 | 234 | Mouse |

For mouse kinesin-like 1 the PCR primers were:

forward primer: GCTTCAAGTTCGGAGATCACTAAGA (SEQ ID NO: 235)

reverse primer: CGGAAGTCATCTGAGCAACAAA (SEQ ID NO: 236) and the PCR probe was: FAM-AGAACA-GAGCGCACGTGTTGCGA-TAMRA (SEQ ID NO: 237) where FAM is the fluorescent dye and TAMRA is the quencher dye.

Example 32

Mouse Kinesin-Like 1 Antisense Compounds Reduce Kinesin-Like 1 mRNA in B16 Melanoma Cells Mouse B16 melanoma cells (American Type Culture Collection, Manassas Va.) were cultured in DMEM with 10% fetal bovine serum and penicillin/streptomycin. Cells were treated with ISIS 285714, 285717 and 285747 at 200 nM for 4 hours in Opti-MEM. Kinesin-like 1 mRNA levels were measured by RT-PCR after 24 hours. ISIS 285714, 285717 and 285747 reduced kinesin-like 1 RNA levels by 78%, 80% and 85%, respectively.

Example 33

Mouse Kinesin-Like 1 Antisense Compounds Induce G2/M Arrest in B16 Melanoma Cells Mouse B16 melanoma cells were treated with ISIS 285714, 285717 and 285747 and the percentage of cells in G2/M was measured as in previous examples. The percentage of cells in G2/M after treatment with Isis 285714, 285717 and 285747 was 22%, 18% and 19%, respectively after 48 hours and 34%, 43% and 31%, respectively, after 72 hours, whereas cells treated with unrelated control oligonucleotide had fewer cells in G2/M (20% of cells after 48 hr, 27% after 72 hr).

Example 34

Antisense Inhibitors of kinesin-like 1 are Nontoxic in Mice

Male C57B16 mice (Jackson Labs) were dosed intraperitoneally with 200 μl of saline or 50 mg/kg of antisense oligonucleotide (ISIS 285714, ISIS 285717 or ISIS 285747) in 200 μl of saline, twice a week for a total of 5 injections. Twenty four hours after the last does, mice were sacrificed and serum and organs were harvested. Liver and spleen weights were not significantly increased in antisense-treated mice compared to saline treated mice. Serum AST and ALT (measures of liver toxicity) were also not significantly increased after antisense treatment.

Example 35

Kinesin-Like 1 Expression in SV40 Transgenic (HCC) Mice

An HCC mouse model (Taconic, Germantown N.Y.) for hepatocellular carcinoma was used in which transgenic male mice express SV40 T-antigen (Tag) in their livers, which leads to spontaneous development of well-differentiated hepatocellular carcinoma (HCC) carcinomas. Expression of kinesin-like 1 in livers of wild type mice and HCC mice was measured using array blot analysis. Kinesin-like 1 expression in wild type mouse livers as very low, but was shown to be upregulated up to approximately 15 fold in the HCC mice, and even more(up to about 25 fold) as tumors developed.

Example 36

The Effect of Antisense Inhibition of Kinesin-Like 1 Expression in SV40 Transgenic (HCC) Mice HCC mice were treated with ISIS 285714, 285717 or 285747 or with an unrelated control oligonucleotide. HCC and wild type mice were also treated with saline alone. Kinesin-like 1 levels were virtually undetectable by RT-PCR in the wild type mice but easily detectable in the HCC mice as a result of the upregulation described in the previous example. Treatment of HCC mice with ISIS 285714, 285717 or 285747 decreased kinesin-like 1 mRNA levels by 72%, 62% and 90%, respectively. The unrelated control oligonucleotide caused only a 10% reduction in kinesin-like 1 mRNA in HCC mice.

Example 37

Effect of Antisense Inhibitors of Kinesin-Like 1 on U87-MG Human Glioblastoma Tumor Cell Xenografts in Mice Nude mice were injected in the flank with approximately $10^6$ U87-MG human glioblastoma cells. Mice were dosed with ISIS 183891, targeted to human kinesin-like 1, beginning the day after tumor inoculation and continuing every other day. Tumor volume was measured every few days beginning 10 days after inoculation. By day 22, tumor growth was detectably slower in the ISIS 183891-treated mice than in the control-treated mice and at the end of the study at day 30 after inoculation, tumor volume in ISIS 183891-treated mice was approximately 250 $mm^3$, compared to saline-treated and unrelated control oligonucleotide-treated mice in which tumor volume was approximately 650 $mm^3$.

Example 38

Effect of Antisense Inhibitors of Kinesin-Like 1 on MDA-MB231 Human Breast Tumor Cell Xenografts in Mice Nude mice were inoculated with MDA-MB231 human breast cancer cells and were dosed with ISIS 183891, targeted to human kinesin-like 1, as described in the previous example. By day 30, tumor growth was detectably slower in the ISIS 183891-treated mice than in the control-treated mice and at the end of the study at day 41 after inoculation, tumor volume in ISIS 183891-treated mice was approximately 210 $mm^3$, compared to saline-treated and unrelated control oligonucleotide-treated mice in which tumor volume was approximately 430 $mm^3$ and 380 $mm^3$, respectively.

Together, these examples demonstrate that expression of kinesin-like 1 is upregulated in many cancer cell types, and that antisense inhibitors of kinesin-like 1 are effective for downregulating kinesin-like 1 expression and for arresting growth of a variety of cancer and tumor cell types.

Example 39

Design and Screening of Duplexed Antisense RNA Compounds Targeting Kinesin-Like 1

A series of nucleic acid duplexes comprising the antisense compounds of the present invention and their complements was designed to target kinesin-like 1 mRNA, using published sequence information (GenBank accession number NM_004523.1, incorporated herein as SEQ ID NO: 3; GenBank accession number NT_030059, incorporated herein as SEQ ID NO: 76; GenBank accession number NM_004523.2, incorporated herein as SEQ ID NO: 77; GenBank accession number BL050421.1, incorporated herein as SEQ ID NO: 78; and GenBank accession number BX103943.1, incorporated herein as SEQ ID NO: 79). Each duplex is 20 nucleotides in length with blunt ends (no overhangs). The sequence of each antisense strand is listed in Table 18. The sense strand of the dsRNA was designed and synthesized as the complement of the antisense strand. All compounds in Table 18, as well as their complementary sense strands, are oligoribonucleotides, 20 nucleotides in length with phosphodiester internucleoside linkages (backbones) throughout. These sequences are shown to contain thymine (T) but one of skill in the art will appreciate that thymine (T) is generally replaced by uracil (U) in RNA sequences.

TABLE 18 dsRNAs targeted to human kinesin-like 1

| ISIS # of antisense strand | Corresponds to sequence of | Region | Target SEQ ID NO | Target site | Sequence | SEQ ID NO |
|---|---|---|---|---|---|---|
| 347226 | 183881 | Coding | 3 | 1753 | atccaagtgctactgtagta | 16 |
| 347231 | 183883 | Coding | 3 | 2202 | caaagcacagaatctctctg | 18 |

TABLE 18-continued dsRNAs targeted to human kinesin-like 1

| ISIS # of antisense strand | Corresponds to sequence of | Region | Target SEQ ID NO | Target site | Sequence | SEQ ID NO |
|---|---|---|---|---|---|---|
| 347206 | 183891 | Coding | 3 | 840 | ccgagctctcttatcaacag | 26 |
| 347185 | 285688 | Coding | 3 | 212 | gctccaaacaccatatcaaa | 80 |
| 347186 | 285689 | Coding | 3 | 217 | tagatgctccaaacaccata | 81 |
| 347207 | 285694 | Coding | 3 | 936 | tttagattctcgataaggaa | 82 |
| 347208 | 285695 | Coding | 3 | 941 | gttagtttagattctcgata | 83 |
| 347209 | 285696 | Coding | 3 | 949 | ggattctagttagtttagat | 84 |
| 347210 | 285698 | Coding | 3 | 989 | attatagatgttcttgtacg | 85 |
| 347211 | 285699 | Coding | 3 | 995 | gttgcaattatagatgttct | 86 |
| 347212 | 285700 | Coding | 3 | 1032 | cagagtttcctcaagattga | 87 |
| 347213 | 285701 | Coding | 3 | 1037 | gtactcagagtttcctcaag | 88 |
| 347214 | 285702 | Coding | 3 | 1042 | ccaatgtactcagagtttcc | 89 |
| 347215 | 285703 | Coding | 3 | 1047 | atattccaatgtactcagag | 90 |
| 347216 | 285704 | Coding | 3 | 1052 | tgagcatattccaatgtact | 91 |
| 347217 | 285705 | Coding | 3 | 1122 | ctccttaataagagcttttt | 92 |
| 347218 | 285706 | Coding | 3 | 1127 | gtatactccttaataagagc | 93 |
| 347219 | 285708 | Coding | 3 | 1187 | tacactccatttttctcacg | 94 |
| 347222 | 285712 | Coding | 3 | 1346 | gatttacactggtcaagttc | 95 |
| 347223 | 285713 | Coding | 3 | 1351 | ggtcagatttacactggtca | 96 |
| 347224 | 285714 | Coding | 3 | 1356 | ttgcaggtcagatttacact | 97 |
| 347172 | 344870 | Coding | 3 | 67 | tgcatctcaccaccacctgg | 98 |
| 347173 | 344871 | Intron 1 | 76 | 10298 | gaagtaaaagcaggtagatg | 99 |
| 347174 | 344872 | Intron 1 | 76 | 12002 | acctgagttcatttttccca | 100 |
| 347175 | 344873 | Intron 9 | 76 | 28627 | ccgtatactcctacacaaga | 101 |
| 347176 | 344874 | Intron 16 | 76 | 46149 | aaaatgcatccaacattctt | 102 |
| 347177 | 344875 | Intron 17 | 76 | 51266 | gaaatccatcagtctagata | 103 |
| 347178 | 344876 | Intron 20:Exon 21 junction | 76 | 57643 | catccacatcctaaaagaag | 104 |
| 347179 | 344877 | Intron 6a:Exon 22a junction | 76 | 61939 | ggatacaactagggttagat | 105 |
| 347180 | 344878 | 5' UTR | 77 | 13 | tgcgtggcctggaggaccga | 106 |
| 347181 | 344879 | 5' UTR | 77 | 39 | ggagtctccctggtactctc | 107 |
| 347182 | 344880 | Start codon | 77 | 126 | gccatgacggtccccgccaa | 108 |
| 347183 | 344881 | Coding | 3 | 79 | aattaaatggtctgcatctc | 109 |
| 347184 | 344882 | Coding | 3 | 136 | cttttcgtacaggatcacat | 110 |
| 347187 | 344883 | Coding | 3 | 245 | acacttcggtaaacatcaat | 111 |
| 347188 | 344884 | Coding | 3 | 251 | caaacaacacttcggtaaac | 112 |
| 347189 | 344885 | Coding | 3 | 256 | ttggacaaacaacacttcgg | 113 |
| 347190 | 344886 | Coding | 3 | 281 | tagcccataataacttcatc | 114 |
| 347191 | 344887 | Coding | 3 | 286 | aattatagcccataataact | 115 |
| 347192 | 344888 | Coding | 3 | 329 | aaagtttttccagtgccagt | 116 |
| 347193 | 344889 | Coding | 3 | 334 | ttgtaaaagtttttccagtg | 117 |
| 347194 | 344890 | Coding | 3 | 346 | tttcaccttccattgtaaaa | 118 |
| 347195 | 344891 | Coding | 3 | 351 | tgacctttcaccttccattg | 119 |
| 347196 | 344892 | Coding | 3 | 356 | ttaggtgacctttcaccttc | 120 |
| 347197 | 344893 | Coding | 3 | 361 | cttcattaggtgacctttca | 121 |
| 347198 | 344894 | Coding | 3 | 405 | acgtggaattataccagcca | 122 |
| 347199 | 344895 | Coding | 3 | 428 | ttctcaaaaatttgatgaag | 123 |
| 347200 | 344896 | Coding | 3 | 437 | tcagtaagtttctcaaaaat | 124 |
| 347201 | 344897 | Coding | 3 | 442 | cattatcagtaagtttctca | 125 |
| 347202 | 344898 | Coding | 3 | 662 | gcagttgtcctttttgctgc | 126 |
| 347203 | 344899 | Coding | 3 | 758 | acaagctcttctccatcaat | 127 |
| 347204 | 344900 | Coding | 3 | 763 | ttttaacaagctcttctcca | 128 |
| 347205 | 344901 | Coding | 3 | 805 | tgttttcacttcctgcaaga | 129 |
| 347220 | 344902 | Coding | 3 | 1218 | actcatgactctaaaatttt | 130 |
| 347221 | 344903 | Coding | 3 | 1306 | actctgtaaccctattcagc | 131 |
| 347225 | 344904 | Coding | 3 | 1628 | tccatattattaaacagact | 132 |
| 347227 | 344905 | Coding | 3 | 1781 | gacacattttctggaataga | 133 |
| 347228 | 344906 | Coding | 3 | 1876 | tgagtacattaatcaattcc | 134 |
| 347220 | 344907 | Coding | 3 | 2130 | cttcaggtcttcagttaggt | 135 |
| 347230 | 344908 | Coding | 3 | 2135 | attgtcttcaggtcttcagt | 136 |
| 347232 | 344909 | Stop codon | 3 | 3173 | caagtgaattaaaggttgat | 137 |
| 347233 | 344910 | 3' UTR | 3 | 3598 | aattcaactgaatttacagt | 138 |
| 347234 | 344911 | 3' UTR | 3 | 3641 | caaagtgaactatagggatg | 139 |
| 347235 | 344912 | 3' UTR | 77 | 4125 | taaaattctgactactgaaa | 140 |
| 347236 | 344913 | 3' UTR | 77 | 4180 | ttgttgacagtgattttaga | 141 |
| 347237 | 344914 | 3' UTR | 77 | 4211 | taaaggagggatacaactag | 142 |
| 347238 | 344915 | 3' UTR | 77 | 4351 | agtcagatgtctgggtggtc | 143 |
| 347239 | 344916 | 3' UTR | 77 | 4367 | gtggcacagagccattagtc | 144 |
| 347240 | 344917 | 3' UTR | 77 | 4548 | tcctaagggttaagatttga | 145 |
| 347241 | 344918 | 3' UTR | 77 | 4599 | tgaaacatctcaacttccag | 146 |
| 347242 | 344919 | 3' UTR | 77 | 4651 | gagcagaaaatttattcttt | 147 |
| 347243 | 344920 | 3' UTR | 77 | 4670 | tacacactaaactcatcgtg | 148 |
| 347244 | 344921 | 3' UTR | 77 | 4865 | catggatttactgagggcag | 149 |

TABLE 18-continued

| dsRNAs targeted to human kinesin-like 1 | | | | | | |
|---|---|---|---|---|---|---|
| ISIS # of antisense strand | Corresponds to sequence of | Region | Target SEQ ID NO | Target site | Sequence | SEQ ID NO |
| 347245 | 344922 | 3' UTR | 77 | 4973 | ttattaaccatggatttact | 150 |
| 347246 | 344923 | Coding; Exon 1a:Exon 20 junction | 78 | 286 | ggtgtcgtaccaccacctgg | 151 |
| 347247 | 344924 | Intron 9 | 76 | 28230 | aaagcctactaggttaatca | 152 |
| 347248 | 344925 | Intron 10 | 76 | 28736 | tggaaattaactccatagcc | 153 |
| 347249 | 344926 | Coding; Exon 6:Exon 22a junction | 79 | 542 | agggatacaactagagtatg | 154 |

The compounds in Table 18 are tested for their effects on human kinesin-like 1 expression in A549 cells. A549 cells are treated with oligonucleotide mixed with LIPOFECTIN (Invitrogen Corporation, Carlsbad, Calif.) as described herein. Cells are treated with oligonucleotide for 4 hours and harvested an additional 16 hours later. Untreated cells serve as a control. Human kinesin-like 1 mRNA expression levels are quantitated by real-time PCR as in other examples herein.

What is claimed is:

1. A compound comprising a modified oligonucleotide consisting of 12 to 30 linked nucleosides and having a nucleobase sequence comprising a portion of at least 8 contiguous nucleobases complementary to an equal length portion of nucleobases 528 to 555 of SEQ ID NO: 3, and wherein the nucleobase sequence of the modified oligonucleotide is at least 90% complementary to SEQ ID NO: 3.

2. The compound of claim 1, wherein the modified oligonucleotide is at least 95% complementary to SEQ ID NO: 3.

3. The compound of claim 2, wherein the modified oligonucleotide is 100% complementary to SEQ ID NO: 3.

4. The compound of claim 3, wherein the modified oligonucleotide hybridizes exclusively within nucleobases 528 to 555.

5. The compound of claim 1, consisting of a single-stranded modified oligonucleotide.

6. The compound of claim 5, comprising at least one modified internucleoside linkage.

7. The compound of claim 6, wherein each modified internucleoside linkage is a phosphorothioate internucleoside linkage.

8. The compound of claim 5, wherein at least one nucleoside comprises a modified sugar.

9. The compound of claim 8, wherein the at least one modified sugar is a bicyclic sugar.

10. The compound of claim 8, wherein the at least one modified sugar comprises a 2'-O-methoxyethyl.

11. The compound of claim 5, wherein at least one nucleoside comprises a modified nucleobase.

12. The compound of claim 11, wherein the modified nucleobase is a 5-methylcytosine.

13. The compound of claim 1, wherein the modified oligonucleotide comprises:

a gap segment consisting of linked deoxynucleosides;

a 5' wing segment consisting of linked nueleosides;

a 3' wing segment consisting of linked nucleosides;

wherein the gap segment is positioned between the 5' wing segment and the 3' wing segment and wherein each nucleoside of each wing segment comprises a modified sugar.

14. The compound of claim 13, wherein the modified oligonucleotide comprises:

a gap segment consisting of ten linked nucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyehtyl sugar; and wherein each internucleoside linkage is a phosphorothioate linkage.

15. The compound of claim 14, wherein the modified oligonucleotide consists of 20 linked nucleosides.

16. A composition comprising a modified oligonucleotide consisting of 12 to 30 linked nucleosides and having a nucleobase sequence comprising a portion of at least 8 contiguous nucleobases complementary to an equal length portion of nucleobases 528 to 555 of SEQ ID NO: 3, and wherein the nucleobase sequence of the modified oligonucleotide is at least 90% complementary to SEQ ID NO: 3, or a salt thereof, and a pharmaceutically acceptable carrier or diluent.

17. The composition of claim 16, wherein the modified oligonucleotide consists of 20 linked nucleosides.

18. A method comprising administering to a human a modified oligonucleotide consisting of 12 to 30 linked nucleosides and having a nucleobase sequence comprising a portion of at least 8 contiguous nuelcobases complementary to an equal length portion of nucleobases 528 to 555 of SEQ ID NO: 3, and wherein the nucleobase sequence of the modified oligonucleotide is at least 90% complementary to SEQ ID NO: 3.

19. The method of claim 18, wherein administering the compound to the human treats a hyperproliferative disorder.

* * * * *

```
                              SEQUENCE LISTING

<160> NUMBER OF SEQ ID NOS: 241

<210> SEQ ID NO 1
<211> LENGTH: 20
<212> TYPE: DNA
<213> ORGANISM: Homo sapiens

<400> SEQUENCE: 1

tccgtcatcg ctcctcaggg                                                  20


<210> SEQ ID NO 2
<211> LENGTH: 20
<212> TYPE: DNA
<213> ORGANISM: Homo sapiens

<400> SEQUENCE: 2

atgcattctg cccccaagga                                                  20


<210> SEQ ID NO 3
<211> LENGTH: 3741
<212> TYPE: DNA
<213> ORGANISM: Homo sapiens
<220> FEATURE:
<221> NAME/KEY: CDS
<222> LOCATION: (11)...(3184)

<400> SEQUENCE: 3

gaattccgtc atg gcg tcg cag cca aat tcg tct gcg aag aag aaa gag         49
           Met Ala Ser Gln Pro Asn Ser Ser Ala Lys Lys Lys Glu
             1               5                  10

gag aag ggg aag aac atc cag gtg gtg gtg aga tgc aga cca ttt aat         97
Glu Lys Gly Lys Asn Ile Gln Val Val Val Arg Cys Arg Pro Phe Asn
     15                  20                  25

ttg gca gag cgg aaa gct agc gcc cat tca ata gta gaa tgt gat cct        145
Leu Ala Glu Arg Lys Ala Ser Ala His Ser Ile Val Glu Cys Asp Pro
 30                  35                  40                  45

gta cga aaa gaa gtt agt gta cga act gga gga ttg gct gac aag agc        193
Val Arg Lys Glu Val Ser Val Arg Thr Gly Gly Leu Ala Asp Lys Ser
                 50                  55                  60

tca agg aaa aca tac act ttt gat atg gtg ttt gga gca tct act aaa        241
```

-continued

```
Ser Arg Lys Thr Tyr Thr Phe Asp Met Val Phe Gly Ala Ser Thr Lys
            65                  70                  75

cag att gat gtt tac cga agt gtt gtt tgt cca att ctg gat gaa gtt      289
Gln Ile Asp Val Tyr Arg Ser Val Val Cys Pro Ile Leu Asp Glu Val
        80                  85                  90

att atg ggc tat aat tgc act atc ttt gcg tat ggc caa act ggc act      337
Ile Met Gly Tyr Asn Cys Thr Ile Phe Ala Tyr Gly Gln Thr Gly Thr
    95                  100                 105

gga aaa act ttt aca atg gaa ggt gaa agg tca cct aat gaa gag tat      385
Gly Lys Thr Phe Thr Met Glu Gly Glu Arg Ser Pro Asn Glu Glu Tyr
110                 115                 120                 125

acc tgg gaa gag gat ccc ttg gct ggt ata att cca cgt acc ctt cat      433
Thr Trp Glu Glu Asp Pro Leu Ala Gly Ile Ile Pro Arg Thr Leu His
                130                 135                 140

caa att ttt gag aaa ctt act gat aat ggt act gaa ttt tca gtc aaa      481
Gln Ile Phe Glu Lys Leu Thr Asp Asn Gly Thr Glu Phe Ser Val Lys
            145                 150                 155

gtg tct ctg ttg gag atc tat aat gaa gag ctt ttt gat ctt ctt aat      529
Val Ser Leu Leu Glu Ile Tyr Asn Glu Glu Leu Phe Asp Leu Leu Asn
        160                 165                 170

cca tca tct gat gtt tct gag aga cta cag atg ttt gat gat ccc cgt      577
Pro Ser Ser Asp Val Ser Glu Arg Leu Gln Met Phe Asp Asp Pro Arg
    175                 180                 185

aac aag aga gga gtg ata att aaa ggt tta gaa gaa att aca gta cac      625
Asn Lys Arg Gly Val Ile Ile Lys Gly Leu Glu Glu Ile Thr Val His
190                 195                 200                 205

aac aag gat gaa gtc tat caa att tta gaa aag ggg gca gca aaa agg      673
Asn Lys Asp Glu Val Tyr Gln Ile Leu Glu Lys Gly Ala Ala Lys Arg
                210                 215                 220

aca act gca gct act ctg atg aat gca tac tct agt cgt tcc cac tca      721
Thr Thr Ala Ala Thr Leu Met Asn Ala Tyr Ser Ser Arg Ser His Ser
            225                 230                 235

gtt ttc tct gtt aca ata cat atg aaa gaa act acg att gat gga gaa      769
Val Phe Ser Val Thr Ile His Met Lys Glu Thr Thr Ile Asp Gly Glu
        240                 245                 250

gag ctt gtt aaa atc gga aag ttg aac ttg gtt gat ctt gca gga agt      817
Glu Leu Val Lys Ile Gly Lys Leu Asn Leu Val Asp Leu Ala Gly Ser
    255                 260                 265

gaa aac att ggc cgt tct gga gct gtt gat aag aga gct cgg gaa gct      865
Glu Asn Ile Gly Arg Ser Gly Ala Val Asp Lys Arg Ala Arg Glu Ala
270                 275                 280                 285

gga aat ata aat caa tcc ctg ttg act ttg gga agg gtc att act gcc      913
Gly Asn Ile Asn Gln Ser Leu Leu Thr Leu Gly Arg Val Ile Thr Ala
                290                 295                 300

ctt gta gaa aga aca cct cat gtt cct tat cga gaa tct aaa cta act      961
Leu Val Glu Arg Thr Pro His Val Pro Tyr Arg Glu Ser Lys Leu Thr
            305                 310                 315

aga atc ctc cag gat tct ctt gga ggg cgt aca aga aca tct ata att     1009
Arg Ile Leu Gln Asp Ser Leu Gly Gly Arg Thr Arg Thr Ser Ile Ile
        320                 325                 330

gca aca att tct cct gca tct ctc aat ctt gag gaa act ctg agt aca     1057
Ala Thr Ile Ser Pro Ala Ser Leu Asn Leu Glu Glu Thr Leu Ser Thr
    335                 340                 345

ttg gaa tat gct cat aga gca aag aac ata ttg aat aag cct gaa gtg     1105
Leu Glu Tyr Ala His Arg Ala Lys Asn Ile Leu Asn Lys Pro Glu Val
350                 355                 360                 365

aat cag aaa ctc acc aaa aaa gct ctt att aag gag tat acg gag gag     1153
Asn Gln Lys Leu Thr Lys Lys Ala Leu Ile Lys Glu Tyr Thr Glu Glu
                370                 375                 380
```

-continued

```
ata gaa cgt tta aaa cga gat ctt gct gca gcc cgt gag aaa aat gga      1201
Ile Glu Arg Leu Lys Arg Asp Leu Ala Ala Ala Arg Glu Lys Asn Gly
            385                 390                 395

gtg tat att tct gaa gaa aat ttt aga gtc atg agt gga aaa tta act      1249
Val Tyr Ile Ser Glu Glu Asn Phe Arg Val Met Ser Gly Lys Leu Thr
        400                 405                 410

gtt caa gaa gag cag att gta gaa ttg att gaa aaa att ggt gct gtt      1297
Val Gln Glu Glu Gln Ile Val Glu Leu Ile Glu Lys Ile Gly Ala Val
    415                 420                 425

gag gag gag ctg aat agg gtt aca gag ttg ttt atg gat aat aaa aat      1345
Glu Glu Glu Leu Asn Arg Val Thr Glu Leu Phe Met Asp Asn Lys Asn
430                 435                 440                 445

gaa ctt gac cag tgt aaa tct gac ctg caa aat aaa aca caa gaa ctt      1393
Glu Leu Asp Gln Cys Lys Ser Asp Leu Gln Asn Lys Thr Gln Glu Leu
                450                 455                 460

gaa acc act caa aaa cat ttg caa gaa act aaa tta caa ctt gtt aaa      1441
Glu Thr Thr Gln Lys His Leu Gln Glu Thr Lys Leu Gln Leu Val Lys
            465                 470                 475

gaa gaa tat atc aca tca gct ttg gaa agt act gag gag aaa ctt cat      1489
Glu Glu Tyr Ile Thr Ser Ala Leu Glu Ser Thr Glu Glu Lys Leu His
        480                 485                 490

gat gct gcc agc aag ctg ctt aac aca gtt gaa gaa act aca aaa gat      1537
Asp Ala Ala Ser Lys Leu Leu Asn Thr Val Glu Glu Thr Thr Lys Asp
    495                 500                 505

gta tct ggt ctc cat tcc aaa ctg gat cgt aag aag gca gtt gac caa      1585
Val Ser Gly Leu His Ser Lys Leu Asp Arg Lys Lys Ala Val Asp Gln
510                 515                 520                 525

cac aat gca gaa gct cag gat att ttt ggc aaa aac ctg aat agt ctg      1633
His Asn Ala Glu Ala Gln Asp Ile Phe Gly Lys Asn Leu Asn Ser Leu
                530                 535                 540

ttt aat aat atg gaa gaa tta att aag gat ggc agc tca aag caa aag      1681
Phe Asn Asn Met Glu Glu Leu Ile Lys Asp Gly Ser Ser Lys Gln Lys
            545                 550                 555

gcc atg cta gaa gta cat aag acc tta ttt ggt aat ctg ctg tct tcc      1729
Ala Met Leu Glu Val His Lys Thr Leu Phe Gly Asn Leu Leu Ser Ser
        560                 565                 570

agt gtc tct gca tta gat acc att act aca gta gca ctt gga tct ctc      1777
Ser Val Ser Ala Leu Asp Thr Ile Thr Thr Val Ala Leu Gly Ser Leu
    575                 580                 585

aca tct att cca gaa aat gtg tct act cat gtt tct cag att ttt aat      1825
Thr Ser Ile Pro Glu Asn Val Ser Thr His Val Ser Gln Ile Phe Asn
590                 595                 600                 605

atg ata cta aaa gaa caa tca tta gca gca gaa agt aaa act gta cta      1873
Met Ile Leu Lys Glu Gln Ser Leu Ala Ala Glu Ser Lys Thr Val Leu
                610                 615                 620

cag gaa ttg att aat gta ctc aag act gat ctt cta agt tca ctg gaa      1921
Gln Glu Leu Ile Asn Val Leu Lys Thr Asp Leu Leu Ser Ser Leu Glu
            625                 630                 635

atg att tta tcc cca act gtg gtg tct ata ctg aaa atc aat agt caa      1969
Met Ile Leu Ser Pro Thr Val Val Ser Ile Leu Lys Ile Asn Ser Gln
        640                 645                 650

cta aag cat att ttc aag act tca ttg aca gtg gcc gat aag ata gaa      2017
Leu Lys His Ile Phe Lys Thr Ser Leu Thr Val Ala Asp Lys Ile Glu
    655                 660                 665

gat caa aaa aaa agg aac tca gat ggc ttt ctc agt ata ctg tgt aac      2065
Asp Gln Lys Lys Arg Asn Ser Asp Gly Phe Leu Ser Ile Leu Cys Asn
670                 675                 680                 685

aat cta cat gaa cta caa gaa aat acc att tgt tcc ttg gtt gag tca      2113
Asn Leu His Glu Leu Gln Glu Asn Thr Ile Cys Ser Leu Val Glu Ser
                690                 695                 700
```

-continued

```
caa aag caa tgt gga aac cta act gaa gac ctg aag aca ata aag cag     2161
Gln Lys Gln Cys Gly Asn Leu Thr Glu Asp Leu Lys Thr Ile Lys Gln
            705                 710                 715

acc cat tcc cag gaa ctt tgc aag tta atg aat ctt tgg aca gag aga     2209
Thr His Ser Gln Glu Leu Cys Lys Leu Met Asn Leu Trp Thr Glu Arg
        720                 725                 730

ttc tgt gct ttg gag gaa aag tgt gaa aat ata cag aaa cca ctt agt     2257
Phe Cys Ala Leu Glu Glu Lys Cys Glu Asn Ile Gln Lys Pro Leu Ser
    735                 740                 745

agt gtc cag gaa aat ata cag cag aaa tct aag gat ata gtc aac aaa     2305
Ser Val Gln Glu Asn Ile Gln Gln Lys Ser Lys Asp Ile Val Asn Lys
750                 755                 760                 765

atg act ttt cac agt caa aaa ttt tgt gct gat tct gat ggc ttc tca     2353
Met Thr Phe His Ser Gln Lys Phe Cys Ala Asp Ser Asp Gly Phe Ser
                770                 775                 780

cag gaa ctc aga aat ttt aac caa gaa ggt aca aaa ttg gtt gaa gaa     2401
Gln Glu Leu Arg Asn Phe Asn Gln Glu Gly Thr Lys Leu Val Glu Glu
            785                 790                 795

tct gtg aaa cac tct gat aaa ctc aat ggc aac ctg gaa aaa ata tct     2449
Ser Val Lys His Ser Asp Lys Leu Asn Gly Asn Leu Glu Lys Ile Ser
        800                 805                 810

caa gag act gaa cag aga tgt gaa tct ctg aac aca aga aca gtt tat     2497
Gln Glu Thr Glu Gln Arg Cys Glu Ser Leu Asn Thr Arg Thr Val Tyr
    815                 820                 825

ttt tct gaa cag tgg gta tct tcc tta aat gaa agg gaa cag gaa ctt     2545
Phe Ser Glu Gln Trp Val Ser Ser Leu Asn Glu Arg Glu Gln Glu Leu
830                 835                 840                 845

cac aac tta ttg gag gtt gta agc caa tgt tgt gag gct tca agt tca     2593
His Asn Leu Leu Glu Val Val Ser Gln Cys Cys Glu Ala Ser Ser Ser
                850                 855                 860

gac atc act gag aaa tca gat gga cgt aag gca gct cat gag aaa cag     2641
Asp Ile Thr Glu Lys Ser Asp Gly Arg Lys Ala Ala His Glu Lys Gln
            865                 870                 875

cat aac att ttt ctt gat cag atg act att gat gaa gat aaa ttg ata     2689
His Asn Ile Phe Leu Asp Gln Met Thr Ile Asp Glu Asp Lys Leu Ile
        880                 885                 890

gca caa aat cta gaa ctt aat gaa acc ata aaa att ggt ttg act aag     2737
Ala Gln Asn Leu Glu Leu Asn Glu Thr Ile Lys Ile Gly Leu Thr Lys
    895                 900                 905

ctt aat tgc ttt ctg gaa cag gat ctg aaa ctg gat atc cca aca ggt     2785
Leu Asn Cys Phe Leu Glu Gln Asp Leu Lys Leu Asp Ile Pro Thr Gly
910                 915                 920                 925

acg aca cca cag agg aaa agt tat tta tac cca tca aca ctg gta aga     2833
Thr Thr Pro Gln Arg Lys Ser Tyr Leu Tyr Pro Ser Thr Leu Val Arg
                930                 935                 940

act gaa cca cgt gaa cat ctc ctt gat cag ctg aaa agg aaa cag cct     2881
Thr Glu Pro Arg Glu His Leu Leu Asp Gln Leu Lys Arg Lys Gln Pro
            945                 950                 955

gag ctg tta atg atg cta aac tgt tca gaa aac aac aaa gaa gag aca     2929
Glu Leu Leu Met Met Leu Asn Cys Ser Glu Asn Asn Lys Glu Glu Thr
        960                 965                 970

att ccg gat gtg gat gta gaa gag gca gtt ctg ggg cag tat act gaa     2977
Ile Pro Asp Val Asp Val Glu Glu Ala Val Leu Gly Gln Tyr Thr Glu
    975                 980                 985

gaa cct cta agt caa gag cca tct gta gat gct ggt gtg gat tgt tca     3025
Glu Pro Leu Ser Gln Glu Pro Ser Val Asp Ala Gly Val Asp Cys Ser
 990                 995                 1000                1005

tca att ggc ggg gtt cca ttt ttc cag cat aaa aaa tca cat gga aaa     3073
Ser Ile Gly Gly Val Pro Phe Phe Gln His Lys Lys Ser His Gly Lys
```

-continued

```
             1010              1015              1020

gac aaa gaa aac aga ggc att aac aca ctg gag agg tct aaa gtg gaa     3121
Asp Lys Glu Asn Arg Gly Ile Asn Thr Leu Glu Arg Ser Lys Val Glu
            1025              1030              1035

gaa act aca gag cac ttg gtt aca aag agc aga tta cct ctg cga gcc     3169
Glu Thr Thr Glu His Leu Val Thr Lys Ser Arg Leu Pro Leu Arg Ala
        1040              1045              1050

cag atc aac ctt taa ttcacttggg ggttggcaat tttattttta aagaaaaact     3224
Gln Ile Asn Leu  *
    1055

taaaaataaa acctgaaacc ccagaacttg agccttgtgt atagatttta aaagaatata   3284

tatatcagcc gggcgcgtgg ctctagctgt aatcccagct aactttggag gctgaggcgg   3344

gtggattgct tgagcccagg agtttgagac cagcctggcc aacgtgcgct aaaaccttcg   3404

tctctgttaa aaattagccg ggcgtggtgg gcacactcct gtaatcccag ctactgggga   3464

ggctgaggca cgagaatcac ttgaacccag aagcggggtt gcagtgagcc aaaggtacac   3524

cactacactc cagcctgggc aacagagcaa gactcggtct caaaaataaa atttaaaaaa   3584

gatataaggc agtactgtaa attcagttga attttgatat ctacccattt ttctgtcatc   3644

cctatagttc actttgtatt aaattgggtt tcatttggga tttgcaatgt aaatacgtat   3704

ttctagtttt catataaagt agttctttta ggaattc                            3741


<210> SEQ ID NO 4
<211> LENGTH: 1057
<212> TYPE: PRT
<213> ORGANISM: Homo sapiens

<400> SEQUENCE: 4

Met Ala Ser Gln Pro Asn Ser Ser Ala Lys Lys Lys Glu Glu Lys Gly
 1               5                  10                  15

Lys Asn Ile Gln Val Val Val Arg Cys Arg Pro Phe Asn Leu Ala Glu
            20                  25                  30

Arg Lys Ala Ser Ala His Ser Ile Val Glu Cys Asp Pro Val Arg Lys
        35                  40                  45

Glu Val Ser Val Arg Thr Gly Gly Leu Ala Asp Lys Ser Ser Arg Lys
    50                  55                  60

Thr Tyr Thr Phe Asp Met Val Phe Gly Ala Ser Thr Lys Gln Ile Asp
65                  70                  75                  80

Val Tyr Arg Ser Val Val Cys Pro Ile Leu Asp Glu Val Ile Met Gly
                85                  90                  95

Tyr Asn Cys Thr Ile Phe Ala Tyr Gly Gln Thr Gly Thr Gly Lys Thr
            100                 105                 110

Phe Thr Met Glu Gly Glu Arg Ser Pro Asn Glu Glu Tyr Thr Trp Glu
        115                 120                 125

Glu Asp Pro Leu Ala Gly Ile Ile Pro Arg Thr Leu His Gln Ile Phe
    130                 135                 140

Glu Lys Leu Thr Asp Asn Gly Thr Glu Phe Ser Val Lys Val Ser Leu
145                 150                 155                 160

Leu Glu Ile Tyr Asn Glu Glu Leu Phe Asp Leu Leu Asn Pro Ser Ser
                165                 170                 175

Asp Val Ser Glu Arg Leu Gln Met Phe Asp Asp Pro Arg Asn Lys Arg
            180                 185                 190

Gly Val Ile Ile Lys Gly Leu Glu Glu Ile Thr Val His Asn Lys Asp
        195                 200                 205
```

-continued

```
Glu Val Tyr Gln Ile Leu Glu Lys Gly Ala Ala Lys Arg Thr Thr Ala
    210                 215                 220

Ala Thr Leu Met Asn Ala Tyr Ser Ser Arg Ser His Ser Val Phe Ser
225                 230                 235                 240

Val Thr Ile His Met Lys Glu Thr Thr Ile Asp Gly Glu Glu Leu Val
                245                 250                 255

Lys Ile Gly Lys Leu Asn Leu Val Asp Leu Ala Gly Ser Glu Asn Ile
            260                 265                 270

Gly Arg Ser Gly Ala Val Asp Lys Arg Ala Arg Glu Ala Gly Asn Ile
        275                 280                 285

Asn Gln Ser Leu Leu Thr Leu Gly Arg Val Ile Thr Ala Leu Val Glu
    290                 295                 300

Arg Thr Pro His Val Pro Tyr Arg Glu Ser Lys Leu Thr Arg Ile Leu
305                 310                 315                 320

Gln Asp Ser Leu Gly Gly Arg Thr Arg Thr Ser Ile Ile Ala Thr Ile
                325                 330                 335

Ser Pro Ala Ser Leu Asn Leu Glu Glu Thr Leu Ser Thr Leu Glu Tyr
            340                 345                 350

Ala His Arg Ala Lys Asn Ile Leu Asn Lys Pro Glu Val Asn Gln Lys
        355                 360                 365

Leu Thr Lys Lys Ala Leu Ile Lys Glu Tyr Thr Glu Glu Ile Glu Arg
    370                 375                 380

Leu Lys Arg Asp Leu Ala Ala Ala Arg Glu Lys Asn Gly Val Tyr Ile
385                 390                 395                 400

Ser Glu Glu Asn Phe Arg Val Met Ser Gly Lys Leu Thr Val Gln Glu
                405                 410                 415

Glu Gln Ile Val Glu Leu Ile Glu Lys Ile Gly Ala Val Glu Glu Glu
            420                 425                 430

Leu Asn Arg Val Thr Glu Leu Phe Met Asp Asn Lys Asn Glu Leu Asp
        435                 440                 445

Gln Cys Lys Ser Asp Leu Gln Asn Lys Thr Gln Glu Leu Glu Thr Thr
    450                 455                 460

Gln Lys His Leu Gln Glu Thr Lys Leu Gln Leu Val Lys Glu Glu Tyr
465                 470                 475                 480

Ile Thr Ser Ala Leu Glu Ser Thr Glu Glu Lys Leu His Asp Ala Ala
                485                 490                 495

Ser Lys Leu Leu Asn Thr Val Glu Glu Thr Thr Lys Asp Val Ser Gly
            500                 505                 510

Leu His Ser Lys Leu Asp Arg Lys Lys Ala Val Asp Gln His Asn Ala
        515                 520                 525

Glu Ala Gln Asp Ile Phe Gly Lys Asn Leu Asn Ser Leu Phe Asn Asn
    530                 535                 540

Met Glu Glu Leu Ile Lys Asp Gly Ser Ser Lys Gln Lys Ala Met Leu
545                 550                 555                 560

Glu Val His Lys Thr Leu Phe Gly Asn Leu Leu Ser Ser Ser Val Ser
                565                 570                 575

Ala Leu Asp Thr Ile Thr Thr Val Ala Leu Gly Ser Leu Thr Ser Ile
            580                 585                 590

Pro Glu Asn Val Ser Thr His Val Ser Gln Ile Phe Asn Met Ile Leu
        595                 600                 605

Lys Glu Gln Ser Leu Ala Ala Glu Ser Lys Thr Val Leu Gln Glu Leu
    610                 615                 620

Ile Asn Val Leu Lys Thr Asp Leu Leu Ser Ser Leu Glu Met Ile Leu
```

-continued

```
625                 630                 635                 640

Ser Pro Thr Val Val Ser Ile Leu Lys Ile Asn Ser Gln Leu Lys His
                645                 650                 655

Ile Phe Lys Thr Ser Leu Thr Val Ala Asp Lys Ile Glu Asp Gln Lys
            660                 665                 670

Lys Arg Asn Ser Asp Gly Phe Leu Ser Ile Leu Cys Asn Asn Leu His
        675                 680                 685

Glu Leu Gln Glu Asn Thr Ile Cys Ser Leu Val Glu Ser Gln Lys Gln
    690                 695                 700

Cys Gly Asn Leu Thr Glu Asp Leu Lys Thr Ile Lys Gln Thr His Ser
705                 710                 715                 720

Gln Glu Leu Cys Lys Leu Met Asn Leu Trp Thr Glu Arg Phe Cys Ala
                725                 730                 735

Leu Glu Glu Lys Cys Glu Asn Ile Gln Lys Pro Leu Ser Ser Val Gln
            740                 745                 750

Glu Asn Ile Gln Gln Lys Ser Lys Asp Ile Val Asn Lys Met Thr Phe
        755                 760                 765

His Ser Gln Lys Phe Cys Ala Asp Ser Asp Gly Phe Ser Gln Glu Leu
    770                 775                 780

Arg Asn Phe Asn Gln Glu Gly Thr Lys Leu Val Glu Glu Ser Val Lys
785                 790                 795                 800

His Ser Asp Lys Leu Asn Gly Asn Leu Glu Lys Ile Ser Gln Glu Thr
                805                 810                 815

Glu Gln Arg Cys Glu Ser Leu Asn Thr Arg Thr Val Tyr Phe Ser Glu
            820                 825                 830

Gln Trp Val Ser Ser Leu Asn Glu Arg Glu Gln Glu Leu His Asn Leu
        835                 840                 845

Leu Glu Val Val Ser Gln Cys Cys Glu Ala Ser Ser Ser Asp Ile Thr
    850                 855                 860

Glu Lys Ser Asp Gly Arg Lys Ala Ala His Glu Lys Gln His Asn Ile
865                 870                 875                 880

Phe Leu Asp Gln Met Thr Ile Asp Glu Asp Lys Leu Ile Ala Gln Asn
                885                 890                 895

Leu Glu Leu Asn Glu Thr Ile Lys Ile Gly Leu Thr Lys Leu Asn Cys
            900                 905                 910

Phe Leu Glu Gln Asp Leu Lys Leu Asp Ile Pro Thr Gly Thr Thr Pro
        915                 920                 925

Gln Arg Lys Ser Tyr Leu Tyr Pro Ser Thr Leu Val Arg Thr Glu Pro
    930                 935                 940

Arg Glu His Leu Leu Asp Gln Leu Lys Arg Lys Gln Pro Glu Leu Leu
945                 950                 955                 960

Met Met Leu Asn Cys Ser Glu Asn Asn Lys Glu Glu Thr Ile Pro Asp
                965                 970                 975

Val Asp Val Glu Glu Ala Val Leu Gly Gln Tyr Thr Glu Glu Pro Leu
            980                 985                 990

Ser Gln Glu Pro Ser Val Asp Ala Gly Val Asp Cys Ser Ser Ile Gly
        995                 1000                1005

Gly Val Pro Phe Phe Gln His Lys Lys Ser His Gly Lys Asp Lys Glu
    1010                1015                1020

Asn Arg Gly Ile Asn Thr Leu Glu Arg Ser Lys Val Glu Glu Thr Thr
1025                1030                1035                1040

Glu His Leu Val Thr Lys Ser Arg Leu Pro Leu Arg Ala Gln Ile Asn
                1045                1050                1055
```

Leu

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
gtggtgagat gcagaccatt taat 24

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
cttttcgtac aggatcacat tctactattg 30

<210> SEQ ID NO 7
<211> LENGTH: 22
<212> TYPE: DNA
<213> ORGANISM: Artificial Sequence
<220> FEATURE:
<223> OTHER INFORMATION: Probe

<400> SEQUENCE: 7
tggcagagcg gaaagctagc gc 22

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
gaaggtgaag gtcggagtc 19

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gaagatggtg atgggatttc 20

<210> SEQ ID NO 10
<211> LENGTH: 20
<212> TYPE: DNA
<213> ORGANISM: Artificial Sequence
<220> FEATURE:
<223> OTHER INFORMATION: Probe

<400> SEQUENCE: 10
caagcttccc gttctcagcc 20

<210> SEQ ID NO 11
<211> LENGTH: 20
<212> TYPE: DNA

<213> ORGANISM: Homo sapiens

<400> SEQUENCE: 11
tgttgactat atccttagat 20

<210> SEQ ID NO 12
<211> LENGTH: 20
<212> TYPE: DNA
<213> ORGANISM: Homo sapiens

<400> SEQUENCE: 12
tctgctgcta atgattgttc 20

<210> SEQ ID NO 13
<211> LENGTH: 20
<212> TYPE: DNA
<213> ORGANISM: Homo sapiens

<400> SEQUENCE: 13
ctggaataga tgtgagagat 20

<210> SEQ ID NO 14
<211> LENGTH: 20
<212> TYPE: DNA
<213> ORGANISM: Homo sapiens

<400> SEQUENCE: 14
aaagtcaaca gggattgatt 20

<210> SEQ ID NO 15
<211> LENGTH: 20
<212> TYPE: DNA
<213> ORGANISM: Homo sapiens

<400> SEQUENCE: 15
gatcaagaaa aatgttatgc 20

<210> SEQ ID NO 16
<211> LENGTH: 20
<212> TYPE: DNA
<213> ORGANISM: Homo sapiens

<400> SEQUENCE: 16
atccaagtgc tactgtagta 20

<210> SEQ ID NO 17
<211> LENGTH: 20
<212> TYPE: DNA
<213> ORGANISM: Homo sapiens

<400> SEQUENCE: 17
tttcctcaag attgagagat 20

<210> SEQ ID NO 18
<211> LENGTH: 20
<212> TYPE: DNA
<213> ORGANISM: Homo sapiens

<400> SEQUENCE: 18
caaagcacag aatctctctg 20

<210> SEQ ID NO 19
<211> LENGTH: 20

<212> TYPE: DNA
<213> ORGANISM: Homo sapiens

<400> SEQUENCE: 19
cattaacttg caaagttcct 20

<210> SEQ ID NO 20
<211> LENGTH: 20
<212> TYPE: DNA
<213> ORGANISM: Homo sapiens

<400> SEQUENCE: 20
atccagtttg gaatggagac 20

<210> SEQ ID NO 21
<211> LENGTH: 20
<212> TYPE: DNA
<213> ORGANISM: Homo sapiens

<400> SEQUENCE: 21
ttagcatcat taacagctca 20

<210> SEQ ID NO 22
<211> LENGTH: 20
<212> TYPE: DNA
<213> ORGANISM: Homo sapiens

<400> SEQUENCE: 22
taaacaactc tgtaacccta 20

<210> SEQ ID NO 23
<211> LENGTH: 20
<212> TYPE: DNA
<213> ORGANISM: Homo sapiens

<400> SEQUENCE: 23
agaaacatca gatgatggat 20

<210> SEQ ID NO 24
<211> LENGTH: 20
<212> TYPE: DNA
<213> ORGANISM: Homo sapiens

<400> SEQUENCE: 24
agtgaactta gaagatcagt 20

<210> SEQ ID NO 25
<211> LENGTH: 20
<212> TYPE: DNA
<213> ORGANISM: Homo sapiens

<400> SEQUENCE: 25
ttcagctgat caaggagatg 20

<210> SEQ ID NO 26
<211> LENGTH: 20
<212> TYPE: DNA
<213> ORGANISM: Homo sapiens

<400> SEQUENCE: 26
ccgagctctc ttatcaacag 20

<210> SEQ ID NO 27

<211> LENGTH: 20
<212> TYPE: DNA
<213> ORGANISM: Homo sapiens

<400> SEQUENCE: 27
agcttctgca ttgtgttggt 20

<210> SEQ ID NO 28
<211> LENGTH: 20
<212> TYPE: DNA
<213> ORGANISM: Homo sapiens

<400> SEQUENCE: 28
attcaactga atttacagta 20

<210> SEQ ID NO 29
<211> LENGTH: 20
<212> TYPE: DNA
<213> ORGANISM: Homo sapiens

<400> SEQUENCE: 29
cagaggtaat ctgctctttg 20

<210> SEQ ID NO 30
<211> LENGTH: 20
<212> TYPE: DNA
<213> ORGANISM: Homo sapiens

<400> SEQUENCE: 30
acactggtca agttcatttt 20

<210> SEQ ID NO 31
<211> LENGTH: 20
<212> TYPE: DNA
<213> ORGANISM: Homo sapiens

<400> SEQUENCE: 31
cagtactttc caaagctgat 20

<210> SEQ ID NO 32
<211> LENGTH: 20
<212> TYPE: DNA
<213> ORGANISM: Homo sapiens

<400> SEQUENCE: 32
cagttaggtt tccacattgc 20

<210> SEQ ID NO 33
<211> LENGTH: 20
<212> TYPE: DNA
<213> ORGANISM: Homo sapiens

<400> SEQUENCE: 33
ctactttata tgaaaactag 20

<210> SEQ ID NO 34
<211> LENGTH: 20
<212> TYPE: DNA
<213> ORGANISM: Homo sapiens

<400> SEQUENCE: 34
atgagcatat tccaatgtac 20

-continued

<210> SEQ ID NO 35
<211> LENGTH: 20
<212> TYPE: DNA
<213> ORGANISM: Homo sapiens

<400> SEQUENCE: 35
agtctctcag aaacatcaga 20

<210> SEQ ID NO 36
<211> LENGTH: 20
<212> TYPE: DNA
<213> ORGANISM: Homo sapiens

<400> SEQUENCE: 36
taccagccaa gggatcctct 20

<210> SEQ ID NO 37
<211> LENGTH: 20
<212> TYPE: DNA
<213> ORGANISM: Homo sapiens

<400> SEQUENCE: 37
ttcattatag atctccaaca 20

<210> SEQ ID NO 38
<211> LENGTH: 20
<212> TYPE: DNA
<213> ORGANISM: Homo sapiens

<400> SEQUENCE: 38
ttaaacagac tattcaggtt 20

<210> SEQ ID NO 39
<211> LENGTH: 20
<212> TYPE: DNA
<213> ORGANISM: Homo sapiens

<400> SEQUENCE: 39
tcttcagtat actgccccag 20

<210> SEQ ID NO 40
<211> LENGTH: 20
<212> TYPE: DNA
<213> ORGANISM: Homo sapiens

<400> SEQUENCE: 40
actgtgaaaa gtcattttgt 20

<210> SEQ ID NO 41
<211> LENGTH: 20
<212> TYPE: DNA
<213> ORGANISM: Homo sapiens

<400> SEQUENCE: 41
caagatctcg ttttaaacgt 20

<210> SEQ ID NO 42
<211> LENGTH: 20
<212> TYPE: DNA
<213> ORGANISM: Homo sapiens

<400> SEQUENCE: 42
tggccatacg caaagatagt 20

<210> SEQ ID NO 43
<211> LENGTH: 20
<212> TYPE: DNA
<213> ORGANISM: Homo sapiens

<400> SEQUENCE: 43
gctgtatatt ttcctggaca 20

<210> SEQ ID NO 44
<211> LENGTH: 20
<212> TYPE: DNA
<213> ORGANISM: Homo sapiens

<400> SEQUENCE: 44
ttgctttgag ctgccatcct 20

<210> SEQ ID NO 45
<211> LENGTH: 20
<212> TYPE: DNA
<213> ORGANISM: Homo sapiens

<400> SEQUENCE: 45
gagaagccat cagaatcagc 20

<210> SEQ ID NO 46
<211> LENGTH: 20
<212> TYPE: DNA
<213> ORGANISM: Homo sapiens

<400> SEQUENCE: 46
ctcaagattg agagatgcag 20

<210> SEQ ID NO 47
<211> LENGTH: 20
<212> TYPE: DNA
<213> ORGANISM: Homo sapiens

<400> SEQUENCE: 47
gtttctcatg agctgcctta 20

<210> SEQ ID NO 48
<211> LENGTH: 20
<212> TYPE: DNA
<213> ORGANISM: Homo sapiens

<400> SEQUENCE: 48
gaacaatcat tagcagcaga 20

<210> SEQ ID NO 49
<211> LENGTH: 20
<212> TYPE: DNA
<213> ORGANISM: Homo sapiens

<400> SEQUENCE: 49
atctctcaca tctattccag 20

<210> SEQ ID NO 50
<211> LENGTH: 20
<212> TYPE: DNA
<213> ORGANISM: Homo sapiens

<400> SEQUENCE: 50
aatcaatccc tgttgacttt 20

<210> SEQ ID NO 51
<211> LENGTH: 20
<212> TYPE: DNA
<213> ORGANISM: Homo sapiens

<400> SEQUENCE: 51
gcataacatt tttcttgatc 20

<210> SEQ ID NO 52
<211> LENGTH: 20
<212> TYPE: DNA
<213> ORGANISM: Homo sapiens

<400> SEQUENCE: 52
tactacagta gcacttggat 20

<210> SEQ ID NO 53
<211> LENGTH: 20
<212> TYPE: DNA
<213> ORGANISM: Homo sapiens

<400> SEQUENCE: 53
atctctcaat cttgaggaaa 20

<210> SEQ ID NO 54
<211> LENGTH: 20
<212> TYPE: DNA
<213> ORGANISM: Homo sapiens

<400> SEQUENCE: 54
cagagagatt ctgtgctttg 20

<210> SEQ ID NO 55
<211> LENGTH: 20
<212> TYPE: DNA
<213> ORGANISM: Homo sapiens

<400> SEQUENCE: 55
tgagctgtta atgatgctaa 20

<210> SEQ ID NO 56
<211> LENGTH: 20
<212> TYPE: DNA
<213> ORGANISM: Homo sapiens

<400> SEQUENCE: 56
atccatcatc tgatgtttct 20

<210> SEQ ID NO 57
<211> LENGTH: 20
<212> TYPE: DNA
<213> ORGANISM: Homo sapiens

<400> SEQUENCE: 57
actgatcttc taagttcact 20

<210> SEQ ID NO 58
<211> LENGTH: 20
<212> TYPE: DNA
<213> ORGANISM: Homo sapiens

<400> SEQUENCE: 58

-continued catctccttg atcagctgaa 20

<210> SEQ ID NO 59
<211> LENGTH: 20
<212> TYPE: DNA
<213> ORGANISM: Homo sapiens

<400> SEQUENCE: 59
ctgttgataa gagagctcgg 20

<210> SEQ ID NO 60
<211> LENGTH: 20
<212> TYPE: DNA
<213> ORGANISM: Homo sapiens

<400> SEQUENCE: 60
accaacacaa tgcagaagct 20

<210> SEQ ID NO 61
<211> LENGTH: 20
<212> TYPE: DNA
<213> ORGANISM: Homo sapiens

<400> SEQUENCE: 61
caaagagcag attacctctg 20

<210> SEQ ID NO 62
<211> LENGTH: 20
<212> TYPE: DNA
<213> ORGANISM: Homo sapiens

<400> SEQUENCE: 62
aaaatgaact tgaccagtgt 20

<210> SEQ ID NO 63
<211> LENGTH: 20
<212> TYPE: DNA
<213> ORGANISM: Homo sapiens

<400> SEQUENCE: 63
gcaatgtgga aacctaactg 20

<210> SEQ ID NO 64
<211> LENGTH: 20
<212> TYPE: DNA
<213> ORGANISM: Homo sapiens

<400> SEQUENCE: 64
gtacattgga atatgctcat 20

<210> SEQ ID NO 65
<211> LENGTH: 20
<212> TYPE: DNA
<213> ORGANISM: Homo sapiens

<400> SEQUENCE: 65
tctgatgttt ctgagagact 20

<210> SEQ ID NO 66
<211> LENGTH: 20
<212> TYPE: DNA
<213> ORGANISM: Homo sapiens

<400> SEQUENCE: 66

-continued agaggatccc ttggctggta 20

<210> SEQ ID NO 67
<211> LENGTH: 20
<212> TYPE: DNA
<213> ORGANISM: Homo sapiens

<400> SEQUENCE: 67
aacctgaata gtctgtttaa 20

<210> SEQ ID NO 68
<211> LENGTH: 20
<212> TYPE: DNA
<213> ORGANISM: Homo sapiens

<400> SEQUENCE: 68
ctggggcagt atactgaaga 20

<210> SEQ ID NO 69
<211> LENGTH: 20
<212> TYPE: DNA
<213> ORGANISM: Homo sapiens

<400> SEQUENCE: 69
acgtttaaaa cgagatcttg 20

<210> SEQ ID NO 70
<211> LENGTH: 20
<212> TYPE: DNA
<213> ORGANISM: Homo sapiens

<400> SEQUENCE: 70
tgtccaggaa aatatacagc 20

<210> SEQ ID NO 71
<211> LENGTH: 20
<212> TYPE: DNA
<213> ORGANISM: Homo sapiens

<400> SEQUENCE: 71
gctgattctg atggcttctc 20

<210> SEQ ID NO 72
<211> LENGTH: 20
<212> TYPE: DNA
<213> ORGANISM: Homo sapiens

<400> SEQUENCE: 72
ctgcatctct caatcttgag 20

<210> SEQ ID NO 73
<211> LENGTH: 20
<212> TYPE: DNA
<213> ORGANISM: Homo sapiens

<400> SEQUENCE: 73
taaggcagct catgagaaac 20

<210> SEQ ID NO 74
<211> LENGTH: 20
<212> TYPE: DNA
<213> ORGANISM: Homo sapiens
<220> FEATURE:

<221> NAME/KEY: misc_feature
<222> LOCATION: (1)...(20)
<223> OTHER INFORMATION: n = A,T,C or G

<400> SEQUENCE: 74
nnnnnnnnnn nnnnnnnnnn 20

<210> SEQ ID NO 75
<211> LENGTH: 20
<212> TYPE: DNA
<213> ORGANISM: Homo sapiens

<400> SEQUENCE: 75
ccaggccttc tattcacaag 20

<210> SEQ ID NO 76
<211> LENGTH: 63045
<212> TYPE: DNA
<213> ORGANISM: Homo sapiens

<400> SEQUENCE: 76
ttctctaata attataatca tggcgagtgc ttaccatata ttccaatcta tttacttcca 60
caagctcatt aattctcacc ctaaccctct gagatggtta ctattatttc ctctctgcag 120
ctgagggaat tttgggctag ggacgttatg taagttgagc cacgctacgc taaaagttcc 180
acactcaatt ctagcgtctc ggctctggac taccaagttc cggagcaagc agacagacca 240
cctctttacg ttcccgtagg ccacgctccg ggggcggggc tccagtgagg atactgcatc 300
ccatggtgcc ttgcgcgcca gcgcagccat tggtccggct actctgtctc tttttcaaat 360
tgaggcgccg agtcgttgct tagtttctgg ggattcgggc ggagacgaga ttagtgattt 420
ggcggctccg actggcgcgg gacaaacgcc acggccagag taccgggtag agagcgggga 480
cgccgacctg cgtgcgtcgg tcctccaggc cacgccagcg cccgagaggg accagggaga 540
ctccggcccc tgtcggccgc caagcccctc cgcccctcac agcgcccagg tccgcggccg 600
ggccttgatt ttttggcggg gaccgtcatg gcgtcgcagc caaattcgtc tgcgaagaag 660
aaagaggaga aggggaagaa catccaggtg gtggtgagat gcaggtaggg agagggctga 720
caggattccg agcgctgcgg cttcgctgct gggcccccta ctgcgcggtc cagggagagg 780
gattttattt gcatttcctg agggtcccag tttcttggtt ctccgcgttc tgttcaataa 840
aaatgacacc cggttgctgt gtgtatgtgg tttttaggag aaaataacat gtttgatttg 900
atcactgttc catactgaaa agtgcgttct tatgtttaaa ctatagtcaa taaagatgta 960
ggtgtcactt ttatatgcta cttcatgtag tttgtcagtt tggaagtaag actgaatacc 1020
tattttgcag atggttaagc acttacgttg gtattattac ctctaaaaag caatcaatca 1080
ctgttctctt tattctagat gcaatatttt ctgcatccct actaaacaag taaacatctc 1140
tgtctttaaa cattaaaaat taataaagtg agtttatgtt ttttaaaaga tcaagacaag 1200
ttaagctagt gtaaatttct gattgtgctg cagttttccc tttcatctgc gtgtttgttc 1260
atagaccaaa ctaaacggat atttcgagat aaagggatgt ggaggggtgt tcggccctcc 1320
cctgactggt ttccaaataa cttcccaatt ttaaaataag ctagaaactg ctgcttagtt 1380
agaattgatt tattcaactt tttagaggct ctccacagtt tactgagtat gtgtgttttg 1440
tgtgtccgtt tttgtggctg ttaacagttg ctgttgcaac ttttctgtaa accccaaagt 1500
attctaaaat taaaaggtta ttttttagaa aaacttgtat caacaaactt tcttaggcta 1560
ttgtttactc agccctggta acttgaattg tggatatcga aggtgatgac taggtttcta 1620

-continued

```
aacaaggtgt cagagaggaa attgggtggc aatcttaagt ctagccagtg acacttacta   1680
gttgttgtac tctggggctt ctgttagtag ttagttgttt gaagattttt atttaaaaat   1740
gcagtgcata taacaagtgc aaattttaaa attattttgg ttgtttaata aaaccaggca   1800
atattacctt ttccgtatgc atttatttaa tttctttttt aatgttagtt acaaaatatt   1860
tcagacttac aaaaagttat taagaacaat gtaataaaca tttgtatatt catcacccag   1920
attaagaaac aaaacaatca ttgctggagc cccccttttc cctctccatc ccttttcctc   1980
cagccactgt taaccattat cttgaacttg atgtttatga tccgtataca tttcaagtct   2040
tagaagagat ttactttatc accaatgaat agaatagttc tttgcttgtg tctaatattt   2100
acaataattt ttgtgtaaag agattttttt tttcagatta gccttttttct ttcaaatagc   2160
cttcctggtg cgtctgtcat taagcattaa gctttagtaa ataggcaact tatgagttgc   2220
gaggtcctca ggggttggta agccttttct gtaaagggcc cagagaaata aatatttatt   2280
ttatttaaat actttaggct ttgcagatca catgtggttt atcagttttt tttgagacgg   2340
agtctcgctc tcttaggccg tagtgcagtg gtgcaatctc agctcactgc aacctccgcc   2400
tcccggattc aagcaatttt cccacttcag cctctcaggt agctgggatt acaggcgcac   2460
accgccatgc ctggctaatt tttgtatttt tagtagagat ggggtttcac catgttggcc   2520
aggctggtct cgaactcctg acctcagaga atccacccac cttggcctcc caaagtgctg   2580
ggattatagg cgtgagctac tgtacccctt tacatgtggt ttctgtcaca ttattttctg   2640
atcttttttt ttttaagaac actttaaaac tgtaaaaatc attcttaaat ctgtcagggc   2700
aggggccagg tttgacccac aggttaaagt ttacagatcc ctacataatg cgctactggt   2760
tctctttctt atgtccctcc tattccatcc cctatttttt tcccaattta aaaagtcatt   2820
ttcaaacaca cataaatataa aatttaacat cttaaccact tttaagtgta cagttcagtg   2880
atattaaata cataatattc tgcaacaatt actaccatcc atctccataa ctcttttcat   2940
catgaaaaac tgaaactcta tacacattaa acaataactc cccatttccc tctcccatca   3000
acccgacacc taccattcga ctgtcttatg attttgacta ctctaagtac ttcataaagt   3060
ggagtcataa tacagtattt atccttttgt gacttgctca ttccacttag gcataatgtc   3120
ctccaggttg gaccatgttg tagcaaatgt cagggttttc ttccttttta aggctgcata   3180
gtatttatta tatgtatata ccacattttg cttgtccctt catatgtcaa tggatacttg   3240
agttacttct ttttttgttg ttgttgtttt tgagaccgag tctcgctctg ttgcccaggc   3300
tggagtgcag tggcgcggtc ttggctcaca ctgcaagctc catctcccgg gttcacgcca   3360
ttctcctgcc tcagcctccc aaggagctgg gactacaggc gcctgccatc tctcccggct   3420
aatttttttgt atttttagta gagacggggt ttcaccatat tagccaggat ggtctccatc   3480
tcctgacctt gtgatctgcc cgccttggcc tccctaagag ccgggattac aggcgtgagc   3540
tacggagccc ggccttgagt tacttcttac ttttagctat tatgaataat gttgctatga   3600
atatgggttt tcaattcttt tgggtattta cccagaattg taattgctgg atcatatgat   3660
aattctattt taaagttttt gaggaaccga caaactattt tccacagtgg ctggaccatt   3720
ttacattcct accaacagtg cataagggtt ccaatttctc cacatcctca ccaacgttta   3780
ttttctgttt cttttttttt tttcaagtag ccatccattg ggtgtgaggt gctatctcat   3840
tgtagttttg atttgtattt ccctaatgat taatgatgtt gagcatcttt tcatgtgttt   3900
actggccatt ttgtgtatct ttggagaaat gtctgtttaa gtcctttgcc catttttaaa   3960
```

-continued

```
ttggtttgct tttttgttgt tgagttttag gaattttcta tatattttgg atattttcag   4020
atacataaac ggcaaaaatt ttttccccat tactgtggtt tgccttttta ctcattgata   4080
ccgtgtggtc ttttcctttc tttttctttt tggaaccagt gcatggcctc tttgttgatt   4140
ctgtgtttgg ccccagtgca gcctgttctg tgctatgtgt ctgcagtgct gaaaccaggc   4200
ctacccagca ccatacagaa gtccaggctg tagataccaa tgcatgggtc acatttgata   4260
cccaaatctg tgtgttcctg gatctccaaa ccaaagtttc cagtatctga gaagttgttc   4320
tttcttgatt cacactcctg catctttaga cctttcttca gggtttcttc tgctttggcc   4380
ctttgtgcag tgggtggcaa tcttcacttc tcctgatgcc aaaggatctg acaatgtatt   4440
tgactttgga gaacacaggg gtctggccta tgagctgctc caacaccttg gctgctgggg   4500
tcagtcatct ccagtctcct ccatacagat gttgagacag aaaatcgttc tgtcacccag   4560
gctggagtgc agtggcacag tctcggctca ctgtaacctc tgcctgtcag gttcaagcaa   4620
ttcttatgct tcagcctccc aagtatctgg gattacaggt gtgcaccacc atgcctggct   4680
aatttttttgt atttttagta gagatggggt ttcgccttgt tggccaggct ggtcttgaac   4740
tactggcctc aagtgatcca cccattttgg cctcccaaag tgctgggatt atgagtgtga   4800
gccctcatct ggccagagtt ctcttttttt taccttgatc ttgcactatg atggagaaaa   4860
ggaagataaa gtcttttttt ttcccttggg tttgtttgtt tgtttgtttg tttgtttttt   4920
gagacggaat tttgctctcg ttgcctaggc tggagtgcat tggtacgatc ttggcttact   4980
gcaacctccg cctcctgggt tcaagccatt ttcctgcctc agcctctaga gtagctggga   5040
ttacaggcat gcgccaccac gcctggctaa ttttgtattt ttagtagaga tggggtttca   5100
ccatgttggt caggctggtc ttgatctcct gatctcaggt gatccgtcca ccctggcctc   5160
ccaaagtact gggattacag gcgtgagccc gtgcctgggc tatttttttt ttctcccctt   5220
taaatatagt atcttgcttt attgcccaga cttgttgtga actcctggac tcaaatagtc   5280
ctcctacctc agccttccag gtagctggga tcacagggat gctgtctttt gatacacaaa   5340
cattttaaat ttttatgaag tccagtttgt ctttttgttt ttgttccctg tatctttggt   5400
gttatatcca agaaatcatt gccaaatcca ttgttgtgaa gcttttgcct tatgttttct   5460
tctaagagtt ttatagcttt aggtcttaca tacattttttg atccattttg agttaatatt   5520
tgtatattgt gttagataag ggtccaacct cattcttttg catatggata tttagtttcc   5580
cagcaccatt tggtgaaaag cttgtctttt tctgattgaa tggtcttggc aaccttatta   5640
aaaatcattt gctcatatgt aagagggctt atttctaagt gctgttatgt tccattggtc   5700
tataagtctg tctttatgtc agtaccacat ggttttgatt attgcagctt tgtagtaagt   5760
tttgaaatca ggaagtgtga gtcctccagc tttgttcttt ttcaagattg ttttggctat   5820
ctggactccc ttgggattcc atatgaattt gaggatgaat tttctatttt ttgtaaaaca   5880
cgtcattggg attttaatag ggattacatt gaatctatag atcactttgg gtagtattgg   5940
catcttaaca atattaagtc tttcagttca tgaacaaggg atgtgtttcc atttatttat   6000
gccccttaat ttctgccagc agtttttttt tgtttgtttt tgttttgaga tggagtttcg   6060
ctcttgttgt ccaggctgga gtgcagtggc acaatcttag ctcattgcaa cctccacctc   6120
ccgagttcaa gtgattctcc tgcctcagcc tcctgagtag ctgggattac aggtatgtgg   6180
caccacgacc agctaatttt tgtattttta ctagagacaa agtttcacca tgttggtcag   6240
gctggtcacg aactcttgac ctcaggtgat ccacccacct tggcctccca aagtgctggg   6300
attataggcg tgagccactg cgcctggcct cagcagtgtt ttatagtttt cattttataa   6360
```

-continued

```
gtctttcacc tccttggtta aattaattac taatatttta ttctttttgg tgctatttta   6420
aattgagttg tttttgtaat ttccttttta gattgttcat tcttagtgta taaaaatgta   6480
actggaggct ggacgcagtg gctctcacct gttatcccag cactttggga ggcaaggtgg   6540
gcctcccaac tcctgatcac gagatcagga gttcaaggcc agcctggcca acatagtgaa   6600
accctgtctc tactaaaaat acaaaaatta gccatgcatc gtggcgcgtg cctgtagtcc   6660
cagctactta ggaggctgag gcaggagaat cgcttgaacc tggaaggtgg aggttgtggt   6720
gagccaagat cgtgccactg tactccagcc tgggcaacag agtgagactc tgtctcaaaa   6780
aaaaaaaaaa agaaaaaaga aacgtcgctg gattttgctt gttgactttc tatccagcta   6840
ctttgctgaa ttcacttatt agttctaaca gttttttttt gtgtgtgtgt aattttagag   6900
ttttcttttc tttttttttt tttgagatgg agtctcgctt tgttgccagg ctggagtgca   6960
gtggcgcgat ctcggctcac tgcaacctct acctcccagg ttcaagcaat tctcctgcct   7020
cagcctcccg agtagctggg actacaggca cacgctacga cgcccagcta atttttgtat   7080
ttttagtaga gacggggttt caccatgttg gccaggatgg tctcgatctc ttgacctcgt   7140
gatccacctg cctcagcctc ccaaagttct gggattacag ccgtgagcca ctgtgcctgg   7200
cttttttttt tttttaatta actattgaac ttctgtttat tattattatt attatttatt   7260
tatttattat tttttgagat gaaatctcgg tctgttgccc aggcgggagt gcagtggtgt   7320
gatctcggct cactgcaacc tccgcctccc gggttcaagc aattctgtgc ctcagcctcc   7380
ggagtagctg ggattatagg cgctcgccac catgcccggc caatttttgt atttttagta   7440
gagatagggt ttcatcatgt tggtcaggct ggtcttgaac tcctgacctc gtgatccgcc   7500
cgcttcggcc tcccaaagtg ttgggattac aggcgtgagc cactgcactt ggccttattt   7560
ttattatttt tttcatcaac ttttaagttc tggggtacat gtgcatgatg tgcaggttta   7620
tcacataggt aaacctgtgc catcacagtt tgctgcacag atcaacccat cacctagcta   7680
ttaagcccag catccactag ctattcttct tgatgctcta gctccttttg ccccactgaa   7740
ttttagggtt ttctttcttt tctatttttt tttcttttga gacagactct cgctctgtca   7800
ccaggctgga gtgcagtggc acaatcttgg ctcattgcaa cctctgcctc ctgggttcaa   7860
gcgattctcc tgcctcagcc tcccgagtag ctgggactac aggcatgcgc ccatgcctag   7920
ctaagttttt gtagttttag tagagacagg gtttcactat gttggcaagg ctggtctcaa   7980
actcctgacc tcaagtcccc ttggggttcc tgaagtactg ggattatagg tgtgagccac   8040
cacgcccggc cagattttct atataaaaga tcatataatc tgcagacaga taattttact   8100
ttttcctttt ctttcttttt ttcttttttt gagatggagt ctcgctctgt cgcccaggct   8160
ggagcgcggt ggcgccatct ctgcttactg ttacctctgc ctcctgggtt caagcagttc   8220
tctgcctcag cctcccaagt agctgggatt acatgcacat gccaccacgc ccagctaatt   8280
tttgtatttt tagtagagat gggagttcat catcttggct aggctggtct tgaactcctg   8340
acctcgtgat ccatccgcct tggcctccca aagtgctggg attacaggca tgagccaccg   8400
ctcttggccc tcaacctttt ccttttcaat ttggatgcct tttattttta tttttcttcc   8460
tttttttttt gagatggagt ctcgctctgt tgcccaggct ggaatgcagt ggtgcaatct   8520
ctgctcactg caacctacgc ctcctgggtt caaacgattc tcctgcctca gccttccgag   8580
tagcttgtac tacaggcatg tgccaccata aacagctaat tttttttttt tctcgtattt   8640
ttagtagaga cggggtttcg ccgttttagc caggctggtc tcgatctcct gacctcgcga   8700
```

-continued

```
tccgcctgcc tcagccttcc aaagtgctgg gattacaggc gtgagccacc atgcccggcc   8760
cttgtttttc tttcttgcct aattactcta gctagaactt acagtattat gtcgaatgga   8820
agtggcaaaa gtgggcattg ggcatccttg tcttgctcct gttcttttat ttgttagttt   8880
gtttgagatc ctcctgcctc agtttcctga gtagctggga ctatagacac actactacac   8940
ccagctaatt aaaaaaataa ttttttttt ttttttagag atggggtctc gctatgtttc   9000
ccatgctgat cctgaactcc tggcttcggg tgatcctcta ctcttaccct cccatagtgc   9060
tgtgattaca ggcatgaacc actgtgctgg ccctgttctt gtttttagag gaacattctt   9120
cagtctttga ccatcaatta tgtttgctgt gggtttttca tatgttgctt ttattttgtt   9180
gaggtagttt cactctattc ctagtttgtt gagcattttt atgactaatg ggttttgaat   9240
tttgtcacat gcttttcctg catcgattga catgattctg tggtttcctt cattctgtta   9300
atgtggtata ttacattgat caatttttac atgttggacc atccctgtat tccaggaata   9360
aatcccactt ggtcatggtg tataatcctt gtgctgctca gttcaatgtg ttggtatttt   9420
gttgaggatt tttttttatc agtgttcata agggatagtg atctgtagtt ttcttgtagt   9480
tgcctttgtc tggctttggt atcagggtaa tgcttgcctc acaaaatgag ttgggaagtg   9540
ttctctcctt tgccagattt tttctgggaa aagattgaga agaactggta ttagatcttc   9600
ttgaaatgtt ttatagaatt cacctatgaa actatcagat ctagggcttt tctttgtcag   9660
gagatttttg gttagtgagt ccatctcttt actggttata gctccattca gaatttccat   9720
ttctttgtga tttagtcttt gtaagtattg tgtttctagg aatttgttca gctgggttat   9780
ccgatttgtt ggcatacaat tgttgaaaat actctttcaa caataagaga gaagacacaa   9840
ataactagtt cttttgtttc cagttcctta agttgtaaag ttagggtgtt gatatgagat   9900
ctttcttgct ttttaatgta agcattcata gctataaatt tcccccttag cactgctttt   9960
gctgtgtccc gtaagttttg gtatgttgta ttttcatttt cattaatctc taaaatttc   10020
taattttcct tgtgatgtct ttgaaccctg gttacttaaa cacacacaca cacacacgtg   10080
tgtgtgtgtg tgtgtgtgtg tgtgtgtggt tttttgtttg ttttgagact gagtttcgct   10140
cttgttgccc aggctggggt gcaatggcgc gatctcggct cactgcaacc tctgcctccc   10200
ggttcaagcg attctcctgt ctcagcctcc agagtagctg ggattacagg cgcctgccac   10260
cacgcctggc taatttcaca cacacattta aaaaatacat ctacctgctt ttacttcaga   10320
atctttgcaa tttctgttct ctctgcctga aaatttttc caccaaaata tctacagggc   10380
ctggctccct tgctttttag gttctgctta aatatcacct gcgtagaagc attccctaac   10440
taccctaaaa tagcaaccaa ctatcttcca ccctcaacac ttcctatccc ccttaaactg   10500
ctttcttttc ttttcttttt ttttttttt ttttgagaca gagtctcgct ctgttgccca   10560
ggcctggagt gcagtggcgc attcttggct caccgcaacc tccacttcag cctcccaagt   10620
agctgggact gtaggtggct gccaccatgc ctggctaatt tttttttttt tgagatggag   10680
tctcactctt tcacccaggc tggagtgtag tggcacagtc tcggctcact gcagcctcca   10740
tctcccaggt tcaagtgatt tctggctaat ttttgtattt ttagtagaga tgaggtttca   10800
ccatattggc cagggctagt ttcgaacttc tgacctcaag tgatctgccc accttggcct   10860
cccaaagtgc taggattaca ggtgtgagcc actgtgcctg gcctaatttt tgtattttta   10920
atagtgatgg gtttttacta tgttggccag gctgatctca aactcctgac ctcaagtgat   10980
tcacccacct cagcttccca aagtgctgag attacaggcg tgagccactg tgcctggcct   11040
gctttatttt catttctaat ttatcagcat ctaatatatt tattcatttt atagtcatct   11100
```

```
cttccttcaa ctaagttaaa agctccctga gcacaggatt ttggtgtttt tttctttcct  11160
ttaactttgt attgttcatt gctgtatctc cagtgtctag aaaattacct atcacatagt  11220
aagtacttga tgaatatttg tggaatgagt taatttagca cttctccaca ggataggact  11280
taggtttttt taatcctcaa tctcccttcc ctcaccattt tgattgtttg aatttttata  11340
taactatggt gaagccaaca aattgatgga tttgttagtg tgagcagccg aaactttgca  11400
atttctaata agttagagaa gtctgggtag gaaactaatg acttggcagt actctttctt  11460
agagtacaca tagtccctaa agcttctctg agaattttga taactttgag gaatgtgtga  11520
tctgtatgaa tttcctatca cttagtcctg acaatgtgaa tggtattcat ttggtaactt  11580
aattttatac gtccaggcaa gatactagtt taggggatgc caaaaataat agactaattg  11640
gaaaagcttt agccacatga gagcaattca ctccacttga tgctcttggc ctacctcagt  11700
ataagttggt tctaccttag ttttgttgaa gttttaataa tactgtacat tcatgttggt  11760
tatatgcatt gtgtaagttt tagtatagtt ggcaaatgaa agcattacca gatactacct  11820
gggagttaag tttcctagga tcacagattt ggtcttctga tcacttggaa gtatacttag  11880
agtgggctgt gccaggggaa gttgaggtat ccttcttaaa taagtagcaa cttggtttat  11940
ctagtgataa gggggaaata atttcctgtt tggcactttc tccaaaatat atgatactca  12000
atgggaaaaa tgaactcagg tcaagattat gtctctccct ttggcccaga catgtattga  12060
gtatataatt gtcttattga tgctactctg tggactgtga tattagtttt cccataattc  12120
ctcttaggat gacatttatt aggcaatgta gtttaacaga tatttaagaa cctactgtgt  12180
gctaagcatg gtagttgttg ctggggaaac agtaaactag acagtatttc tttctgtagt  12240
gatctgaggt ttagtgggta acacattaaa aaaaaaagat aagagaggtg atgtttagaa  12300
aaggtgtata aagggtgctg taggaatata tagcagacat ttaatgtggt cttggttgga  12360
gcaggtgggg gaggcacata ggatagaaag gacttcctga ggaaataatc atttcaacta  12420
aatacctact caggcatttc cgtagaatga ggactcttga tccagtcggc agtgtagacc  12480
ttctgtgtct attcactcat ttaaaaatgg ggctaataat attaccaacc tcacagtgtt  12540
gtgtggacaa actgagtgag cacaatgcaa agcacttgaa acaataagta cctggcacat  12600
agtaagtact caacttatta gtcattattt ttatgtactt tttattttgt gccaggtatc  12660
tactggcaga ttagtatttt gaacacaaat ttgacatgtt tttttctact acatcataac  12720
ctaatttgat cggatttttt tttttttttt tttttgagac ggagtttcgc tcttgttgcc  12780
caggctggag tgcaatggcg cgatcttggc tcaccgcaac ctccacctcc caggttcaag  12840
caattctcct gcctcagcct cccgagtagc agggattaca ggcatgcacc accatgccca  12900
gctacttttg tatttttaat agagacagag tttctgcatg ttggtcaggc tggtctcgaa  12960
ctcccgacct caggtgatcc gcctgcctcg gcctcccaaa gtgctgggat tacaggcgtg  13020
agccactgcg cccagccttg atcagatttt aagaatagga gaaatggaat tctgaaaaat  13080
aagtttggca tttttacaag ttaaaacctg ttagtggctg ggcacagtgt ctcacttctg  13140
taatactagc accttgggaa gctgaggtgg gataatcact tgagcccgga agtttgagac  13200
cagcctgtgc aacacagcaa gaccccatct ctaccatcaa aacaaaacaa atctattcgt  13260
atctgctcta agaagctgcc agaattgtaa tgtcttaaca tatctttgaa catttaaaaa  13320
attatatttg tgaaacttga gacacttata attttactgt ctgctttagc aatatcactt  13380
agtcctgatt taatctccat caccaacaat gtggtcaaaa tttcgcattt ttcttgacaa  13440
```

-continued

```
atgtagttag tgaaaatgtc attgataacc tgagaactaa gagctcttga atgactttgt 13500
gtatttcttt ttatagacca tttaatttgg cagagcggaa agctagcgcc cattcaatag 13560
tagaatgtga tcctgtacga aaagaagtta gtgtacgaac tggaggattg gctgacaaga 13620
gctcaaggaa aacatacact tttgatatgg taacatatgg tgcaatttct ttattatcca 13680
ctaatgtaaa ataattttaa tatacatatt ttacctggaa aatggtgtat acttagaaat 13740
ttcagttgtc tctgaattgt cagatggctt ctagtgggct gaattatgaa ttagttaaca 13800
tacgaaaaac aaaattatta aaatgagtaa ttttgaggtt gatttttttt tttttaattt 13860
ttttcgttag gtgtttggag catctactaa acagattgat gtttaccgaa gtgttgtttg 13920
tccaattctg gatgaagtta ttatgggcta taattgcact atctttgcgt aagtaaaagg 13980
gtgtttttc tgatttatga aaaagcttaa atgcttgtgt tttttgttgt tgtttgtttg 14040
ttttttgaga cggagtttca ctcttgttgc ccaggctgga gtgcaatggc gcgatctcgg 14100
ctcactgcag cctctgcctc ctgggttcaa gcaattctcc tgtttcagcc tcccaagtag 14160
ctgggattac agctgcctgc caccatgccc gctaattttt gtatttttag tagagacgtg 14220
gtttcactgt gttggccagg ctggtctcga actccggacc tcaggtgatc cgcccacctc 14280
ggcctcccaa agtgttggga ttataggctt gagccactgt gcctggcttg tttttttgttt 14340
ttctagtcta tcactaagag tcatatgggt gcatgtttct ttttgattta acacttgtta 14400
atctttacag gtatggccaa actggcactg gaaaaacttt tacaatggaa ggtgaaaggt 14460
cacctaatga agagtatacc tgggaagagg tatttattgt ttataacata cttttatctc 14520
taatgtgact gaaatttaac tgtataaaac ttgtttgagg gcctctgtct tggaatagag 14580
atcagagtac ctatgtcaaa atgaacttag gataaaccac tactacagta aaattaaagt 14640
gcatggtatg actcctgttt aagaaacagc ctcaatggaa gaggaaggac caatatatat 14700
ggcacagtta tatgataaaa gaggagtcta tttatgacag aatggttgga gcagaatatt 14760
gtagaaaagt tggaatatga gtgaagcttg aaggcaggga gggctttgta ttgaaggaat 14820
gggtctcaga aagttagcat ggccagggga agtatagtac tttattcatg atgatcctaa 14880
gtgttcaaga aattaagatg aatgtattgt ttaatattgc agaaagcata tactatgttt 14940
tacaaagatt tccatgaatt taagtgagtt taataactaa gagagagaac caatactgga 15000
agaaagttga aagaagacca agacaagttg aactagagct gaagtgttaa aacttttaaa 15060
aaaaagttta gttttaaatt tagtaatgtg tttaaattta aatgagttta ataactagtt 15120
aattggtcgg gcacggtggc tcatgcctgt aatcctagca ctttgggagg ctgaggcggg 15180
cagatcacct gaggtcagca gttcgagacc agcctggcca acatggtgaa acccggtctc 15240
tactaaaaat acaaaaatta gctgggtgtg gtggtgcata cgtgtaatcc cagctacctg 15300
agaacgagac tctgtctcaa aaaaaaacaa aaaaacaaaa aaccaaaaaa ctagttaatt 15360
taaaaaaaaa aagaattttt tttaattttt tttttttttt ttaaatttta aagtgatggg 15420
gtcccactgt gttccccagg ccagtcttga actcttgggc ttcaggagtc ctcccacttc 15480
agcctcctga gtagctggga ttagaggcac atactacctt gcccagctaa ttttccaaat 15540
tattgacagt tgggtagaac ctttcttcta gtggttacat aattgagtca ttaacttact 15600
ttacatatat agataataaa gttatgaaat tgttaccata ggagatatgg aataggctta 15660
aagcatagtt tcgctgggca gaattattga acttggcgtt tttttttga gacggagtct 15720
cgctctgtcg cccaggctgg agtacagtgg ctcgatcttg gctcactgca acctccacct 15780
cccgggttca agtgattctc ctgcctcagc ctcctgagta gctgggacta caggtacata 15840
```

-continued

```
ccaccaagtc cggctaattt ttgtattttt agtagagatg gggtttcacc gtgttggccg  15900
ggatggtctt gatctcctga ccttgtgatc cacctgcctt gacctcccaa agtgctggga  15960
ttataggcgt gagccaccgt gcctggccga acttggcttt ttaagtagat aggttccatt  16020
ggtttctatg taatgctcag ggatgaagat ggctaagaag tgtgacaggt ttatggaggg  16080
tgtgaagact actgtagaac agactgttgt aaatgacttc tctaacatta ggttagttgt  16140
ttcttttttt gttttgtttt aacttgcttt gccatactta tgtttaaata tattataaag  16200
gaggcccatg tattttaact gccacagtaa atggcattct tcctttatat tagtccttat  16260
tataatttca ggatcccttg gctggtataa ttccacgtac ccttcatcaa atttttgaga  16320
aacttactga taatggtact gaattttcag tcaaagtgtc tctgttggag atctataatg  16380
aagagctttt tgatcttctt aatccatcat ctgatgtttc tgagagacta cagatgtttg  16440
atgatccccg taacaaggta attcagtctt tgagaatgaa atgtctctga attttaatgt  16500
gtgaggcttt gagaagtcag agagagagag agagagagag agagagagag agagagtgtg  16560
tgtgtgtgtg tgtgtgtgtg tgtgtgtgtg tgtgttttaa ccaatctaat ggatgttctt  16620
ttggtatttt ggtcagagag gagtgataat taaaggttta gaagaaatta cagtacacaa  16680
caaggatgaa gtctatcaaa ttttagaaaa gggggcagca aaaaggacaa ctgcagctac  16740
tctgatgaat gcatactcta ggtaagaaag ccatagtctc ttccctagcc ccattttctt  16800
ttaagaagaa ttaggaactt ggagaaagtc aaattggggt gggtcagggt atgtgggtca  16860
cgtacctaga gtttgtgtta taaggagggg tcattggtaa ttggcttgag atttatatgg  16920
aaggaaccaa tattggaaga atgttgaaag gagaacaaag ataagttgaa ccatagctga  16980
agtattaaac tttttttct tttttgagac gaattttcgc tcttgttacc caggctggag  17040
tgcagtggcg cgatcttgac tcactgcaac ctctgcccac cgggttgaag caattctcct  17100
gcctcagcct cttgagtagc tgggattaca ggtgtctgcc actacgccca gctaattttt  17160
gtatttttgg tagagatgtg gtttcaccat gttggccagg ctggtctcga actcctgacc  17220
tcaggtgaac cacctgcctt ggcctcccaa agtgctgaga ttacacgtgt gagccacggc  17280
gcccggccta aacttttttta aagtagaaga atccttttat tctagtaaca tgatatatgg  17340
aagcccagga taaaatgtgg ctgctatagt tgattttgga atgggacgct ctgaggctta  17400
cctccttagc cttatgaagg ggtccctgag gcacttttgt ggagcccccct actgatatta  17460
gaatatagtt tgaaaaccct tgcattgaat aaggattaga agttaggtct tttaaaatgg  17520
ctttatttta gtgtgggaga cagatggtca ctaacactgg ctttcatggg gtgaaaggga  17580
tgattttttt cgctctaaat atcttttacc gaaatataaa attccttttt aaaaaattgt  17640
ttattttcct ctcttaccac tctattcatt gagatataaa atccctgtca taaatttacg  17700
taagttagaa actccttttt tcttgtaaag acccgtacag gacaaattcc aaattctaca  17760
gatatagttt actaaaacag aagtggtttt tttgtgtgtg tgtgtggtct ttaaacctca  17820
gaatgtaata gaaaaagcaa tggattgcaa ttagatattt gcgtgtagtc tcagtttcgc  17880
ggttaattca gtatgtgact ttttgtaaat aagtgaattt atctgcttat cagtttctct  17940
gagctacaaa attattgtta ggattagaag tcttatttct tttctggctt gtagttgaaa  18000
atttctataa aatgccataa caattacagt tgcaactcta aaaaagtttg catttaaaga  18060
aagaagaaaa atataacata aaagtgatta agatcatgga attttggatg atttcaaaat  18120
tttaattaaa ttttcactta atggctttcc aataaaatgg aaattttatt ctgtggttga  18180
```

-continued

```
ttataactta atttcatgta gaattttgag aactgaacta aagactaggt aaaatttctt  18240
taggtacatt tcactaaagt ataaaatttc tatttttcct tttttcttgt atgtagactt  18300
gtataaaggt cactttttat gaaggtatgt gacaaagagg agaagctaat taattcagtt  18360
ttcccaaatt agagctaact tcaatgctta tttgtattaa ttgcctaatc tggattagga  18420
atgggtagat aatggtagaa aaacatgaga tgaatagtat tattattatt attattattt  18480
ttgagacaga gcctctctct gtcccccagg ctggagtgaa gtgatgcgat ctcggctcac  18540
tgcaagctct gcctcccggg ttcacgccat tctcctgcct cagcctcctg agtagctggg  18600
actacaggtg cccaccacca cgcctggcta atttttgta tttttagtag agacggggtt  18660
tcactgtgtt agccaggttg gtctcgatct cctgacctcg tgatccgtcc acctcggctt  18720
cccaaagtga ttacaggcgt gaggcaccat gcccggtgga gatgaatatt ataattcaga  18780
tctatagttt acatttatgt ttttccttag gtcttcctcc ttttctgtaa ttttaaataa  18840
tttaaataat tttataaaaa tgatacttgg ctgggcgcga tggctgacgc ttgtaatccc  18900
agcactttcg gaggccaagg tgggtggatc acttgaggtc cggagttcaa gaccagcctg  18960
gccaacgtgg tgaaaccccg tctctactaa aaatacaaaa attagcttgg tgtggtggcg  19020
tgtgcctgta atcccagata ctcggtaggc tgaggcagga gaactgcttg aacccaggag  19080
gcagaagttt cagtgagctg agatcatgcc attgcactct agcctgggca ataagtctca  19140
aataaataaa taattaaaaa agatacttaa tttttttttt aagtaacatg aaagtacaaa  19200
gaagaaaatt gaaacttacc agattctctg tcaattgtca gtgatattaa caaacataat  19260
aatgttcacc aaatgccatt ggatacagaa agaatgtctt tggtcatctg tataattttt  19320
tttcccccta agataaaaag cacagtattt gttttgtttt ttgtttttt gtttgcttgt  19380
ttgtttttt gtgatttttt tttttgagac agcgtctcac tttgtcaccc aggctggagt  19440
gcagtaactc aatcatggct tactgcagcc ttgacctcct gggctaaagt gatcctccca  19500
cctgagcctc cagggtagct ggaactgtag gagcgtgcca ccacgcccag ctaattttta  19560
aatttttttg tagagatgat ggtcccacta tgttgcccag gctggtttcg aactcctgag  19620
ttaaagtgac cctcctacct tggcctccca aagtgttggg attacaggca tgagctacca  19680
cccctggcct gaatatcagt atttagcata aggtagactt ttgaacattt tataatctag  19740
cagtgattat cttgtagtgt tttagtaatc atgctgttta ctatttctgc tgttagggga  19800
taggagtcat ctatttctga tgacagtctc aaagcagaga agtgtacttg tgcatgtaca  19860
caacagctga catggatggg aaggtggaag agtaaactaa tgccttacct ggtaccattt  19920
gaatttatgg taatgacata tttcaaatgg ttcttatgaa tagaagatga ttacaagcca  19980
tctcttcttg acataccagg caactgtttc gaccccaccc acatccagct ttcagaggtg  20040
cctcaggatt ctaagtcttt tagagagctt cttattgatg cctcttttgc aggcagtaga  20100
tatgagaaaa caaaatccta atcactgttc tatctatctc ctatcttcca aaatattctt  20160
gatatctcct gtctgatgtt atctttctct actcatgtgg atttagatct tctttcctgt  20220
tttcagtatt tcagaagcag caaatgctat tttacattat aatgactggg caacttgata  20280
ttgttttcta gtcgttccca ctcagttttc tctgttacaa tacatatgaa agaaactacg  20340
attgatggag aagagcttgt taaaatcgga aagttgaact tggtaagcat ccaccttaat  20400
actactgttt cactcttaaa caccttatag agcagcttga aattttgtcc ttgagacaaa  20460
atttttgtgg tcactgggtg attagctttg tagtgggaga agaaatttgt taattacaga  20520
aaaaattatt ttgctggcga tttaatacat tatgtatcct gtgagaatga aagtctttga  20580
```

-continued

```
atccaaatcc aatagactca ctttttattt ttatttttaa aattaaaggt tgatcttgca  20640
ggaagtgaaa acattggccg ttctggagct gttgataaga gagctcggga agctggaaat  20700
ataaatcaat ccctgttgac tttgggaagg gtcattactg cccttgtaga aagaacacct  20760
catgttcctt atcgagaatc taaactaact agaatcctcc aggattctct tggagggcgt  20820
acaagaacat ctataattgc aacaatttct cctgcatctc tcaatcttga ggtaagccct  20880
ttgaaaggaa gctgcaagtg tagtagctgt aattcttatt tggctattat atattttaaa  20940
agttcattta ctaggatgga cacagtgact cacacctgta aacccagcac tttggaagtc  21000
caaggtgggc ggatcacttg agcttaggag tgcctgggca acatgccgaa accctgtctc  21060
taccaaaaat acaaaaaatt agctgggttt ggtggtgtac aactgtggtc ccagctactt  21120
ggggggctga ggtgggagga tcacttaagc ctgggaggca gaagttgcat taagctgaga  21180
tcatgcaact acactccagc ctgggtggca gagggagacc ccatctcaaa aaaaaaaaag  21240
tatgtgtata aaaaaaaaga aaagtatgtg tatacacaca cacacacaca cacacacaca  21300
cacacacaca cacacacata tagtagggaa aaaaagttca tttagtagct tcattttttt  21360
tttttgaga caaatcccac tcttgtcccc cagactggag tgcgatgacg cgatctcggc  21420
tcactgcaac ctccacctcc caggttcaag cgattctcct gcctcagcct cccaagtagc  21480
tgggattaca ggcacctgcc accacgccca cctaattttt gtatttttag tagagacgtg  21540
gtttcacctt gttggccagg ctggtctcaa acccctgacc tcaggtgagc cgcccgcctt  21600
tgtctcccaa agttctagga ttacacgcgt gtgccactac tcagcctagc ttcgttcatt  21660
ctatgctata atgtaaaaga atctggacat tgcatatgaa tatatacagg aggacactcc  21720
tgaagaagtt atctttttcc ttcctggcag agtttttaac cttaaaaagc cagtttctta  21780
atggcttttt ccacacagtc ttcaaagaaa attgctgtgg tcattagcag tgggtggtgt  21840
atggagattt aattgaggac ttagaagcag gccaagtgaa tgctcgctag tgtggtagag  21900
gctgcttaga gaacactgaa gatggcgttg gatgtgtgag aacagagagg aaaaccaaga  21960
aaagtaacaa agatggtaaa atgtacgctt attttattgc tatcatctgc cttaagtgga  22020
aattttattt atttattaat ttttttactt ttagaggtag agtctcatac tgttgccaag  22080
gccgcagtac agtagcatga tcatggctca ctgcaactta aattcctgga ctcaagtgat  22140
tcccccaacc acagcctcct cctgagtagc tagtactaca agtgtgagcc accaggcctg  22200
gctaagtttt gttttgtttt gttttaaata gagacagagg tctcactatg ttgcccaggc  22260
tggtcttgaa ctcctgggct caagggatcc tcctacctca gcctcccaaa atgctgcgat  22320
tataggcatg agccacctca cttgacctaa atggatttta aaaagctttt ttaggccagg  22380
cacggtggct tacgcctgta atcccagcac tttgggaggc tgaggtgagt ggatcatctg  22440
agctcaggag ttcaagacca gcctgagcaa catggtgaaa ccccatctct actaaaaaat  22500
acaaaaaatt agctgggcat ggtggtgcgc gcctgtaatc ccaactactc aggaggctga  22560
ggcgggagag ttgcttgaac ccaggaggtg gagattgtag tgagccgaga ttgcgccatt  22620
gcactcaagc ctgggtgaca gagtgagact ctgtctcaaa aaaacaaaaa agctttttta  22680
aggtgtccaa ctgccccttc attaaaaaaa aatctttgtt gagatttaat tcacatacca  22740
taaaattcac tgatttaaag tatattaatt taataattct agtatattta cagagttgtc  22800
caaccatcac caaaatctaa gttttgaaca ttttcataac ctcagaaaga aagcctgtac  22860
ccattgaaat tacttttcca tttgccccac tcccatcgct actgcttttt gcatctatat  22920
```

-continued

```
atttgcctat tctgggtatt tcatataaat ggaattacgt aataggtagt tttttgtgac  22980
tggcttcttt cacttagcat aatgttttca aggttcatct gtgttgtacc agcaatactt  23040
tattcctttt tacaggtgaa tattattcta tagtatggat atgggatttt tttgtttttt  23100
tttttttttg agatggagtc tcgctctgtt gcctaggctg gagtgcaatg gtgtggtttt  23160
gactcactgc agtcttcgcc acccgggttc aagtgattct cctgcctcag cctcctgagt  23220
agctgggatt acaggcgcca ccaccatgcc tggctaattt ttgtatttgt ggtggagaca  23280
gggtttcacc atgttggcca ggctggtctc gaactcttga cctcatgatt cacccgcccc  23340
ggccttccaa agtgctggga ttacaggtgt gagccactgt gcccggctga tataggacat  23400
tttgtttatt catcagttgg tagattgatt gagctttgtg gtttttttgt tttgttttgt  23460
tttttgtttt tttttttttg agacaaggtc cctctctgtt ggctggagtg cagtggcaca  23520
ttcactgtaa cctcaacctc ctggccttaa gtgatcctcc caccttagac tcccaagtag  23580
gtgggactat aggcacatac tactatgccc agctaatatt tatttattta ttgtagaaac  23640
aggatctccc tatgttgcca aggctggtct cgaattcctg ggctcaagtg accctcatgc  23700
cttggcctcc aaagtgctgg aattacaaat gtgagccatc attgagttta agaatagtct  23760
aaaggaaatt atcctaaggg tcgagactct gaaaattgaa gagaagggaa aaaaggattg  23820
aacaacttcc tttttaaagg ttgggcatag tggtcttaat gactagattt taaaattaga  23880
tataactata aaatattact tgtaagttat tatataacat attttagata acagaactac  23940
attattctca caatatcttc agtaattgac ctttcctttc catgacagga aactctgagt  24000
acattggaat atgctcatag agcaaagaac atattgaata agcctgaagt gaatcagaaa  24060
ctcaccaaaa aagctcttat taaggtaact gtgaattttt gtagagtaat gtaatcttgt  24120
ttgacaaatg tgaaaataag aaactgaagt gggagataat agttaaacaa gatttgttaa  24180
attgcccatg gaaggctttt tatatagtga tttaaactaa atgtcttaca tgttaacata  24240
ttttttctta atgctagtat gttgacttta ccaactttat caactgagtt ggtactctta  24300
gcaaaatttt catttattta catttacaaa atttatttat ttgcattttt gaggtataat  24360
ttacatgcca taacatccac ctaatgtaag catacaattc aatgatttat agtgcattta  24420
cagagttgtg gagtataacc acgatctagt tttagaaaat ttgttatcac tatccagttt  24480
ccctttgctc ctttacaatc atgtggccac tgacctgctt tctgtctaca gatttgcctt  24540
ttctggacgt ttcctataaa tggaatcatg taatatttgg tcttttgcat ctagtttctt  24600
ttgcctagca taaccatttg gggttccact tataacatgt atcagtagtt tatttctttt  24660
tattgctgaa tagtattcaa ttatatgctg ataatatgac atttggatca tttccactaa  24720
tgccattgtg aacatttctg tacatgtctt tgtgttgatg tgttttcatt tcttttgggt  24780
agatatctag ggatttaatt tctgggttgt atagtaagtt tatgctctaa gaaacttttc  24840
catgtagctg taccactttg tatttcctac agcagtttat gaggtctgca atttctccac  24900
ctcctcttta acacttgtta tggtcggtct ttttaatttt aaccattcta aggagtataa  24960
aatggtactt cagtacggtt tttttgtttt tgtttttgtt tttttttttg agatgaagtc  25020
tcgctctttc acccaggctg gagtgcagtg gcacgatctt gactcagtgc aacctccgcc  25080
tcccaggttc aagtgattct tcgacctcag tctcccgagt agctgggact acaggtgtgc  25140
accaccacgt ctagctaatt tttgtacttt tagtagagat ggggtttcac catgttggcc  25200
aggctggtct tgaactcctg acctcgtaat ctgcccgcct cagcctccca aaatgctggg  25260
atcacaggcg tgagccaata cgcctggccc caatatggtt ttaattagca tttccctaat  25320
```

-continued

```
gactaatgat gttgaacatc ttttcttgtg cttattatct atttgtttat ctttttttggt  25380
gaaatgtcta ttcaaatgct ttgcccaatt ttaattggtt tgtcttatta agttgtaagg  25440
agttcatgta gtctagatac aagcccttaa tgagatatga tttgcaaata tttcctccca  25500
gtctggcttt actttttcct ttccttgatg tttttttttt ttttaaataa agtttttagt  25560
attgagatga ttatagattc acatgcagtt ataagaaata atacagagaa aacaggccag  25620
gcacggtggc tcatgcctgt aatcccagca ctttgggagg ccgaggtagg cggattgctt  25680
tagatcagga gttcgagacc agcctggcta acatagtgaa accctcatct ctactaaaaa  25740
tacaaaaatt agctgagcgt agtggcacgt gcctgtaatc ccagttactc aggaggctga  25800
gacaggagaa ttgcttgaac tcgggagaca ggttgcagtg agctgagatc gagccactgt  25860
actacagcct gggagacaga gtgaggctct gtctcaaaaa aaaaaaaaag aaaaaaagta  25920
ataatacaga gaaatccttt gtacattttg ttgaactata gaatattacc acggggatat  25980
tgatattaat aacaatccac taatctttcc caattttcct tacatgtgta tgtgtattta  26040
attctagaca gttttgtcac atgtataggt tcatgtattt accaccacaa tcaagatact  26100
gaacagttcc atcaccacga ggacccttca tattgctctt ttgtaaccac ttttcttccc  26160
accatatcct tcctttcctg gtacccagta acctgtcctc tatcatttca agactgttat  26220
tgattggaat catacattat gtaaacgttt gagattgcct tatttattta tttatttatt  26280
tattttgaga tggagtctca ctctgttgcc caggctggag tgcagtggtg cgatctcagc  26340
tcacagcaac ctccgcctcc cgggttcaag cgattctcct tcctcactct cccaagtagc  26400
tgggattaca ggtgtttgcc accatgtcca gataattttt tgtattttta gtagagacgg  26460
ggtttcacca tgttcgccag gctgggtctc aaactcttga ccttgtgatc cacccacctt  26520
ggcctcccaa agtgctggga ttacaggctt gagccactgc acccagcaga tctttctttt  26580
ttagtactaa gtagtagtcc atggtgagta tgtaccatac atacagtttt tgtaaccatt  26640
cacttattga ataacatatg agctaatttc agtttttctg ctattacaaa caaaactgct  26700
attgacattc atttataggt atttatgtaa acataaattt ttatttctct gggataattg  26760
cccaagagtg caattgctgg gttgtataat aattgaatgt ttattatttt agggaactgc  26820
ctgtttttca aattggctgt atcattttac agtgtatgag tgatctgatt tcttcacatc  26880
ctcaccagca tttggtggtg taactttttt attttagtca ttctgatagg tgtggtaggt  26940
gatagatatc tcattgtggt ttttaacttg aatttttcta aaggctaatg atgttgagtg  27000
tctttttaat gtgcttattt gatgtttata tatttatgta tatatagcat atacatatat  27060
tgcatattta tatataacat atacatgtat atatatattt atttcccatt ataatttatt  27120
tggggaaata tctgtatatt tgtcctgtag agttttacca tagtatcttt tgacgtgttc  27180
ctctgttctt tgtattttct ttgtaaatcg gtagctgaat cttgaggctt gattaaattc  27240
aagttttgtc ttatttattt ttggcaaaac taattcataa gcagtagtgt cttcttccat  27300
ttagaagtat gtaatgtctg gttctttgtc tttttttttt tttttttttt gagacggagt  27360
ctcgctctgt tgcccaggct agagtgcagt ggtgccatct cggctcactg caagcttcac  27420
ctcctgggtt cacaccattc tcctgcctta gcctcctgag tagctgggac tacaggcgcc  27480
tgtcaccacg cccggctaat tttttgtatt tttagtagag acagggtttc accatgttag  27540
ccaggatagt cttgatctcc tgaccttgtg atccgcccgc ctcggcctcc caaagtgctg  27600
ggattacagg cgtgagccac cgcgtccggc cagaggtata gttcttatag gaaaggcagg  27660
```

-continued

```
acacatgctt gattaatttc ctttatttgc caattttgag aataatgagt tggtttccta  27720
ggtttcttag tgtcattata aactcctaga tttaaactat ttgtgttaac ccattgtagt  27780
tgttctcctc accgatgctc agattggctc atcttaggcc aggggtatgt tagtctgttt  27840
tcatgctgct gataaagaca tacccgagac tgggcaattt acaaaagaaa gaggtttatt  27900
ggacttatag ttccacatgt ctggggaggc ctcataatca tggcggaagg caaggacgag  27960
caagtcacat cttacgtggg tggcagcagg caaagagaga gagcttgtgt ggagaaactc  28020
ctgtttgtaa aaccatcaga tctcgtgaga cccattccct gtaatgagaa cagcatggaa  28080
aagatccgcc cctacgattc agtcatctcc caccaggtcc ctcccgcaac gcgtgggaat  28140
tatgggagct acaagatgag atttaggtgg ggacacagag ccaaaccata ttaaggggtt  28200
acatcttcaa gtggcttact gagtcctttt gattaaccta gtaggctttg cttagcttat  28260
ttccttgtct tatttgacaa gatgttccgt attcatcttg aatattttct gcctcagtcc  28320
tggaatcaga tgcttttata aggaatcctg gttcatttta gtgtgaatta ctcctaccaa  28380
cctgggtact ggaggttgtg gtttttcttg ggaagtccat atttctagaa tgagtgtatt  28440
taaaaaggag ctttgaaaga ctttatttct aaacaaatta atattgatta aaaagtatgg  28500
ttataacttt ttatcatact tctttaagtt ttaaaagaca taaaaaggct aactttacat  28560
tttatttgtt gcatgtcctt cccaaactga atgaaaaaag tactaaactg acacctacaa  28620
cattcctctt gtgtaggagt atacggagga gatagaacgt ttaaaacgag atcttgctgc  28680
agcccgtgag aaaaatggag tgtatatttc tgaagaaaat tttaggtaag cccttggcta  28740
tggagttaat ttccaagaat aagcatttct gataacaggc tatttgaagt aaaacttatg  28800
tagcagtaag taaaatcttt atatccagtg ccgataaata cttcattttg tgtgtgtgtg  28860
tgttttcttt tgagacaagg tctcgcactg tcacccagac tggagcacag tggcacaatc  28920
ttggctcact acgtcctcag tctcctgggc tcaagcgatc ctcctgcctc agcctcccaa  28980
gtagctggga ttataggcat gagccaccac accctgctaa tttttgcatt tttttgtaga  29040
gacagggttt caccatgctg cctaggcttc tattttgttt tgacattaac aagtagctat  29100
caaacacttt ttaaaaatct tttactaact tttaattttt aaatcattaa ttcatgtgaa  29160
gtttcaagaa gagtacaaga gaggtttcat gtattcttca cccagtcttc ctcagtggtt  29220
atctcttaaa taattatagt acaaggctgg atgtggtggc tcacacctgt gaatcccagc  29280
actttgggag gccaaggcag gcagatcacg tgaggttggg agtttgagat tagtctgacc  29340
aacatggaga aaccccatca ctactaaaaa cacaaaatta ccctgtgtgg tggtacatgc  29400
ccgtaatcat agctactcca gaggctgagg caggagaatt gcttgaagct gggaggcgga  29460
ggttgtggtg agccaagatc gcgccattgc actccagcct gggcaacaag agtgaaactc  29520
tgtctcaaaa ataagtaaat aaaataatag ataaataaaa aataggcgcg ataaataaaa  29580
aataggctgg gcgccgtggc tcacgcctgt aatcccagca ctttgggagg ctgaggcagg  29640
cagatcacct gaggtcagga gttcgagacc agcctggcca acatggtgaa accccgtctc  29700
tactaaaaat actaaaatta gccaggcatg gtggcaggtg cttgtaatcc cagctactcg  29760
ggaggctgag gcaggagaat cacttgaacc tgggaggcag aggttgcagt gagctgagat  29820
agcagcattg cactccagcc tggggaacaa gagcgagact tcatctcaaa aaagaaaaag  29880
gaaaaaataa taataaaata aataaaaaat aattatagta caatatcaaa gctgggaagt  29940
tgaccttgat acaatatgtg tattagtttg ttcttatact actatagaga accacctgag  30000
actgggtaat ttataaagaa aagaggttta attggctcac agttccatag gctgtacagg  30060
```

-continued

```
aggcatggct ggggaggctt caggaaactt acaatcctgg tagaagagct aaggagaagc  30120
aagcacatat tcacatggcg gcaggagaga gaaagtgaag aggaaagcac tgcacacttt  30180
taaacaacca gatcttgtga gaactcattc actatcatga gaacagcaag ggggaagtcc  30240
atctttatca ctcggttatc tcccatcagg tccctcctcc aacatgtggg gattataatt  30300
caacatgaga tttcagtggg gacagagaac cagaccatat caagatgtgt atatagtagt  30360
tctatgccat tttgtcactt gtatagattt gtgtaaccac cactgcaatc aagatacaga  30420
actatcctat catcacaagg atctttcttg ctaattcact gtagtcacac tcacctcatc  30480
ttttccatga ttcctaaccc ctggcaacca ctaatctgtt cactttttaa agccctggag  30540
taatttgttc aaaggaaagc ttttattgag gcccattgta taaaacaaca ataataacag  30600
agaaaacaag gggaagaagg caagtgggat gctaaggact ataacttgaa aattcctgat  30660
tgtgtttatc cttgaagata ttaggaagca agactttcac agagcatttt ttaaaagtta  30720
atagtgataa aagatattag acctaataat aaccagaagc attttagtat aatcttttac  30780
tgaacttttt tgtagatgtt aacactctaa tagtatataa atcatttaat aaacttagtt  30840
ttttctgtgt tacttccaac tgtcataatg tattccatga atgtgtaaga tgccctagaa  30900
tcagaacaat gtaagattgt gggttagtga acagtttacc atcactaatg gaggtgttct  30960
ttttttgatg ctttagaagt aaaaaaataat tggtgaggca ctcaatcctg gcctgtagtc  31020
tttagaaatg atattgatta ttggaggctt tcatctttct gattttattt ttgaacttaa  31080
gaagtaactt tggttttcat ttgtttagtc ccatgattga aaatatggtg tttgctctct  31140
tttttttaa cttttatttt agtttcagga gtacatgtgc agatttgttc tatagatata  31200
ttgcatgtaa caggagttgg tgtacatatt attttgtcac ccagataata accatagaac  31260
ccgatggata gcttttcaat ccttgctctc ctcttaccct ccaccctcaa agaggcccag  31320
gtgactattg ttcccttcct catgtccatg tctgctcagg gtttagctcc tacttataag  31380
tgagaacgtt tggtgtttgg ttttctgttc ctatgttagt ttgtttagga caatggcatc  31440
cagctccatc catgttgctg caaagaacat gatctcattc tttttttttt tttttttttt  31500
tcgagacagt cttgctctgt cacccaggct ggagtatagt ggtgtgatct cggctcactg  31560
caacctctgc ctcccaggtt caagtgattc tcctacccca gctgcccgag tagctgggat  31620
tacaagcacc tgccaccatg cccagcaaat tttttttttt ttaagtagag atggggtttc  31680
accatgcacc atgttggcca ggctggtctt gaattcctgg cctcaagtga tcaactcacc  31740
ttggtatcct ggcgtactgg gattacaggc atgtgccact gcacccagcc atcttgctct  31800
tttttatgcc tgtgtagtat tccatggtgt atatgtacca cattttcttt atccagtctg  31860
ctgtggatgg atagctaggt tgattccacg tctttgctgc tgtgaatagt gctatgatga  31920
acatatgtgt gcatgtgtct ttatggtaga acaatttata ttcctttggg tatataccca  31980
gtaatgggat tgctggctca aatagtattt ctgtgtgtgt gtggtttttt tttttttttg  32040
agatggagtc ttgctctgtt gtccagggtg gactgcagtg gcacaatctc ggctcactgc  32100
aaactctgcc ccccaggttc aagcaagtct cctacctccg cctcccaagt atctgggatt  32160
ataggcaccc accaccgcac ctggctaatt tttgtatttt tagtagagat ggggtttcac  32220
catgttggcc aggctggtct cgaactcctg acctcaagtg atctgcccac ctcggcctcc  32280
caaagtgctg gattacaggt gtgagccacc atgccctgcc ggtatttctg ttttaagttc  32340
tttgagaagt cgccaaacta ctttccataa tggctgaact aattttcatt agtagcatat  32400
```

-continued

```
aagcgttccc ttttctccac aactttatca ccatgtgtta ttttttgact ttttaataat  32460
agccattctg actggtgaga tggtttctca ttgtggtttt gatttgcatt tctctaacaa  32520
ttaatggtgt taaacatagt ttcatatgct tcttagccac atatatgtct tcttttgaaa  32580
aatgtccaca tcatttgccc actttttttt ttttttttga gacacagttt cactgttgcc  32640
caggctggag tgcagtgtgg cacgatctca gctcacttca acctccacct cctgggttca  32700
agcgattctc ctgcctcagc ctccgaagta gctgggatta caggtgcctg ccaccatgcc  32760
cggctaattt ttgtattttt agtagagatg ggatttcacc atgttggcca ggctggtctt  32820
gaattcctga cctcaagtga tctgcccacc tccgcctccc aaactgctgg gattacaggt  32880
gttagctacc gtgccccgct gggtgtatat gattttatac ttagaaaacc ccatagtctc  32940
tgtccataag ctcctagatc tgatcaacaa tttaagcaga gtttctggat acacaatcat  33000
tgtactaaaa tcagtagcat tcctatatac caataatgtc caagctgagt gccaaacaag  33060
aatgcaattc cattcacaat agccacaaaa acagtaaaat acctaggaat acaactaacc  33120
agagaggtga aggatctcta cggtaagaat tataaaacac tgctgaaaga aatcagagtt  33180
gacactaaca aatggaaaaa ctttccatgc tcatggataa gaagaatcaa tattgttaaa  33240
atggccatac cacccaaagc tatttacaga ttaaatgctg ttcctctcaa actaccaatg  33300
acattcttca cagaaaaaac tattgtaaaa ttcatgtgga actggaaaag agcccaaata  33360
gccaaagcag tcctaagcaa aaagaacaaa gctggaggca tcgcattacc tgacttcaaa  33420
ctatactaca gggctacagt aaccaaaaca tcatggtact ggtacaaaaa cagacacaga  33480
ccaatggaac cgaatagaga gcccagaaat aaagccacac acctacagcc atctgatctt  33540
cgacagaaca tgcaatgggg ataaaactgc ctgttcaata aatggtgctg ggataactgc  33600
ctatccatgt gcagaatatt gaaactggac cccttcctta acgcccatat acagaaatca  33660
actcaagatg gattaaaaac ttaaatgtaa aacctaaaac taaaaaccct tgtaaaaaac  33720
ctaggtgttt gttctctaat acacatgagg cataatctga gatagttttg tctgaaaacg  33780
cttttggaat tagtacagtg tcagtcagag aagaatcaca aaaactacag ccaacattta  33840
aaacaggata atgctttatt taagccaagc ttaatagaca ttttaaaacc atatcaaaat  33900
catctcatcc atacagtaac aatgttgtat taccccttgg cattcactat aaaaaagcat  33960
ttcaaataat cccgttttac ataaaagatc tatttctatt tattttattt tatttttatt  34020
tttatttttg agacagagtc tcactctgtc acccaggctg gagtgcagtg gcgccatctt  34080
ggctcactgc aagctccgcc tcctgggttc acgccattct ctcgcctcag cctcctgagt  34140
agctgggact acaggtgccc gccaccacgc cctgctaatt ttgtttttgt attttagtag  34200
agacagggtt tcaccatgtt agccaggatg gtcttgatct gctgacttcg tgatcttccc  34260
gcctcggcct cccaaagtgc taggattaca ggcgtgagcc accgcgcctg gctgtagaag  34320
atccattttt aataaaaagc taatatattt catcaaaaga ctattagaat taactcttct  34380
cttacagctc ttttctagct tttcctttag tcaacaatat ctctagctaa tacgttaagg  34440
gaatttgtat tcacggaaga atctttgtca tttaagcata atgtgaaata gaaaattgtt  34500
ggttgttatc aaagaattag atgagcaaat acaggcattc atttctgaaa ctgactaata  34560
ctcaagaaat cagagaccca ttaaagtggg tttggaagac ctgtgagctt tgcgcttgag  34620
aaaagcattc tctattttac tttttatgac ttcttttgac tttgacttca tcttctgata  34680
tttttgttga atttagaaat ttttagtttc taaaaactct tttctgccat ccctgtctct  34740
ccttttgaaa aatatagcat ccttttattt tatagatcta ttccttatct cagaaacatt  34800
```

```
attaatgtta ttaaagtttt cttttatgtt tttctttcct ttgggatctt ttttttccct  34860
gttgtgatat ctgtcatttg tatttatttt cttcaaatgt ctagtgattt ttggctggca  34920
attaagatgg attagaagct ttgtacatgg gtgaggatta tggacctgta agttcactat  34980
agatgaaaaa gtggtgatct cagtcttaag tctgggcttc catcagatat cattctttgt  35040
tggatttttt ttcttttgtt ctagccctca gtcttttctg agaagatttg cccagtttgc  35100
ttggagattt ttctagctgc tgctattttt tgattagagt gggtataggg ggctgaggat  35160
tccatcattt tgtatgtaga tttacactta aatgctcatt tctagtccct aaaccttcta  35220
cagtccatga tgtctagtga aagtgaacct ggaaattctg ctgcaattcc tatagactag  35280
tggctgtcaa tggaagtggt gttgggggac tggtggtggt gggtggtttt gtcccccaga  35340
ggacatttgg cagagtccag tgacattttt tatcatcatg acttggatgg tactgaacat  35400
cctaaaatgt acaggacatc cccacaatga agaattattt gatccactag tgctgaggct  35460
gagaaactct gctctagaga gtaatccttt gttctcatga gggttatgcg gtggggtgag  35520
agtggtgttt gtgcgtgttg cagcagcagg gggtgtaatt gctctgtata catactttaa  35580
gtctcagttt ttaaccccta atcttacccc ttccttctaa gatacctgat gccttcaagt  35640
cccacatttt tccagcattc tgtggggcat atttatattc tgtatccctg attatagaca  35700
cttaggttgc attccctcct ctctctactt tgagttatag tccgtcctct gttagctttc  35760
tagcttctca aatctggaac acacatgctt ttcccctcat aggtagggat tcttagtttc  35820
agaattgagg gcaagggaaa aatatttcat ttataaaaca aagacaagga atataatttg  35880
ttctttgtaa tttgtattta ttgcttattg acacaggtat caagtgacac ttgggtatca  35940
agtgatggtg ataaatgttg gaaatgagtt tgtgtagctg tcacaattgt gttagaatac  36000
attttatagg agttagaaaa aaatattaac tgttaaactc atattaaact ttattttaga  36060
gtcatgagtg gaaaattaac tgttcaagaa gagcagattg tagaattgat tgaaaaaatt  36120
ggtgctgttg aggaggagct gaatagggta agcacttaaa atgatattta ctgttatgtg  36180
aaaagcaaat attgaaagaa aattttagaa tgaaagatct aatatttttt ccttcaagat  36240
tttttttttt tagacggagt ctcgctctgt cacccaggct ggagtgcaat agcgtgatct  36300
cggctcactg taacctctgc ctcccagggt caagcgattc tcctgcctca gcctcccgag  36360
tagctgggat tacaggtgtg caccaccatg cctggctaat tttttttgta tttttagtag  36420
agacagggtt tcaccatgct ggccaggctg gtcttgaact cctgacctca tgatctgccc  36480
atctcagcct cccaaaatgc tgggatgaca ggcgtgagcc actgcaccca gctccttcag  36540
attttttttgg aaaaaaaaaa aagattttat tttgctgacc cttatactga aagtaagtta  36600
tatcatgatt ttttactatc attaatcaca tcaaaaaagc tgacagctta tattaataaa  36660
acattacaag aaattaactg aattgtttga ttttgttatt gaaactacaa aatagtgaat  36720
gctgaagcag ttttgttaac atgtttatca gatgaaggaa tacagatatt gggagagact  36780
ggatgttaaa taaaagtaat ataactaggg taggcaagag gcctgacctt tcagggccac  36840
cctcatatta atacctttat ttatttattt ttaattattt tttagagaca gggtcttgct  36900
tgatgcccag gctacagtgc agtggtgtaa tcatatctta ctgcagcctc aaacttctgg  36960
tctcaagcaa ctctcctgcc tcagcctcct gagtagctgg acttcaggca tgcactacca  37020
tgcccggcta attattttat ttttttgtag agatggagtc agtctcgcta tgttgcccag  37080
gctggtctca aactatgggg ctcaagtgat ctcctgcctt ggcctcccag agtgctgggg  37140
```

-continued

```
ttacaggtgt gaaccacctt gccaggccac attaacactg ttatattcaa atccattgac  37200
aatgttgaag gaaactgaag aattaatagt actacaccag acctattatt taatctcaaa  37260
gtgttgagta agattacaga aagaaacagg atgacatatt tgtgttaacc taccgggtaa  37320
cttcttacaa cttttgcatg gaaataattt gtttcatttt tctaatctta tgaactagct  37380
agatatccta ccagccagct cagcgttttt taaattctta tatttaggtt acagagttgt  37440
ttatggataa taaaaatgaa cttgaccagt gtaaatctga cctgcaaaat aaaacacaag  37500
aacttgaaac cactcaaaaa catttgcaag aaactaaatt acaacttgtt aaagaagaat  37560
atatcacatc agctttggaa agtactgagg agaaacttca tgatgctgcc agcaaggttt  37620
gtcccttgtg ttgatttgta ctcatattaa gtagagaatg ggtagaaaaa atttctgtg  37680
cttaagcatt aaatattctg tttattcacc ccaaatggta tttctgtcca tttaaaaaac  37740
attattttac tatttcatcc atgtttttct cactggagat gtcgacttat gaaaaaacta  37800
ctcctgctcc tggagttttg aaaatagaac ataacttagc tgggagtggt ggctcacgcc  37860
tataatccca gcattttggg aggccaaggt gggtggatga cctgaggtca ggtgttcgag  37920
accagcctga ccaacatgga gaaacctgtc tctactaaaa atacaaaatt agccgggcgt  37980
ggtggcgcat gcctgtaatc ccagctactc gggaaggctg aggtggaaga atcacttgaa  38040
cccgggaggc agaggttgcg gtgagccgaa atcacaccat tgcactccag cctgggcaac  38100
aagagcgaaa ctccgtctca aaaaaaaaaa aaaaaaagaa aatagaacat aactttataa  38160
tatattttgt agacatttag aatagtgatg ctgtgatgct ttttctttgt ggggatgatt  38220
gaacctaatt agtcattaag aatttagtat gttctgtcca ggcatggtgg ctcacgcctg  38280
taatcccagc actttgggag gccgaggtgg gtggattgct tgaggttagg agttcgagac  38340
cagcctgacc aacatggtaa aaccccatct ctactaaaaa aaaaaaaata caaaaattag  38400
ccaggcgtgg tggcacatgc ctataatccc atctactcag gaggctgagg caagagaatc  38460
acttgaaccc aggaggcaga ggttgcagtg aaccgagatc atgccactgc actccagcct  38520
gggtaacaga gcaagactct gtttcagaaa aaaaaaaaaa aagaatttag tatgttctga  38580
tgatgaaaga tgttgaaagt atttaatttt tttttttttt ttttgagacg gagtctcgct  38640
ctgtcgccca ggccggactg cggactgcag tggcgcaatc tcggctcact gcaagctccg  38700
cttcccgggt tcacgccatt ctcctgcctc agcctcccga gtagctggga ctacaggcgc  38760
ccgccaccgc gcccggctaa tttttgtat ttttagtaga gacggggttt caccttgtta  38820
gccaggatgg tctcgatctc ctgacctcat gatccaccca cctcggcctc ccaaagtgct  38880
gggattacag gcgtgagcca ccgcgcccgg cctttaattt tttattagtt gtactttttt  38940
tttttgagac agactcttgc tttgtagccc aggctggagt gcagtggcat catctcagtt  39000
cactgtaacc tttgcctccc gggttcaagc gattctcccg cctcagcctc ccaagtagct  39060
gggattacaa gcgcctgcca ccacacccag ctaattttgt atttttagta gagactgggt  39120
ttcaccatgt tggccaggct ggtctcaaac tcctgacctc aggtgatcca cctgcctagg  39180
cctcccagag cgttgggatt acaggtgtaa gccaccacgt ccggccatta ggtgtacttc  39240
tgaggaaata gtagaacata gaaggaaaaa aatttctgag gaagcataat tattgcaata  39300
actgaaaaaa tcagttttcc ttgcttgtgt agatggctac aggaagggaa ataaacatta  39360
ctgggcatct ggataaatta gcatgagtta aagcatttct tctgatacaa tgtctaaaat  39420
tgactttttt tttttgagac agagtctctc tctgtcaccc cggctggagt ggcagtggca  39480
caatctctgg ctcactgcaa cctccacctc ccaggttcaa gcaattctcc tgcctcagcc  39540
```

-continued

```
tcttgagtag ctggaactac aagtatgtac caccacaccc agctaatttt tgtattttta  39600
gtagagacgg ggtttcacca tgttggccag gctggaaaat ttactagttc ttatcaagat  39660
aaatccttgt gtagatactt tcatcagatt cctttcaccg tatccatttt gtctaacact  39720
tatttttaaa aatatagctg cttaacacag ttgaagaaac tacaaaagat gtatctggtc  39780
tccattccaa actggatcgt aagaaggcag ttgaccaaca caatgcagaa gctcaggata  39840
tttttggcaa aaacctgaat agtctgttta ataatatgga agaattaatt aaggatggca  39900
gctcaaagca aaaggccatg ctagaagtac ataagacctt atttggtaag ttcaggctgt  39960
tctgttctag tcttgatgtg ttaagtgtaa tgttgatttc aaaactgata attttgtgaa  40020
acatagatga cggtgtcacc aatactctct accatgcaca aactatttgt tcagggtgaa  40080
gattaatgct tttattgtct ttgaattaaa acaaatcttt tttccctccc caccctccct  40140
tctgttttct ataaaatgtt acatttatta agtaactaag tatataaacg ttagaagtag  40200
aagtcctctt tttccctgac tccggctcct gaccctgggt cattgaccat aggtgttatt  40260
gttaaatttc ttgggccttt ttctggaaat tttttgtgca taaacattct gcaacttttt  40320
ttgggggggg catatatatc ttgatggttt gctatattgt cagaatatgt ttgtgtctca  40380
ttgtttttaa ctattatctc cctttagaaa aaagtatgtt tatttagtgt gaaatactat  40440
cctcattatg gaaaatttgg acattcagaa atataaaaat ttaaaaaaatc atctagactc  40500
tagtctcact aagccaagca ctatactttt tggtattgat ttccagtttt ttttttcttc  40560
tgtaaactta ccataattct gtatattatt tttagttaga gattaattgt agaatattct  40620
aattctttgt gtactatgaa ttatagttat gggtctgata cacttacaaa tatgttaagg  40680
gcttacagag cactatagaa aattgtaatg tatatttaaa tatttccttg ctttgtagtg  40740
agccagttct tttaagctcg ttattacaaa ttctacaaca agggtatact tttgtcaact  40800
tctttgaaat ggtttgaacg gtatttaata tatttatgtc aaagtttaca tctttctgtt  40860
tttgtttgtt ataggtaatc tgctgtcttc cagtgtctct gcattagata ccattactac  40920
agtagcactt ggatctctca catctattcc agaaaatgtg tctactcatg tttctcagat  40980
ttttaatatg atactaaaag aacaatcatt agcagcagaa agtaaaactg tactacagga  41040
attgattgtt agtacatcct ttaaaatatt tttgaagggt tgcatttgat aagtatttga  41100
taaaatattt tgaagggtta catttgataa gtctttataa acaatgttaa ctgctattct  41160
ttcttcctga gctttactag acacagtcat agacacgtca ctgtgagaga ctacatatat  41220
atatattttg ttttgttttg ttttgtttgt ttgttttgag atggagtctc gctctgtcgt  41280
ccaggagtgc agtggcgtga tctcggctca ctgcaagctc tacctcccgg gttcatgcca  41340
ttctcctgcc ttagcctccc gagtagctgg gactacaggc gcccaccacc acacccggct  41400
aatttttttgt atttttagta gagatggggt ttcaccgtgt tagccaggat ggtcttgatc  41460
tcctgacctt gtgatccacc cgcctcggcc tcccaaagtg ctgggattac aggcatgagc  41520
caccgtgccc agccagcctc tccttttctt tatttgtatt tatttatttt tttcagcctc  41580
tccttttctc ggctcactgc aacctctgcc tcctgggttc aagcagttct cttgcctcag  41640
cctcccgggt agatggaatt ataggcatgt gccaccacgc ctggctaatt ttcgtatttt  41700
tttttagtag agatggtgtt ttaccatgtt ggtcaggctg gtctcaagct cctaacctca  41760
agcaatccac ccacctcggc ctcccaaagc gctgggatta caggcgtgag ccaccgtgcc  41820
cggccgagag tacgtttata tttttaaaga cagatctctc cactgtttat tctctcccag  41880
```

-continued

```
aaagattatt ttcaaatgta tggaactaac ttttgaaacc tttttcactc atgtcttgta  41940
acattaggag tagcagttat tagtgaggct tctaatgact aaagggcaag tttagcacca  42000
catgatatca agggacttgt tagttggccc agaaattggc aagtcactct ttccccaggg  42060
gtcctggacc caaccagaag ggatattgg gtagctgatt ttaaaactac agtaatatat  42120
gatagtaata atggtgcaag aaaaatatct tagaattctg gggacacata tcacttctta  42180
gggttagatc tgtgtggccc cttctgggcc ataactataa atcttttctc cagagttcta  42240
tggaagtcac tcatctaatt gcacttaata ttacctcctt catacttgat ttatatatag  42300
tctttatttt ataattgtat ggttggtcta ggaagttctt agccatataa tttatttgtt  42360
ttctttgtgc agagtctttg cctccctttt tcagcttaac aatatttatt aaacattttc  42420
caagtaaata ctacaaatgt tagctgaccc tctgcctcaa ttcagtgctt agatgacatt  42480
atttgatagg ttttctcaat cacccaaatt tgacaaaatt aaaagatatc ctgtcagtac  42540
taacttttca aatattgatt cattcattaa atggtggtct gtatatatat aggcatactt  42600
cagagatatt gcaggtttgc ttccagacca ctgcaataaa gtgaatatta caataaagca  42660
agtcatgaat tttttgcttt cccggtgcat ataaaggtta tgttgaccag gcgcagtggc  42720
tcacacctgt aattccagca cacgcctggt gggacaatca gaacacaacg tttatcagtt  42780
acatttgctg tcttataggg gtacagttta tggtacccca agacaattac aatagtaaca  42840
tcaaagatca ttgatcacag tgtataatga aaaagttaga aatactgtag tagttaccaa  42900
catgtgatgc agagacagaa agtgagcaca tgatatttga aaaaagtcac tgatagacgt  42960
gctcaaggta gggttgccac aaaccttcaa tttgtaaaaa tttggtatct gtgacacata  43020
gtaaggtgaa gcacaataaa ataagctatg cctgaattga tacatttcta cttaccaagt  43080
tacaattttt gcttgaatta aaagaaaaga ggcatgttgc tctcacaaaa ttagttgaaa  43140
ttggtatgct agctcttctt tccaaaagaa tgtcagtaga cctataagta tttactaatg  43200
tatttctgtt atacttcctc agccctatcc taccaaaagg agattagatc aggatttttt  43260
ttctttttat aaatatttcc aatctatact acattcttaa tttccctatt tcttgacaag  43320
aacaacatct ttcacaagtt cttctgatac aataggatgt aagtcatctc agatcttcaa  43380
agttaagtac ttccagccca agggctaatc ttgatgacta cttggtctca gcctttttga  43440
ctggtaacct aaacttgttt gaaatttatt ttcttaaaat atacctgtag gtttttaaaa  43500
atttattttg tttggagtgc tgaaatctta ttaactgtca ttttcctctt ttgaattctt  43560
ctgacttcta tttcattaaa ctattaaata gttctggctg ggtgcggtgg ctcatctcag  43620
cactttggga ggccaaggtg ggtggatcac ttgaggtcag gagttcgaga ccagcctggc  43680
caacatggtg aaaccctgtc tttactgaaa tacaaacatt agctaggcgt ggtagcaggt  43740
gcctgtaatc ccagctactt gggaggctga ggcaggtgaa tcgcttgaac ccaggaggcg  43800
gaggttgcag tgagccaaga tcacgccatt gcactccagc ctgggccacg agagtgaaac  43860
tatatctcaa aaaaagaaaa aaagaaattc tgtgttttca ctgggcttga aaaaagagaa  43920
attattatat ttattgtaat ataataaatt attgtattat tgtattgatt tatctatgta  43980
gagtataaaa aatggagaat ggggccgggc gcggtggctc acgcctgtaa tctcagcact  44040
ttgggaggcc acgggggcgg gatcacctga ggtcaggagt tccagaccag cctggccaac  44100
atggcgaaac cccatctcta ctaaaaatac aaaaattagc tgggtgtggt ggctcacacc  44160
tataatccca gctactccgg aggctgaggc aggagaatca cttgaaccca ggaggcagag  44220
gttgcagtga gccaagatgt tgccactgta ctccaacctg ggtgacagaa tgagactccg  44280
```

-continued

```
tctcaaaaaa aaaaaaaaaa aaaaagaatg gagaatggaa atgtaaattt taatgtgaat  44340
gtttagctac caaagtattt aagatatcat ttagaaaggt ttacagaagt ggaaatattc  44400
tttttaaaga cctatttgtt tatttctgaa accagaatgt actcaagact gatcttctaa  44460
gttcactgga aatgatttta tccccaactg tggtgtctat actgaaaatc aatagtcaac  44520
taaagcatat tttcaagact tcattgacag tggccgataa ggtaacaaat gctatgttct  44580
taatatctca aaattgatgt gttgtttaag aaggaaactc atttttgttt cttcaaagat  44640
agaagatcaa aaaaaggaac tagatggctt tctcagtata ctgtgtaaca atctacatga  44700
actacaagaa aataccattt gttccttggt tgagtcacaa aagcaatgtg gaaacctaac  44760
tgaagacctg aagacaataa agcagaccca ttcccaggta tgttgtttag cggacttggg  44820
gagtacagaa agagagtttt aggatgattt gatatgactt gataattaat ctatgttaca  44880
caatctgaat actgtaaaag ctgaaacctg aaaataccat agccactgtt gcttataaca  44940
gtaattattg tagaacaatt gagaatactt ctcttaatat ttgaagtttt gctacatcta  45000
gaaccccatg cagaaccaca atatgacaaa acagtccttt tctcacatca agatgaaaga  45060
tgaatctgga aaaacatacc tttagagaag aatggttata acatttaaag tgaaaatgta  45120
tctacattaa aacctgctaa gttgtttcta ggatggcatg gatagttgtc tttcataaac  45180
caagtcctac tttctcttat ttctgtctca ctgatagaca tttaaaacat agtaaatcga  45240
tacaactttt aattcttatt gattataaat gtaattcatg atttatcttc cctgtaaact  45300
gttcctcatt atatgaggct ttaaaccaaa accaagcctt caaaccataa tctgtaaata  45360
tcagatatct gaaaaacagc ttctggtatt cttaagactt taataatgac tgtctaaagt  45420
tttattaaat gagcttatta taatatgaca gaactcttat aatagttaac atttattgag  45480
caattcactg tgtttattcc tcccatcaat atagatataa attctattac tagtcagatt  45540
tttaatgagg aaactgagac cctgtgagca tctaatagta tgtagatcat cttgcagaag  45600
gtggtagtga tcatactacc tgaaaagcat ccatgtttga gtggctcttt tgtgtgtttt  45660
ttggcaactt aaaactgcag cattttctca tacatctaca tagggtattt cccttaaacc  45720
cgttgagaac tttttaggtg tatattctaa ggctgatccc ctttttataa atttgctgtt  45780
ttgaaatgct taaaattgtt agacagctct ttaaaaaaac aatacaaaaa aatctgatct  45840
gaaaagtatc ttagcatgaa tggtttggct ttcctggctt taaggaagca agttcagtat  45900
gtgagctatt tcttaggttt tccagaactt gaaatgagca ctactaaaat aattatgtaa  45960
aactttgaac acatttacat atagataaat ataatacctg cattagcatt caaattatta  46020
atctgataat acctttgaga ctagtaaaaa tactgacaga ctttattcat aatcagaatg  46080
ttagatatgt attgtcaact gatgtgttat tcagagatac tggccaacca gcagactgaa  46140
gagtgaataa gaatgttgga tgcattttca gctcttcttt ggtcattagg atggcttctt  46200
cattttgcaa tgtagcatgt tatatgccta taagagcttg ttttcaaaga tgtaaaatat  46260
gagcaaagat aagactattt acattttgtt aatatgatcc aactaggttc tgtaacattt  46320
tttagctcca gtaattgata atatttttgg attgcttgac ccgttagtat atcacattaa  46380
ttttcccttc tagcagtgtt atcagttaaa aagcaactat atatatctgt caaagtgggt  46440
cttaaacata atgtgatata tgggttgttt gattagtttt gaggtacact gaaagtaatt  46500
tgttacttac agctaaaata gtaaagtttg ctaattattt actttttaaa aaatcctggc  46560
tggatgtgat ggctcatgtc tgtaatctca gcactttgag aggctgaggc agggtgatca  46620
```

-continued

```
cttgaggcta ggagttcaag accagcctgg tcaacatagc gagatcacgt ctctacaaaa  46680
aaaatttgtt taaattagcc aggcatggtg gctcatgcct gtgtagtccc aactacttgg  46740
aggctgagga aggaggatcc cttgagccca ggaggttgaa gctgcagtga gccttgattg  46800
tgccactgca ctacagcttg gacaacagag tgagaccctg tctctaaaaa aaaaaacaaa  46860
tcctacattt taatatcact tccactgctt tcctctgtag aagaaaggta aagttaactt  46920
tatctcttgt caagaattta tataattctc acctatggac aatacttctt gttttgttat  46980
cagtcataaa aaatgttcaa gtgtcataat tttaagtctc ttcacttccc acacctttct  47040
tacaggaact ttgcaagtta atgaatcttt ggacagagag attctgtgct ttggaggaaa  47100
agtgtgaaaa tatacagaaa ccacttagta gtgtccagga aaatatacag cagtaagcta  47160
tttttaaatt ctcttaaact tttctgtaag tctgaaatta tttaagaaga aaaagcttta  47220
aatagtacaa ataattcctc tgtgtacttt caaatttctc ttttgttaat attttattat  47280
gtatgtgtgt atgtatatat atacatgcat ataaatgtct tttcattgcg tatttgtgct  47340
ctcttttaag acattgaaaa acctggctgt tacccacaat atattttcga atttcctcaa  47400
tcttagaaaa cacactaagt aatttcacaa tttctaacct atattactga tgaaaaatat  47460
actaactaga gcagggtttg gcaaactgtg gctagcaggc tggatgcctg ttattgcaaa  47520
taatttcatt ggacactgtt tacatgttgt ctttggctgc ctttgcactg cagtggcaaa  47580
gttgagtcat tgcatccagg tcattgaaca atagcctaaa atatttgcta tctggctttt  47640
caagaaaaag tttgctgatt cctgtattag ggttttgttt tttgtttttg tttttgtttt  47700
tgcgacggag tcttgctctg tcacccaggc tggagtgcag tggagtgatc tcagctcact  47760
gcaagctccg ccttccaggc tcacgccatt ctcctgcctc agcctcccga gtagctggga  47820
ctacagatgc ccgccaccat gcttggctaa tttttttgtat ttttagtaga gaggggtttc  47880
accatgttag ccaggatggt ctcgatctcc tgacctcgtg atccgcccgc ctcggcctcc  47940
caaagtgctg ggattgcagg cgtgagccac cacgcccggc tctgttttgt tttttcagac  48000
aaaaacaaac agcctgctct gtagcccagg ctgaagtaca gtggcgcgag tgcagtggtg  48060
tgatcttggc tcactgcaac ctctgcctcc tgagttcaag tgattctcct gcctcagcct  48120
cccgagtagc tgggattaca ggcacatacc accatgcctg gctaattttt tgtattttta  48180
gtagagatgg ggtttcgcca cgttggccag gctgatcttg aactcctggt ctcaactgat  48240
cctcctacct cggcctccca aagtgctggg attgcaggtg tgagtcactg ctcccagcct  48300
gtattagagt ttaatgttgc tttgtagcct cattgcttgc cagttccgca tacttaacat  48360
acactacagt cagacctatg ttttctttta ggaattttat aactttatgg tttaacattt  48420
atattcatga tccatttaaa aatttttata aaacatagga gatttgtcaa gtttcagttt  48480
tttgcctatt gagtattcta tactcatgag gagaaagata ctatatttac cctatttttc  48540
cccatttaat tctgaaatta aacttcctaa agtttcaagc tttctttggt gggaagtagt  48600
ctttaagggt gggtctgctg gacagaaatt gtttttcttt gtctaagaat gtcttgattt  48660
ccccttcatt cctgaaaggt attttcactg gctgtggaat tcagggttga caattatttt  48720
tttccagcat ttgaaatatt tccattttct tctggcctct atgaaatgag aaatccactg  48780
ccattcaagt aattgttccc ttataggcag tctccctata gctgctttca aaactttttt  48840
gtctttagaa acttgattat attttgtcta cttatatttc gttgagttta ttctatttgg  48900
gttttgttta gcttcttgaa tctgtaggct tatgcctttc accaaaactt gggaaatttt  48960
catctattaa ttctttgaat atttttcagc cctatactct ttttcatctg cccctatgac  49020
```

```
tttgatgaca caaatgttag atcttttatt ttggtccctc aggagatatg tagaatatat  49080
ttcttataga tacatatatt ctctttgttg ttcacattgg ggaaattcta ttgatctgtc  49140
ttcatattca ctgagtctcc ttctgtcatc tctaacctac tgttaaaccc attcaatgag  49200
gtgtttttc agttattgct tttttatttt tagttttata attttcattt gcttttttta  49260
taccttgttt cttagctagg attttttct tttccaggag tattttaatt tctttttgga  49320
gcatttttg atggctgctt taaaatcctt gccagacaat tccaacatct gagttttctt  49380
gttgttgcca tctattgatt gtcttttctc attcaacttg tgatttttgt ggttcttgat  49440
atatgataag tgatttccta ttgtaccttg aagattttgg gtattatgtt aggagattca  49500
ggatcctatt taagtatttt ttagctggca ttcaccctgt ttaggcttag catacagatc  49560
caggctcact tttatgggct gtggttccac tgacaattta gtttttagag cccttgcagt  49620
gttattctga taatgctttg tttgtgtgct acccacatga gaaaaatttg tattctgctt  49680
ttgttgcatg aagtgttctg tatgtgtcac tttgatcaag ttgattgata gtgctattca  49740
ggtcatccac ggccttactg agtttctgcc tatttgttct atcagtgact tagagaggag  49800
tattgaaatc tctaattgta gatttatcta tttttttat tagttctatc agtttttgcc  49860
tcgtgtatct gaaactctgt tgttgggtgc atatacattt aggattatta tatctccttg  49920
gagaattgac ctctttatca ttatgtaata tccactttta tttctgataa gctcttgttc  49980
tgaagtctgt tttgtctgaa atgaatacag gttttctagc tttcctttga ttgctatttg  50040
tatgatgtat ccttctccat ctctttactt ttggtctaag tctttatatt taaagtgggt  50100
ttcttataga cagcatgtag ttgggtcttg ctttttcatc aaatttataa tctatgatgt  50160
tttattttta tttatttatt tgagacagag tcttgctctg tggcccaggc cggagtacag  50220
tggtgcaatc ttggctcact gcaacctctg cctcccgggt tcaagtgatt ctcctgcctc  50280
agcctcctga gtagctgggg ctacaggcac acaccaccat gcccagctaa tttttaaatt  50340
tttactagag atggggtttc accatgttgg ccaggctggt ttcgaactcc tgacctcaag  50400
tgatttacct gccctggcct cccaaagtgc tgggattata ggtgtgaggc actgcaccca  50460
gctgcctttc ctcatttaaa ttgagcactt tttatgtttt tatctcttcc attgacttat  50520
ttatactttt taaatattcc ctttttagta gtatgtctag gatttaaagt atacatttta  50580
agataatttg aatttgtata cattttaaga taatttgaat ccattatcaa ataatttgct  50640
gtttcatgtg tagtgaaagg acattataat agtatattcc tgtttcctct ttcccgtttg  50700
tcattatttt catatgtttt acttaggtgt ttatatgtgc aataaacacc taatacattg  50760
ttacttgaat tgctttatct attttctttt ttaatgtatc tactagattt tttttttttt  50820
tttttgaga gggagtcttg gtctgtcacc caggctggag tgcagtggtg caatcttggc  50880
tcactgcaac ctctgcctcc caggttcaag caattctcct gcctcagcct cccaagtagc  50940
tgggattaca ggcacctacc accatgcccg gctaattttt gtatttttag tagagacggg  51000
ggtttcacca tattggccag gctagtctca aactcctgac cttgtgattg cccgcctcag  51060
aaatttttaa ttgcatatgt ggcttctatt atacttctgt tgaacagtgc tgttctggaa  51120
ctctagctat catttatata tccctaccta acttctgtca tttgtttttc aaccctgttt  51180
ttgatcctgt taagtatagc atgttccatt gtgaactctt cctatatgct gaatcaaaaa  51240
agtatgtcct actttttatt cctagtatct agactgatgg atttctaggc cattccatag  51300
ccgtggagga aatactagag taggattgaa gtaggaaggg aagtatgata tactttctta  51360
```

-continued

```
aggcccatgc aaatcatttt tcctgctttc ctgacattta ttgtctacac cagagtttcc  51420
cagtatggtc tagggacttt gtattcatca cccaggaatc taggtgatgt ttatgtacac  51480
actgcacata actgcgtttg gcatttattg tcatggctta tagtactttt aactcaatct  51540
cgtcttccca ttaagttgtg agattttgtt ttgttttttt tatttgagac agagtcttgc  51600
tctgtcgccc aggctggagt acaatgacac aatctcagct cactgcaacc tctgcctcct  51660
agggtcaacc aattctcctg cctcactctc tcccaagtag ctgagattac aggcacccac  51720
caccacgccc ggctaattta ttgtattttt aatagagaca gggcttcacc atattggccg  51780
gactggtctc taactcctga cctcaggtga tccacctgcc tcggcctccc aaagtgctgg  51840
gattagaggt gtgagccact atgccttgcc ctttttcag tcattgtgac tttcacgtgt  51900
aggtttggtt tttaacatct ttgctgactc acttggttta cccacgtggt gtaccatcta  51960
gtggtaatag agagtcactt cattccacaa ggtttaaatc ttgtaagata acttggaatg  52020
ctattatagg gcaacttacc gagatggaaa ttatcaatga attttaaatg tatgtctaac  52080
caacattaat attatatcaa gtttatgtta cattgttcta tatgtataat ttgtcacacc  52140
ccaatataat tttaattatt agaaagcttt atagctaatt taaacataac atttgtaatg  52200
ttcatgattt gttttacata ctaggcaagg gaaactgctt aataacagaa taaatgactg  52260
attgtccaat ttagggacta gacaagaggc tgtagtagat gccctgaagt aacattgcct  52320
agtaagagga ataaaacaag tagacagatt ttgaaagcat cataactgga ggagggttgt  52380
gaaaggtttc atgagcaaag atgatccttt caaaggtcat ttaatggcaa tgctgtgaaa  52440
agacagtggc caaggcatcc attctcaatg cagaagattt actaagatca cgggccctgg  52500
agccagactg tccacgttca gatctgccac ttaagagctg agtgatcttg ggaagttata  52560
tatcctttga gtcttaattc cccatttcaa cagtgtcatt ctcttttcct ataggaaatc  52620
taaggatata gtcaacaaaa tgacttttca cagtcaaaaa ttttgtgctg attctgatgg  52680
cttctcacag gaactcagaa attttaacca agaaggtaca aaattggttg aagaatctgt  52740
gaaacactct gataaactca atggcaacct ggaaaaaaata tctcaagaga ctgaacagag  52800
atgtgaatct ctgaacacaa gaacagttta tttttctgaa cagtgggtat cttccttaaa  52860
tgaaagggaa caggaacttc acaacttatt ggaggtaata actttgtaag tggaacttac  52920
tttggggaga ataataatca gaaagttaaa tattcttggc taagaataga tttcaaaaca  52980
aatgatattt taagctataa tgacttaaac ttttaagtat aatatttggt atgcttacag  53040
atgatctcgt tttgtgcttt gttatatgtc ttctcaatct tggaattaat ttaacatttg  53100
tacagtttct ttcctgtatt tatccttggt ttctgactta gtagtttctt caaagaaggg  53160
caccctgtct tttgatatgt aataccttcc acttatatat gctttttttt tttttttttt  53220
tgagatggag tctcactctg ttgcccaggc tggagtgcaa tggcacgatc tcagctcact  53280
gcaacctccg cctcccaagt tcaagcgatt ctcctgcctc agcctctcga gtagttggga  53340
ttataggcac ctgccaccac acccggctaa tttttttgta tttttagtag agatggggtt  53400
tcactatatt ggccaggctg gtgtcaaact cctgacctca tgatccaccc gcctcggcct  53460
cccaaagtgc tgggattaca ggcatgagcc actgcgcccg gcctatcttt gctttttact  53520
tttctccaag tacattcaaa cctattatta ttttaagtat ttaggttatt gttctggtaa  53580
ctaaaggata cttgataggt ttatggattt gcttgaactt aacgcttgca tgagcccttt  53640
gtaacttggt tttttctttc tttgcattaa taggatttta ctaacattct caggaagtag  53700
gtacaaagaa ttaaaatttt taatctatat aagctgtttt cactaaaagg aactagagtt  53760
```

```
tgtatacaaa tagctaattt cagatttgtg ataggaaatg tataatatat gagcctagag  53820
atcttgtcat accagagagt aaggaagctg ttaaagattt ctgaggttgt caaaaggtct  53880
tagtagccaa cctccccatc ttcaaaggtg gcataatttg agcatcaaaa agaataatgg  53940
ccataatgga ttaaaacata tcaaatatat taaaacttac gaactcataa aaatttcata  54000
ggtctccttt ggatcatgct agggaagcaa cacattgtcc tgaaaatggg taaagaagaa  54060
gaaaaaattt agcatccatc tgtctttcct aaaagaacca tatcttggtt tagcagggta  54120
atgaagaaaa gtgtttcatt agactctaag ctaataaaat ggagaagaaa tgatagaatt  54180
aatatatcac cagtatgcaa ctcttaataa aataacccct gtggatgtta atgatggctt  54240
aaaccatttg atcaaaagct gttggggaac tttataatta ataggctaac catacctgaa  54300
ctcactgata aatcttaaca tgagagacac agcaaagcat tttgtgcttg cagtactacc  54360
tatgaaatac tcttgctaaa aaattaaacc tgaattaaat caagccttta ggtctaacca  54420
gtttgtagaa aataaagcat agaaatgcag ttgaccaaat ccagaatttg agatgttcaa  54480
tggggtaaag acctcatgtc ttcagcaaca agtttttttt ttcaagggaa aaaatatgag  54540
aaacaataac ctgtatatca aaagagactt aagactagag gtccttaagt cttagtttgc  54600
ctgagacagt ccttgttgat attgttgtat tagaatgatt attaagaatg ggccctttca  54660
ctccaaaagg tgtcccaatt tggatgataa attatatagt caccgactta agacctatga  54720
accaaatcta gtggtgaatt ctggttcaaa caaagcaatt gtgacacaca tttgagacga  54780
ctggtgaagt ttgaacatgg actagacatt tgataggaag gaatcagtgt taaccttttt  54840
agatgtgata gtggtcttaa agtgctctta cctcttagag atacatgctg aagtaaatgg  54900
atgaaatgat acaggatttg tttcaaaata atcctgggtt tatggaggag ttgagtggcc  54960
agtcctgttg gtaaatgtct gtactccact tgttggtaaa tgttgaagct gggtaatgaa  55020
tacaagggag ttaattatac tgttctctct acttttgtat gtgtttttaa atcttttatt  55080
actgaaggcc aggtgtggtg gctcatgcct gtaatctttg gaggtcaagg tgggcagatt  55140
gcttgagccc aggagtttga gaccagcttg ggcaacatgg tgaaatgcca tctcttcaaa  55200
aaatacaaaa attagccagg catggtggta catgcctgta gtcccagcta cctgggaggc  55260
tgaggtggga ggatggcttg agcctgggag gtcaaggctg tagtgagcac tactcatgcc  55320
actgcactcc agcctgggca acagagtgag acttgtctcc aaaaaaaaaa aaaattatgg  55380
aaaaggtaag ggaaaatatg atgttgaata aaacactggc aactttaatt ttagtaataa  55440
atatttattt gcatcattta caggttgtaa gccaatgttg tgaggcttca agttcagaca  55500
tcactgagaa atcagatgga cgtaaggcag ctcatgagaa acagcataac atttttcttg  55560
atcagatgac tattgatgaa gataaattga tagcacaaaa tctagaactt aatgaaacca  55620
taaaaattgg tttgactaag cttaattgct ttctggaaca ggatctgaaa ctggatatcc  55680
caacaggtac tttaaaagag aaatagaatt gttaaatttt ttgaagtcga attcaactct  55740
atgtagtgtc agatgttcag aaaaattagg tcctgccatt gcctgacaga aatttaacat  55800
ctcactgtaa tcaactcaaa atgggaaaac tggaacctta aaatagtttt aatcaagtgt  55860
catgatacag gtggtatcac aattcagtat aatttcacat actttcaggg agttgacttt  55920
gttaataggg gattttttaa aacaaataca aacctagcac tgtttgtaaa aggacatttt  55980
aataccacaa atatgggaga gatgtaactg actaaatcta gtttaatgca aagtttacca  56040
cattgtgcat tttgttctgt gtccctctca ttttgtcata gactattgcc atttaggaat  56100
```

-continued

```
ccctgtttta agagatcagg gatcaccatg gaccattagc atttaggaat caacattttg  56160
agagatcaca tatggcaaag atcattatag gctgtaatga ttcagggagg tcttcatgga  56220
agagatgtaa caagctgttt tacacagcat gaataattgg gttcttcatt ggattatggt  56280
aatggttgca caccctgtaa actcactaaa atccactgaa ttgtacacat aaaatgagtg  56340
ttttatggta tgtaaattat atcacaaaac tctttttttt ttttaattta aaaagcaatt  56400
gttaaaaggg gatggtgcta catagaatgt tggtttattt attccccaag agacctgtag  56460
gatttactgt ctacttttca atgaagttag gaatgtaaat gttgagtgaa aaggcaagta  56520
cttttgtaaa tcatgagagc atgagcttat tacagagaaa tataactggg ggcctgatgc  56580
ggtggctcac acctataatc ccagcacttc gggaggcaag gcaggaggat cgtttgagcc  56640
caggggttca agaccagcct gggcaacata gtatatgtat ataactagtt aatatttaac  56700
caccacacca catttatagt gaaatgatta ctcctatcaa agtaatcatg ttgggaaatc  56760
tactcattcc aataatgctg ccattttttt cagaacacta taactccttt tagagcttat  56820
aacacatctt ttatatatcc tcagagatgg taaacttcat gttttagaga gtaggatgaa  56880
tcttgaaaac agtaaagtct gtcatcaaat tagaaagtat tgttagttgc aaacaatgtc  56940
tgacaggtag caagactgat cctcatatat ggcaattata tttttatatt tttagaagac  57000
aagattaatt aggaagtttt aggttttttt aaaaatattt acatctcata ctttaatttt  57060
tacctcttat ctaatgtccg ttaaaggtac gacaccacag aggaaaagtt atttataccc  57120
atcaacactg gtaagaactg aaccacgtga acatctcctt gatcagctga aaaggaaaca  57180
gcctgagctg ttaatgatgc taaactgttc agaaaacaac aaagaagaga caattccggt  57240
aaatttaaag gatcatattt tataatagaa ctcttttatg aactcttgat gtggctgact  57300
tcatgtgaag aattttactg tttacccctc aatcttaccc cgcctctcat taatgatagg  57360
cctagccctt aggcttgttt cttttaatct tactagtttt taaattatgc tagtagataa  57420
taatagccaa tacttaatat tgtgcttagt aacattgtta tataggaacc tctactctct  57480
ataaaaatat attaggaatt attttcatta atttgtagac tttctaataa ttttgttgag  57540
gtttaacttt tatattatac catgggcatt gtgttatact caaagctgct gttactcttg  57600
tgatgacttt taagcccttg gacttagtca ctcatccagt ttcttctttt aggatgtgga  57660
tgtagaagag gcagttctgg ggcagtatac tgaagaacct ctaagtcaag agccatctgt  57720
agatgctggt gtggattgtt catcaattgg cggggttcca tttttccagg tatgtcatat  57780
cagataaccc ttccacatct gatgtaagtc attcatttac tattcattat aaaggtattg  57840
ttcgtggtga gcagaacaac aaaaaccttt caattattcc ttaggatggc ttgttaacgc  57900
ttatgatttg aattatttac aaaaatctga tattgataag gggttttctg tagaataaat  57960
gaaggcagaa tttgacttaa tctacatcct tagctgataa tctttagcta ttgtatttat  58020
tccttttctg cttgctatat actcagacac tgagagcagt catttctctt ccttctacct  58080
ttgacatgta agtcttggaa cctatctctg cccataatca gactttgaag gcaaagtgat  58140
tgaaaagatt gagagactgg aggcctctta ggttatatta gtgatttctc ctgcctgagg  58200
ctcttctctt gtaaactgtt gccccatgtt tcctgagcac cttgcctgct ctaatccagt  58260
gtaattaaat cctgtgacct ctcctaccca ctcttctttt ttttttgaga ctgagtcacc  58320
caggctgaag tggagtggca cgatcttggc tcacttaacc tccgcctcct gagttcaagt  58380
gattctcctg actcagcctc ccgggtagct aggattacag gcatgcacca ccacacctgg  58440
ctaatttttt tgtattttta gtagagacag ggtttcacta tgtgggccag gctggtctca  58500
```

```
aactcctgac ctcaagttat ctaccctcct cggcctccca aagtgctggg attacaggcg  58560
tgagccactg tgcccagccc tctacccact tttttttttc ttttgagacg gagcttcgct  58620
cttgtttccc aggctggagt gcaatggcac gatcttggct caccgcaact tccacctcct  58680
gggttcaagt gattctcctg cctcagcctc ccgagtagcc aggattacag gcatgtgcca  58740
ccatgcctgg ctaattttgt tttttttttt tttttttttt tttttttttt tttttttttt  58800
agtagagggg gtttctctgt gttggtcagg ctggtctcga actcccaact tcaggtgatc  58860
tgcctgcctc ggcctcccgt agtgctggga ttacaggtgt gagccaccgg cccggcccct  58920
cctacccact ttttaacact gttgagaaca tagttggttt atgattcatc tcagcattga  58980
tgactgagta cacaatcaat gtcaccagtc ccttaatgtt ctctatgggt aagtaggagg  59040
attccaatga aatacaactt ccaagtgagg ctctataaag tgctggtatc ttttcctcta  59100
atttgagggt acaagcctag acagagtgtg tgaaggaaaa atttccttac gtaggacatt  59160
ggtatctaca tttacagttg aagttctact tctgagatgc atatgcttgt accttttttt  59220
tttttttttt tttttaaata tatatagaga gagggtcttg ctatgttggc cagactggtc  59280
ttgaactctt ggcctcaagc agccctccta cctcagcctc ccaaaatgct aggattacag  59340
gcatgaacca ctgcgcctgg ctgcttgtac cttttttgtg tgtatgtctt gttttgtttt  59400
tttgtttttg agacggagtt ttgctcttgt tgcccaggcc agagtgcaat tgcctgatct  59460
tggctcacca caatctccgc ctcccgggtt ctagcgattc tcttgcctca tcctcccgag  59520
tagctgggat tacaggcatg caccaccaca cctggctaat attgtatttt tagtagagaa  59580
ggggtttctc catgttggtc aggctaatct tgaactcccg acctcaggtg atccgcccgc  59640
ctcggcctcc caaagtgctg ggattacaag cgtgagccac cgcgctcggc ctgtaactgt  59700
tttttaatag atctacagct ccttccctta aggtctaaag attctccatc cctgctttca  59760
acagttaaca aagttccaac tcagattctc ataaattcct ccctgtcttc ctctgggcaa  59820
ttttattccc aaattcttgc caccttttgc tttattcctt actattagag aactataaat  59880
atgtttcttt cagttttcat ccttttcttc tatcttataa agttaggaaa gggggaagga  59940
taagagaacc tggtgactac ttaatccctg gtcagaaatc gttttattat tattatctgt  60000
ggcattttga attaggctta gtgattcagc tatggcaagg aagtccctac agtaccagaa  60060
agggtttggg atggggtttt agaccttcag ctgaagtcca gaaatgatct tttccctagt  60120
agcagtgtga tgtggggatt ttctctgcgt ttaaaacttt aaaagttggt ttacaatttg  60180
tctcagcatt gatgactgag tgtacaatga atgtcaccag tccattaatg ttctgtatgg  60240
gtaagtagga ttccaatgaa atagaacttc caaatgagga atatgaaata ggttttacaa  60300
ataaaataaa atacaatttt aaaaaacaag taaaagtgtt tttaaggtgg cccatatacc  60360
agtttctctg cttaaaacag aattggcttt tctgcatgac agcaaatctt tgtttcctta  60420
gagcagggtt tcttgacagc agtgctattg gcattttaaa ctggataatt ctttgttgtg  60480
atgggctttc ctgtggactg tactatgttg gtacacaaga aaaacagtgt actatgtgaa  60540
tactcactca aagccagtag cactccctga ttgtaacacc aaaaaagtct ctcagcattg  60600
ccaaatgtcc cctgtggcag cagaatcact ccctgatgag aaccactacc ctggagtaaa  60660
atctataact atgtcttaga aaataacaca gaaaattaat atttctttca ctctactcct  60720
tccattagtg atcaaataaa gaaggcattt ggcgctactt gccaaattgt tggctcaaac  60780
ttgtgctgaa cctttttttgg ttttctacac ttaagttttt ttgcctataa cccagagaac  60840
```

-continued

```
tttgaaaata gagtgtagtt aatgtgtatc taatgttact ttgtattgac ttaattttcc  60900
cgccttaaat ccacagcata aaaaatcaca tggaaaagac aaagaaaaca gaggcattaa  60960
cacactggag aggtctaaag tggaagaaac tacagagcac ttggttacaa agagcagatt  61020
acctctgcga gcccagatca acctttaatt cacttggggg ttggcaattt tatttttaaa  61080
gaaaacttaa aaataaaacc tgaaacccca gaacttgagc cttgtgtata gattttaaaa  61140
gaatatatat atcagccggg cgcggtggct catgcctgta atcccagcac tttgggaggc  61200
tgaggcgggt ggattgcttg agcccaggag tttgagacca gcctggccaa cgtggcaaaa  61260
cctcgtctct gttaaaaatt agccgggcgt ggtggcacac tcctgtaatc ccagctactg  61320
gggaggctga ggcacgagaa tcacttgaac ccaggaagcg gggttgcagt gagccaaagg  61380
tacaccacta cactccagcc tgggcaacag agcaagactc ggtctcaaaa acaaaattta  61440
aaaaagatat aaggcagtac tgtaaattca gttgaatttt gatatctacc catttttctg  61500
tcatccctat agttcacttt gtattaaatt gggtttcatt tgggatttgc aatgtaaata  61560
cgtatttcta gttttcatat aaagtagttc ttttataaca aatgaaaagt atttttcttg  61620
tatattatta agtaatgaat atataagaac tgtactcttc tcagcttgag cttacatagg  61680
taaatatcac caacatctgt ccttagaaag gaccatctca tgtttttttt cttgctatga  61740
cttgtgtatt ttcttgcatc ctccctagac ttccctattt cgctttctcc tcggctcact  61800
ttctcccttt ttatttttca ccaaaccatt tgtagagcta caaaaggtat cctttcttat  61860
tttcagtagt cagaatttta tctagaaatc ttttaacacc tttttagtgg ttatttctaa  61920
aatcactgtc aacaataaat ctaaccctag ttgtatccct cctttcagta tttttcactt  61980
gttgccccaa atgtgaaagc atttcattcc tttaagaggc ctaactcatt caccctgaca  62040
gagttcacaa aaagcccact taagagtata cattgctatt atgggagacc acccagacat  62100
ctgactaatg gctctgtgcc cacactccaa gacctgtgcc ttttagagaa gctcacaatg  62160
atttaaggac tgtttgaaac ttccaattat gtctataatt tatattcttt tgtttacatg  62220
atgaaacttt ttgttgttgc ttgtttgtat ataatacaat gtgtacatgt atctttttct  62280
cgattcaaat cttaaccctt aggactctgg tatttttgat ctggcaacca tatttctgga  62340
agttgagatg tttcagcttg aagaaccaaa acagaaggaa tatgtacaaa gaataaattt  62400
tctgctcacg atgagtttag tgtgtaaagt ttagagacat ctgactttga tagctaaatt  62460
aaaccaaacc ctattgaaga attgaatata tgctacttca agaaactaaa ttgatctcgt  62520
agaattatct taataaaata atggctataa tttctctgca aaatcagatg tcagcataag  62580
cgatggataa tacctaataa actgccctca gtaaatccat ggttaataaa tgtggtttct  62640
acattaacct gcttgctcca taatttctta tctggcaatg ggtatattta gagggttagg  62700
caagctgcat tcacattccc aaaataaact atgcaggtac caccaaagaa gaaggagcct  62760
agtaaacttg caggctttta gttgcactcc aaggggctat cctaggtgca aggttagtga  62820
gaagtaggcc ctcacacagc ctgaagtcca gctttaagtc atctcattcc atgactgttt  62880
aagttatctg agaatgctga tgcaactaat ttcactgcct cacagaagca aaaataaatc  62940
tccagataat tttaacatcc agaaccataa attagctcta ccaattttca tacacaatgt  63000
cgggccctca gaatgtaacc aagagtagca tcagcaaaaa tggcc                  63045
```

<210> SEQ ID NO 77
<211> LENGTH: 4908
<212> TYPE: DNA
<213> ORGANISM: Homo sapiens

<400> SEQUENCE: 77

```
acctgcgtgc agtcggtcct ccaggccacg cagcgcccga gagtaccagg gagactccgg     60
cccctgtcgg cgccaagccc ctccgcccct cacagcgccc aggtccgcgg ccgggccttg    120
attttttggc ggggaccgtc atggcgtcgc agccaaattc gtctgcgaag aagaaagagg    180
agaaggggaa gaacatccag gtggtggtga gatgcagacc atttaatttg gcagagcgga    240
aagctagcgc ccattcaata gtagaatgtg atcctgtacg aaaagaagtt agtgtacgaa    300
ctggaggatt ggctgacaag agctcaagga aaacatacac ttttgatatg gtgtttggag    360
catctactaa acagattgat gtttaccgaa gtgttgtttg tccaattctg gatgaagtta    420
ttatgggcta taattgcact atctttgcgt atggccaaac tggcactgga aaaactttta    480
caatggaagg tgaaaggtca cctaatgaag agtatacctg ggaagaggat cccttggctg    540
gtataattcc acgtaccctt catcaaattt ttgagaaact tactgataat ggtactgaat    600
tttcagtcaa agtgtctctg ttggagatct ataatgaaga gctttttgat cttcttaatc    660
catcatctga tgtttctgag agactacaga tgtttgatga tccccgtaac aagagaggag    720
tgataattaa aggtttagaa gaaattacag tacacaacaa ggatgaagtc tatcaaattt    780
tagaaaaggg ggcagcaaaa aggacaactg cagctactct gatgaatgca tactctagtc    840
gttcccactc agttttctct gttacaatac atatgaaaga aactacgatt gatggagaag    900
agcttgttaa aatcggaaag ttgaacttgg ttgatcttgc aggaagtgaa aacattggcc    960
gttctggagc tgttgataag agagctcggg aagctggaaa tataaatcaa tccctgttga   1020
ctttgggaag ggtcattact gcccttgtag aaagaacacc tcatgttcct tatcgagaat   1080
ctaaactaac tagaatcctc caggattctc ttggagggcg tacaagaaca tctataattg   1140
caacaatttc tcctgcatct ctcaatcttg aggaaactct gagtacattg gaatatgctc   1200
atagagcaaa gaacatattg aataagcctg aagtgaatca gaaactcacc aaaaaagctc   1260
ttattaagga gtatacggag gagatagaac gtttaaaacg agatcttgct gcagcccgtg   1320
agaaaaatgg agtgtatatt tctgaagaaa attttagagt catgagtgga aaattaactg   1380
ttcaagaaga gcagattgta gaattgattg aaaaaattgg tgctgttgag gaggagctga   1440
atagggttac agagttgttt atggataata aaaatgaact tgaccagtgt aaatctgacc   1500
tgcaaaataa aacacaagaa cttgaaacca ctcaaaaaca tttgcaagaa actaaattac   1560
aacttgttaa agaagaatat atcacatcag ctttggaaag tactgaggag aaacttcatg   1620
atgctgccag caagctgctt aacacagttg aagaaactac aaaagatgta tctggtctcc   1680
attccaaact ggatcgtaag aaggcagttg accaacacaa tgcagaagct caggatattt   1740
ttggcaaaaa cctgaatagt ctgtttaata atatggaaga attaattaag gatggcagct   1800
caaagcaaaa ggccatgcta gaagtacata agaccttatt tggtaatctg ctgtcttcca   1860
gtgtctctgc attagatacc attactacag tagcacttgg atctctcaca tctattccag   1920
aaaatgtgtc tactcatgtt tctcagattt ttaatatgat actaaaagaa caatcattag   1980
cagcagaaag taaaactgta ctacaggaat tgattaatgt actcaagact gatcttctaa   2040
gttcactgga aatgatttta tccccaactg tggtgtctat actgaaaatc aatagtcaac   2100
taaagcatat tttcaagact tcattgacag tggccgataa gatagaagat caaaaaaagg   2160
aactagatgg ctttctcagt atactgtgta acaatctaca tgaactacaa gaaaatacca   2220
tttgttcctt ggttgagtca caaaagcaat gtggaaacct aactgaagac ctgaagacaa   2280
```

-continued

```
taaagcagac ccattcccag gaactttgca agttaatgaa tctttggaca gagagattct   2340
gtgctttgga ggaaaagtgt gaaaatatac agaaaccact tagtagtgtc caggaaaata   2400
tacagcagaa atctaaggat atagtcaaca aaatgacttt tcacagtcaa aaattttgtg   2460
ctgattctga tggcttctca caggaactca gaaattttaa ccaagaaggt acaaaattgg   2520
ttgaagaatc tgtgaaacac tctgataaac tcaatggcaa cctggaaaaa atatctcaag   2580
agactgaaca gagatgtgaa tctctgaaca caagaacagt ttatttttct gaacagtggg   2640
tatcttcctt aaatgaaagg gaacaggaac ttcacaactt attggaggtt gtaagccaat   2700
gttgtgaggc ttcaagttca gacatcactg agaaatcaga tggacgtaag gcagctcatg   2760
agaaacagca taacattttt cttgatcaga tgactattga tgaagataaa ttgatagcac   2820
aaaatctaga acttaatgaa accataaaaa ttggtttgac taagcttaat tgctttctgg   2880
aacaggatct gaaactggat atcccaacag gtacgacacc acagaggaaa agttatttat   2940
acccatcaac actggtaaga actgaaccac gtgaacatct ccttgatcag ctgaaaagga   3000
aacagcctga gctgttaatg atgctaaact gttcagaaaa caacaaagaa gagacaattc   3060
cggatgtgga tgtagaagag gcagttctgg ggcagtatac tgaagaacct ctaagtcaag   3120
agccatctgt agatgctggt gtggattgtt catcaattgg cggggttcca tttttccagc   3180
ataaaaaatc acatggaaaa gacaaagaaa acagaggcat taacacactg gagaggtcta   3240
aagtggaaga aactacagag cacttggtta caaagagcag attacctctg cgagcccaga   3300
tcaaccttta attcacttgg gggttggcaa ttttattttt aaagaaaact taaaaataaa   3360
acctgaaacc ccagaacttg agccttgtgt atagatttta aaagaatata tatatcagcc   3420
gggcgcggtg gctcatgcct gtaatcccag cactttggga ggctgaggcg ggtggattgc   3480
ttgagcccag gagtttgaga ccagcctggc caacgtggca aaacctcgtc tctgttaaaa   3540
attagccggg cgtggtggca cactcctgta atcccagcta ctggggaggc tgaggcacga   3600
gaatcacttg aacccaggaa gcggggttgc agtgagccaa aggtacacca ctacactcca   3660
gcctgggcaa cagagcaaga ctcggtctca aaaacaaaat ttaaaaaaga tataaggcag   3720
tactgtaaat tcagttgaat tttgatatct acccattttt ctgtcatccc tatagttcac   3780
tttgtattaa attgggtttc atttgggatt tgcaatgtaa atacgtattt ctagttttca   3840
tataaagtag ttcttttata acaaatgaaa agtatttttc ttgtatatta ttaagtaatg   3900
aatatataag aactgtactc ttctcagctt gagcttaaca taggtaaata tcaccaacat   3960
ctgtccttag aaaggaccat ctcatgtttt ttttcttgct atgacttgtg tattttcttg   4020
catcctccct agacttccct atttcgcttt ctcctcggct cactttctcc ctttttattt   4080
ttcaccaaac catttgtaga gctacaaaac ctatcctttc ttattttcag tagtcagaat   4140
tttatctaga aatcttttaa caccttttta gtggttattt ctaaaatcac tgtcaacaat   4200
aaatctaacc ctagttgtat ccctccttta agtatttaaa acttgttgcc ccaaatgtga   4260
aagcatttaa ttcctttaag aggcctaact cattcaccct gacagagttc acaaaaagcc   4320
cactttagag tatacattgc tattatggga gaccacccag acatctgact aatggctctg   4380
tgccacactc caagacctgt gccttttaga gaagctcaca atgatttaag gactgtttga   4440
aacttccaat tatgtctata atttatattc ttttgtttac atgatgaaac tttttgttgt   4500
tgcttgtttg tatataatac aatgtgtaca tgtatctttt tctcgattca aatcttaacc   4560
cttaggactc tggtattttt gatctggcaa ccatatttct ggaagttgag atgtttcagc   4620
ttgaagaacc aaaacagaag gaatatgtac aaagaataaa ttttctgctc acgatgagtt   4680
```

-continued tagtgtgtaa agtttagaga catctgactt tgatagctaa attaaaccaa accctattga 4740
agaattgaat atatgctact tcaagaaact aaattgatct cgtagaatta tcttaataaa 4800
ataatggcta taatttctct gcaaaatcag atgtcagcat aagcgatgga taatacctaa 4860
taaactgccc tcagtaaatc catggttaat aaatgtggtt tctacatt 4908

<210> SEQ ID NO 78
<211> LENGTH: 2310
<212> TYPE: DNA
<213> ORGANISM: Homo sapiens

<400> SEQUENCE: 78
gcggagacga gattagtgat ttggcggctc cgactggcgc gggacaaacg ccacggccag 60
agtaccgggt agagagcggg gacgccgacc tgcgtgcgtc ggtcctccag gccacgccag 120
cgcccgagag ggaccaggga gactccggcc cctgtcggcc gccaagcccc tccgcccctc 180
acagcgccca ggtccgcggc cgggccttga ttttttggcg gggaccgtca tggcgtcgca 240
gccaaattcg tctgcgaaga agaaagagga gaaggggaag aacatccagg tggtggtacg 300
acaccacaga ggaaaagtta tttataccca tcaacactgg taagaactga accacgtgaa 360
catctccttg atcagctgaa aaggaaacag cctgagctgt taatgatgct aaactgttca 420
gaaaacaaca aagaagagac aattccggat gtggatgtag aagaggcagt tctggggcag 480
tatactgaag aacctctaag tcaagagcca tctgtagatg ctggtgtgga ttgttcatca 540
attggcgggg ttccattttt ccagcataaa aaatcacatg gaaaagacaa agaaaacaga 600
ggcattaaca cactggagag gtctaaagtg gaagaaacta cagagcactt ggttacaaag 660
agcagattac ctctgcgagc ccagatcaac ctttaattca cttgggggtt ggcaatttta 720
tttttaaaga aaacttaaaa ataaaacctg aaaccccaga acttgagcct tgtgtataga 780
ttttaaaaga atatatatat cagccgggcg cggtggctca tgcctgtaat cccagcactt 840
tgggaggctg aggcgggtgg attgcttgag cccaggagtt tgagaccagc ctggccaacg 900
tggcaaaacc tcgtctctgt taaaaattag ccgggcgtgg tggcacactc ctgtaatccc 960
agctactggg gaggctgagg cacgagaatc acttgaaccc aggaagcggg gttgcagtga 1020
gccaaaggta caccactaca ctccagcctg ggcaacagag caagactcgg tctcaaaaac 1080
aaaatttaaa aaagatataa ggcagtactg taaattcagt tgaattttga tatctaccca 1140
tttttctgtc atccctatag ttcactttgt attaaattgg gtttcatttg ggatttgcaa 1200
tgtaaatacg tatttctagt tttcatataa agtagttctt ttataacaaa tgaaaagtat 1260
ttttcttgta tattattaag taatgaatat ataagaactg tactcttctc agcttgagct 1320
tacataggta aatatcacca acatctgtcc ttagaaagga ccatctcatg ttttttttct 1380
tgctatgact tgtgtatttt cttgcctcct ccctagactt ccctatttcg ctttctcctc 1440
ggctcacttt ctcccttttt atttttcacc aaaccatttg tagagctaca aaaggtatcc 1500
tttcttattt tcagtagtca gaattttatc tagaaatctt ttaacacctt tttagtggtt 1560
atttctaaaa tcactgtcaa caataaatct aaccctagtt gtatccctcc tttcagtatt 1620
tttcacttgt tgccccaaat gtgaaagcat ttcattcctt taagaggcct aactcattca 1680
ccctgacaga gttcacaaaa agcccacttt agagtataca ttgctattat gggagaccac 1740
ccagacatct gactaatggc tctgtgccca cactccaaga cctgtgcctt ttagagaagc 1800
tcacaatgat ttaaggactg tttgaaactt ccaattatgt ctataattta tattcttttg 1860

-continued

```
tttacatgat gaaacttttt gttgttgctt gtttgtatat aatacaatgt gtacatgtat   1920

ctttttctcg attcaaatct taacccttag gactctggta tttttgatct ggcaaccata   1980

tttctggaag ttgagatgtt tcagcttgaa gaaccaaaac agaaggaata tgtacaaaga   2040

ataaattttc tgctcacgat gagtttagtg tgtaaagttt agagacatct gactttgata   2100

gctaaattaa accaaaccct attgaagaat tgaatatatg ctacttcaag aaactaaatt   2160

gatctcgtag aattatctta ataaaataat ggctataatt tctctgcaaa atcagatgtc   2220

cgcataagcg atggataata cctaataaac tgccctcagt aaatccatgg ttaataaatg   2280

tggtttctac attaaaaaaa aaaaaaaaaa                                     2310
```

<210> SEQ ID NO 79
<211> LENGTH: 673
<212> TYPE: DNA
<213> ORGANISM: Homo sapiens

<400> SEQUENCE: 79

```
ttagtgtacg aactggagga ttggctgaca agagctcaag gaaaacatac acttttgata     60

tggtgtttgg agcatctact aaacagattg atgtttaccg aagtgttgtt tgtccaattc    120

tggatgaagt tattatgggc tataattgca ctatctttgc gtatggccaa actggcactg    180

gaaaaacttt tacaatggaa ggtgaaaggt cacctaatga agagtatacc tgggaagagg    240

atcccttggc tggtataatt ccacgtaccc ttcatcaaat ttttgagaaa cttactgata    300

atggtactga attttcagtc aaagtgtctc tgttggagat ctataatgaa gagctttcgt    360

gatcttctta atccatcatc tgatgtttct gagagactac agatgtttga tgatccccgt    420

aacaagagag gagtgataat taaaggttta gaagaaatta cagtacacaa caaggatgaa    480

gtctatcaaa ttttagaaaa gggggcagca aaaaggacaa ctgcagctac tctgatgaat    540

gcatactcta gttgtatccc tcctttcagt atttttcact tgttgcccca aatgtgaaag    600

catttcattc ctttaagagg cctaactcat tcaccctgac agagttcaca aaaagcccac    660

tttagagtat aca                                                       673
```

<210> SEQ ID NO 80
<211> LENGTH: 20
<212> TYPE: DNA
<213> ORGANISM: Homo sapiens

<400> SEQUENCE: 80

```
gctccaaaca ccatatcaaa                                                 20
```

<210> SEQ ID NO 81
<211> LENGTH: 20
<212> TYPE: DNA
<213> ORGANISM: Homo sapiens

<400> SEQUENCE: 81

```
tagatgctcc aaacaccata                                                 20
```

<210> SEQ ID NO 82
<211> LENGTH: 20
<212> TYPE: DNA
<213> ORGANISM: Homo sapiens

<400> SEQUENCE: 82

```
tttagattct cgataaggaa                                                 20
```

<210> SEQ ID NO 83
<211> LENGTH: 20
<212> TYPE: DNA
<213> ORGANISM: Homo sapiens

<400> SEQUENCE: 83
gttagtttag attctcgata 20

<210> SEQ ID NO 84
<211> LENGTH: 20
<212> TYPE: DNA
<213> ORGANISM: Homo sapiens

<400> SEQUENCE: 84
ggattctagt tagtttagat 20

<210> SEQ ID NO 85
<211> LENGTH: 20
<212> TYPE: DNA
<213> ORGANISM: Homo sapiens

<400> SEQUENCE: 85
attatagatg ttcttgtacg 20

<210> SEQ ID NO 86
<211> LENGTH: 20
<212> TYPE: DNA
<213> ORGANISM: Homo sapiens

<400> SEQUENCE: 86
gttgcaatta tagatgttct 20

<210> SEQ ID NO 87
<211> LENGTH: 20
<212> TYPE: DNA
<213> ORGANISM: Homo sapiens

<400> SEQUENCE: 87
cagagtttcc tcaagattga 20

<210> SEQ ID NO 88
<211> LENGTH: 20
<212> TYPE: DNA
<213> ORGANISM: Homo sapiens

<400> SEQUENCE: 88
gtactcagag tttcctcaag 20

<210> SEQ ID NO 89
<211> LENGTH: 20
<212> TYPE: DNA
<213> ORGANISM: Homo sapiens

<400> SEQUENCE: 89
ccaatgtact cagagtttcc 20

<210> SEQ ID NO 90
<211> LENGTH: 20
<212> TYPE: DNA
<213> ORGANISM: Homo sapiens

<400> SEQUENCE: 90
atattccaat gtactcagag 20

<210> SEQ ID NO 91
<211> LENGTH: 20
<212> TYPE: DNA
<213> ORGANISM: Homo sapiens

<400> SEQUENCE: 91
tgagcatatt ccaatgtact 20

<210> SEQ ID NO 92
<211> LENGTH: 20
<212> TYPE: DNA
<213> ORGANISM: Homo sapiens

<400> SEQUENCE: 92
ctccttaata agagcttttt 20

<210> SEQ ID NO 93
<211> LENGTH: 20
<212> TYPE: DNA
<213> ORGANISM: Homo sapiens

<400> SEQUENCE: 93
gtatactcct taataagagc 20

<210> SEQ ID NO 94
<211> LENGTH: 20
<212> TYPE: DNA
<213> ORGANISM: Homo sapiens

<400> SEQUENCE: 94
tacactccat ttttctcacg 20

<210> SEQ ID NO 95
<211> LENGTH: 20
<212> TYPE: DNA
<213> ORGANISM: Homo sapiens

<400> SEQUENCE: 95
gatttacact ggtcaagttc 20

<210> SEQ ID NO 96
<211> LENGTH: 20
<212> TYPE: DNA
<213> ORGANISM: Homo sapiens

<400> SEQUENCE: 96
ggtcagattt acactggtca 20

<210> SEQ ID NO 97
<211> LENGTH: 20
<212> TYPE: DNA
<213> ORGANISM: Homo sapiens

<400> SEQUENCE: 97
ttgcaggtca gatttacact 20

<210> SEQ ID NO 98
<211> LENGTH: 20
<212> TYPE: DNA
<213> ORGANISM: Homo sapiens

<400> SEQUENCE: 98
tgcatctcac caccacctgg 20

<210> SEQ ID NO 99
<211> LENGTH: 20
<212> TYPE: DNA
<213> ORGANISM: Homo sapiens

<400> SEQUENCE: 99
gaagtaaaag caggtagatg 20

<210> SEQ ID NO 100
<211> LENGTH: 20
<212> TYPE: DNA
<213> ORGANISM: Homo sapiens

<400> SEQUENCE: 100
acctgagttc atttttccca 20

<210> SEQ ID NO 101
<211> LENGTH: 20
<212> TYPE: DNA
<213> ORGANISM: Homo sapiens

<400> SEQUENCE: 101
ccgtatactc ctacacaaga 20

<210> SEQ ID NO 102
<211> LENGTH: 20
<212> TYPE: DNA
<213> ORGANISM: Homo sapiens

<400> SEQUENCE: 102
aaaatgcatc caacattctt 20

<210> SEQ ID NO 103
<211> LENGTH: 20
<212> TYPE: DNA
<213> ORGANISM: Homo sapiens

<400> SEQUENCE: 103
gaaatccatc agtctagata 20

<210> SEQ ID NO 104
<211> LENGTH: 20
<212> TYPE: DNA
<213> ORGANISM: Homo sapiens

<400> SEQUENCE: 104
catccacatc ctaaaagaag 20

<210> SEQ ID NO 105
<211> LENGTH: 20
<212> TYPE: DNA
<213> ORGANISM: Homo sapiens

<400> SEQUENCE: 105
ggatacaact agggttagat 20

<210> SEQ ID NO 106
<211> LENGTH: 20
<212> TYPE: DNA
<213> ORGANISM: Homo sapiens

<400> SEQUENCE: 106
tgcgtggcct ggaggaccga 20

<210> SEQ ID NO 107
<211> LENGTH: 20
<212> TYPE: DNA
<213> ORGANISM: Homo sapiens

<400> SEQUENCE: 107
ggagtctccc tggtactctc 20

<210> SEQ ID NO 108
<211> LENGTH: 20
<212> TYPE: DNA
<213> ORGANISM: Homo sapiens

<400> SEQUENCE: 108
gccatgacgg tccccgccaa 20

<210> SEQ ID NO 109
<211> LENGTH: 20
<212> TYPE: DNA
<213> ORGANISM: Homo sapiens

<400> SEQUENCE: 109
aattaaatgg tctgcatctc 20

<210> SEQ ID NO 110
<211> LENGTH: 20
<212> TYPE: DNA
<213> ORGANISM: Homo sapiens

<400> SEQUENCE: 110
cttttcgtac aggatcacat 20

<210> SEQ ID NO 111
<211> LENGTH: 20
<212> TYPE: DNA
<213> ORGANISM: Homo sapiens

<400> SEQUENCE: 111
acacttcggt aaacatcaat 20

<210> SEQ ID NO 112
<211> LENGTH: 20
<212> TYPE: DNA
<213> ORGANISM: Homo sapiens

<400> SEQUENCE: 112
caaacaacac ttcggtaaac 20

<210> SEQ ID NO 113
<211> LENGTH: 20
<212> TYPE: DNA
<213> ORGANISM: Homo sapiens

<400> SEQUENCE: 113
ttggacaaac aacacttcgg 20

<210> SEQ ID NO 114
<211> LENGTH: 20
<212> TYPE: DNA
<213> ORGANISM: Homo sapiens

<400> SEQUENCE: 114
tagcccataa taacttcatc 20

<210> SEQ ID NO 115
<211> LENGTH: 20
<212> TYPE: DNA
<213> ORGANISM: Homo sapiens

<400> SEQUENCE: 115
aattatagcc cataataact 20

<210> SEQ ID NO 116
<211> LENGTH: 20
<212> TYPE: DNA
<213> ORGANISM: Homo sapiens

<400> SEQUENCE: 116
aaagtttttc cagtgccagt 20

<210> SEQ ID NO 117
<211> LENGTH: 20
<212> TYPE: DNA
<213> ORGANISM: Homo sapiens

<400> SEQUENCE: 117
ttgtaaaagt ttttccagtg 20

<210> SEQ ID NO 118
<211> LENGTH: 20
<212> TYPE: DNA
<213> ORGANISM: Homo sapiens

<400> SEQUENCE: 118
tttcaccttc cattgtaaaa 20

<210> SEQ ID NO 119
<211> LENGTH: 20
<212> TYPE: DNA
<213> ORGANISM: Homo sapiens

<400> SEQUENCE: 119
tgacctttca ccttccattg 20

<210> SEQ ID NO 120
<211> LENGTH: 20
<212> TYPE: DNA
<213> ORGANISM: Homo sapiens

<400> SEQUENCE: 120
ttaggtgacc tttcaccttc 20

<210> SEQ ID NO 121
<211> LENGTH: 20
<212> TYPE: DNA
<213> ORGANISM: Homo sapiens

<400> SEQUENCE: 121
cttcattagg tgacctttca 20

<210> SEQ ID NO 122
<211> LENGTH: 20
<212> TYPE: DNA
<213> ORGANISM: Homo sapiens

<400> SEQUENCE: 122
acgtggaatt ataccagcca 20

<210> SEQ ID NO 123
<211> LENGTH: 20
<212> TYPE: DNA
<213> ORGANISM: Homo sapiens

<400> SEQUENCE: 123
ttctcaaaaa tttgatgaag 20

<210> SEQ ID NO 124
<211> LENGTH: 20
<212> TYPE: DNA
<213> ORGANISM: Homo sapiens

<400> SEQUENCE: 124
tcagtaagtt tctcaaaaat 20

<210> SEQ ID NO 125
<211> LENGTH: 20
<212> TYPE: DNA
<213> ORGANISM: Homo sapiens

<400> SEQUENCE: 125
cattatcagt aagtttctca 20

<210> SEQ ID NO 126
<211> LENGTH: 20
<212> TYPE: DNA
<213> ORGANISM: Homo sapiens

<400> SEQUENCE: 126
gcagttgtcc tttttgctgc 20

<210> SEQ ID NO 127
<211> LENGTH: 20
<212> TYPE: DNA
<213> ORGANISM: Homo sapiens

<400> SEQUENCE: 127
acaagctctt ctccatcaat 20

<210> SEQ ID NO 128
<211> LENGTH: 20
<212> TYPE: DNA
<213> ORGANISM: Homo sapiens

<400> SEQUENCE: 128
ttttaacaag ctcttctcca 20

<210> SEQ ID NO 129
<211> LENGTH: 20
<212> TYPE: DNA
<213> ORGANISM: Homo sapiens

<400> SEQUENCE: 129
tgttttcact tcctgcaaga 20

<210> SEQ ID NO 130
<211> LENGTH: 20
<212> TYPE: DNA
<213> ORGANISM: Homo sapiens

<400> SEQUENCE: 130
actcatgact ctaaaatttt 20

<210> SEQ ID NO 131
<211> LENGTH: 20
<212> TYPE: DNA
<213> ORGANISM: Homo sapiens

<400> SEQUENCE: 131
actctgtaac cctattcagc 20

<210> SEQ ID NO 132
<211> LENGTH: 20
<212> TYPE: DNA
<213> ORGANISM: Homo sapiens

<400> SEQUENCE: 132
tccatattat taaacagact 20

<210> SEQ ID NO 133
<211> LENGTH: 20
<212> TYPE: DNA
<213> ORGANISM: Homo sapiens

<400> SEQUENCE: 133
gacacatttt ctggaataga 20

<210> SEQ ID NO 134
<211> LENGTH: 20
<212> TYPE: DNA
<213> ORGANISM: Homo sapiens

<400> SEQUENCE: 134
tgagtacatt aatcaattcc 20

<210> SEQ ID NO 135
<211> LENGTH: 20
<212> TYPE: DNA
<213> ORGANISM: Homo sapiens

<400> SEQUENCE: 135
cttcaggtct tcagttaggt 20

<210> SEQ ID NO 136
<211> LENGTH: 20
<212> TYPE: DNA
<213> ORGANISM: Homo sapiens

<400> SEQUENCE: 136
attgtcttca ggtcttcagt 20

<210> SEQ ID NO 137
<211> LENGTH: 20
<212> TYPE: DNA
<213> ORGANISM: Homo sapiens

<400> SEQUENCE: 137
caagtgaatt aaaggttgat 20

<210> SEQ ID NO 138
<211> LENGTH: 20
<212> TYPE: DNA

<213> ORGANISM: Homo sapiens

<400> SEQUENCE: 138
aattcaactg aatttacagt 20

<210> SEQ ID NO 139
<211> LENGTH: 20
<212> TYPE: DNA
<213> ORGANISM: Homo sapiens

<400> SEQUENCE: 139
caaagtgaac tatagggatg 20

<210> SEQ ID NO 140
<211> LENGTH: 20
<212> TYPE: DNA
<213> ORGANISM: Homo sapiens

<400> SEQUENCE: 140
taaaattctg actactgaaa 20

<210> SEQ ID NO 141
<211> LENGTH: 20
<212> TYPE: DNA
<213> ORGANISM: Homo sapiens

<400> SEQUENCE: 141
ttgttgacag tgattttaga 20

<210> SEQ ID NO 142
<211> LENGTH: 20
<212> TYPE: DNA
<213> ORGANISM: Homo sapiens

<400> SEQUENCE: 142
taaaggaggg atacaactag 20

<210> SEQ ID NO 143
<211> LENGTH: 20
<212> TYPE: DNA
<213> ORGANISM: Homo sapiens

<400> SEQUENCE: 143
agtcagatgt ctgggtggtc 20

<210> SEQ ID NO 144
<211> LENGTH: 20
<212> TYPE: DNA
<213> ORGANISM: Homo sapiens

<400> SEQUENCE: 144
gtggcacaga gccattagtc 20

<210> SEQ ID NO 145
<211> LENGTH: 20
<212> TYPE: DNA
<213> ORGANISM: Homo sapiens

<400> SEQUENCE: 145
tcctaagggt taagatttga 20

<210> SEQ ID NO 146
<211> LENGTH: 20

-continued

<212> TYPE: DNA
<213> ORGANISM: Homo sapiens

<400> SEQUENCE: 146
tgaaacatct caacttccag 20

<210> SEQ ID NO 147
<211> LENGTH: 20
<212> TYPE: DNA
<213> ORGANISM: Homo sapiens

<400> SEQUENCE: 147
gagcagaaaa tttattcttt 20

<210> SEQ ID NO 148
<211> LENGTH: 20
<212> TYPE: DNA
<213> ORGANISM: Homo sapiens

<400> SEQUENCE: 148
tacacactaa actcatcgtg 20

<210> SEQ ID NO 149
<211> LENGTH: 20
<212> TYPE: DNA
<213> ORGANISM: Homo sapiens

<400> SEQUENCE: 149
catggattta ctgagggcag 20

<210> SEQ ID NO 150
<211> LENGTH: 20
<212> TYPE: DNA
<213> ORGANISM: Homo sapiens

<400> SEQUENCE: 150
ttattaacca tggatttact 20

<210> SEQ ID NO 151
<211> LENGTH: 20
<212> TYPE: DNA
<213> ORGANISM: Homo sapiens

<400> SEQUENCE: 151
ggtgtcgtac caccacctgg 20

<210> SEQ ID NO 152
<211> LENGTH: 20
<212> TYPE: DNA
<213> ORGANISM: Homo sapiens

<400> SEQUENCE: 152
aaagcctact aggttaatca 20

<210> SEQ ID NO 153
<211> LENGTH: 20
<212> TYPE: DNA
<213> ORGANISM: Homo sapiens

<400> SEQUENCE: 153
tggaaattaa ctccatagcc 20

<210> SEQ ID NO 154

<211> LENGTH: 20
<212> TYPE: DNA
<213> ORGANISM: Homo sapiens

<400> SEQUENCE: 154
agggatacaa ctagagtatg 20

<210> SEQ ID NO 155
<211> LENGTH: 4412
<212> TYPE: DNA
<213> ORGANISM: Mus musculus
<220> FEATURE:
<221> NAME/KEY: misc_feature
<222> LOCATION: 3140, 4337, 4399
<223> OTHER INFORMATION: n = A,T,C or G

<400> SEQUENCE: 155
tcagtagtgg aatgtgacca tgcacggaaa gaagtcagtg tacggactgc agggttgacg 60
gacaagacct ccaagaaaac atacacgttt gatatggtgt ttggagcatc tacaaaacaa 120
attgatgttt accgaagtgt tgtttgtcca attctagatg aagttattat gggctataat 180
tgcaccatct tcgcatatgg tcagactggc actggaaaaa cttttacaat ggaaggtgaa 240
aggtcaccta atgaagtata tacctgggag gaggatcctc tggctggtat aattccacgc 300
actcttcatc aaatttttga gaaacttact gataatggca ctgacttttc agttaaagtg 360
tccctattgg aaatctataa tgaggagctt tttgatcttc ttagtccatc ttctgatgtt 420
tctgaaaggc tgcagatgtt tgatgatccc cggaacaaga gaggagtgat aatcaaaggc 480
ttagaggaaa tcacagtaca caataaagat gaagtctacc aaatcttaga gaagggagca 540
gcaaaaagga caactgcagc aaccttgatg aatgcttact ctagtcgttc acactcagtt 600
ttttctgtta cgatacacat gaaacaaaca attgatggag aagagcttgt taaaattgga 660
aagttgaatt tggttgatct tgcaggaagt gaaaatattg ggcgttctgg agctgttgac 720
aagagggccc gggaagctgg aaatatcaac caatccctct tgactctggg aagagttatt 780
actgctcttg tggaaagaac acctcatatt ccttatcgag aatctaaact aactagaatc 840
ctgcaagatt ctcttggggg acgtacaaga acatctataa ttgcaaccat ttcccctgca 900
tctttcaatc ttgaggaaac tctgagtaca ttggaatatg ctcacagagc aaagaacata 960
atgaataagc ctgaagttaa tcaaaaactc accaaaaaag ctcttattaa ggagtataca 1020
gaagagatag agcgtttgaa gcgagatctt gcagcagctc gtgagaaaaa tggagtgtac 1080
atctctgaag aaagttttag agccatgaat ggaaaggtaa ctgttcagga ggaacaaatt 1140
gttgagttgg ttgaaaaaat cgctgttctt gaggaggagc tcagtaaggc tacagagtta 1200
tttatggata gtaagaacga acttgaccag tgtaaatctg acctgcaaac caagacacag 1260
gaacttgaaa ccactcagaa acatttgcaa gaaacaaaat tacaactggt taaagaggaa 1320
tatgtctctt cagccttgga aagaaccgag aagacactgc atgacacggc cagcaagttg 1380
cttaacacgg ttaaagaaac caccagggct gtatctggtc tacattctaa actggaccgc 1440
aagagagcaa tcgatgagca caacgctgaa gctcaggaga gctttggcaa aaacctcaac 1500
agtctgttta ataatatgga agaattgatt aaggatggca gtgcgaaaca aaaggccatg 1560
ctagacgttc ataagacact gtttggtaac ctgatgtctt gtagtgtctc tgcattagac 1620
accattacca cgacagcact tgaatctctc gtgtctattc cagaaaatgt gtccgctcgt 1680
gtttctcaga tttctgatat gatattggaa gagcaatcgt tagcagcaca aagtaaaagt 1740
gttctgcaag gattgattga tgaacttgtg accgaccttt tcacttccct gaagaccatc 1800

-continued

```
gtagccccta gtgtggtttc catcttgaac ataaataagc agctacagca tattttcagg   1860
gcttcatcga cagtggctga aaaggtagaa gatcaaaaaa gagaaataga cagttttctc   1920
agcatattgt gtaacaattt acatgaactc cgagaaaaca cagtttcttc cttggttgaa   1980
tcacaaaagc tttgtggaga cctaactgaa gacctgaaga caataaagga aacccattca   2040
caggaacttt gccagttaag cagtagttgg gcagagagat tctgtgcttt ggagaagaag   2100
tatgaaaaca tccagaaacc actgaacagt attcaagaaa atacagagcg gaggtctact   2160
gatataatca ataaaacaac agttcacagt aagagaaattc ttgctgaatc tgatggatta   2220
ttacaagaac tcagacactt taaccaagaa ggcacacagc tggttgaaga gtctgtagga   2280
cactgcagtt cactcaacag caacctggag actgtatccc aagagatcac ccagaagtgt   2340
gggaccctga acacaagcac agttcatttc tctgatcagt gggcatcctg cctaagcaag   2400
agaaaggaag aacttgagaa tttaatggag tttgtaaatg gctgttgtaa agcttcaagt   2460
tcggagatca ctaagaaagt aagagaacag agcgcacgtg ttgcgaacca gcacagctcc   2520
tttgttgctc agatgacttc cgatgaagaa agctgtaaag caggaagcct ggagcttgat   2580
aaaactataa agactgggtt aacaaagctg aattgctttc tgaaacagga tctgaaacta   2640
gatatcccaa caggtatgac accagagagg aaaaaatatt tatatccaac aacacttgtg   2700
agaactgaac cacgagagca gctccttgat cagctgcaaa agaaacaacc accaatgatg   2760
ctaaacagct cagaagccag caaggagacc agtcaggaca tggatgaaga gagggaggct   2820
ctggagcagt gtactgagga acttgtaagt ccagagacaa ctgaactacc cagtgcagat   2880
tgctcttcca gcagaggtct tccatttttc cagcgaaaaa agccacatgg aaaagacaaa   2940
gaaaacagag gccttaaccc ggtggagaag tataaagtgg aagaggcctc ggatctctcc   3000
atctccaaga gcagactgcc gcttcacacc tccataaacc tctagctgat ctgaggctta   3060
gggtgtcatc tttaaaatac aacctgaaac tccagagtct gaagctatgt acagatgaaa   3120
aggggactgc tgtgtgaggn cccacagtaa ctgtagttga actgaaagtc ttttttataa   3180
tccctgtagt ccaaggatgt agtaagctgg gtatcatttg ggatttacat tgaatatgtg   3240
tgtgtgtttc agctttttat ataaagaagc tcttctgtaa caagtaagta tttttcttgt   3300
atataattaa ataccaaata tatggaaatc attgttccag gtttagactt gtattggtga   3360
atgccatctc ctttgctgtc tggccaaggc tgtttcccta cctctaacca gccttttcta   3420
gtttgtcttc gactcctgtc tccctttttcc tgtcacttaa ccttttgtag cctacagaaa   3480
ggtttcttta gtatgagaaa cgcagggttt tacctggaac tcttctatct cactgattac   3540
ccttacaatc actgtcaaaa cacctgaccc tggaaggacc cttcttttgg gtccttcatt   3600
tgttctcgct gatatgcaca catctcattc cttctgaggt ctgacacatc accagcctcc   3660
ctgtagtgtc ggctcctaat gcaggagacc ttaaggcccc acttaaaagg tctttaagtc   3720
tcttagaaat gataagattg ttttcaaact accaattatg actataactt ctattttgtt   3780
tatcttttaa aactttattc cttgtatata ataaaaatgt atatatacat tccctctgtt   3840
gaaatattaa ccctcgctct ttcgctttga caacgctgtt tctggaagtt ggccatttta   3900
agatgaacca gagcacctac ctaaaagtgt atgcagagag taagtgtggt cacgtcaagt   3960
tcatgtatac ggttcagagt gatgtggttt tggcacagtc tcactatgga gctcaggctg   4020
gctttggact cactatgcag caggacagtc atccttccaa ggcctgggaa tacagacatc   4080
atcactgtgc ctgtttcaga aatagaactt tggccaggcg tggtggcgcc ctttaatccc   4140
```

-continued

```
agcactcggg aggcagaggc aggcggattt ctgatttcga ggccagcctg atctacaaag   4200

tgagtgccag gacagctagg gctacagaga aaccctgtct caaaaaaaca aaagaaatag   4260

aactttgtaa caaagagcta acccctaata gaaaattaga aaaaaatgct actttaagaa   4320

atttttttc ttgtacnttt ctccaactca ttgtagaaat agaaacgtta ttttaataaa   4380

aattaatgca taaattttnt cgaaaaaaaa aa                                 4412
```

<210> SEQ ID NO 156
<211> LENGTH: 612
<212> TYPE: DNA
<213> ORGANISM: Mus musculus

<400> SEQUENCE: 156

```
ggatttcgga gcagaggagg aggttcgtcc tgtccggctt ttgcggggcg gcggccacgg     60

ccaagaggcc tgcgtggacc tcggggacgc cgagctgcga gtctcggtcc tcgtggcctt    120

ggcagcaccg ggtgaggaga ggctgctccc ggttctcact gtgtctgagt ctccgctagg    180

ccggcaggtt ttggctcgac cgtcatggcg tcccagccga gttctttgaa gaagaaagag    240

gaaaagggca ggaacatcca ggtggtggtg agatgcagac catttaatct ggcagagcgg    300

aaagctaatg cccactcagt agtggaatgt gaccatgcac ggaaagaagt cagtgtacgg    360

actgcagggt tgacggacaa gacctccaag aaaacataca cgtttgatat ggtgtttgga    420

gcatctacaa aacaaattga tgtttaccga agtgttgttt gtccaattct agatgaagtt    480

attatgggct ataattgcac catctttcca tatggtcaga ctggcactgg aaaaactttt    540

acaatggaag gtgaaaggtc acctaatgaa gtttatacct gggaggaggg atcctctggc    600

tgggttaaat tc                                                        612
```

<210> SEQ ID NO 157
<211> LENGTH: 20
<212> TYPE: DNA
<213> ORGANISM: Mus musculus

<400> SEQUENCE: 157

```
tccgtacact gacttctttc                                                 20
```

<210> SEQ ID NO 158
<211> LENGTH: 20
<212> TYPE: DNA
<213> ORGANISM: Mus musculus

<400> SEQUENCE: 158

```
tgcagtccgt acactgactt                                                 20
```

<210> SEQ ID NO 159
<211> LENGTH: 20
<212> TYPE: DNA
<213> ORGANISM: Homo sapiens

<400> SEQUENCE: 159

```
gctccaaaca ccatatcaaa                                                 20
```

<210> SEQ ID NO 160
<211> LENGTH: 20
<212> TYPE: DNA
<213> ORGANISM: Homo sapiens

<400> SEQUENCE: 160

```
tagatgctcc aaacaccata                                                 20
```

<210> SEQ ID NO 161
<211> LENGTH: 20
<212> TYPE: DNA
<213> ORGANISM: Mus musculus

<400> SEQUENCE: 161
attttcactt cctgcaagat 20

<210> SEQ ID NO 162
<211> LENGTH: 20
<212> TYPE: DNA
<213> ORGANISM: Mus musculus

<400> SEQUENCE: 162
gttgatattt ccagcttccc 20

<210> SEQ ID NO 163
<211> LENGTH: 20
<212> TYPE: DNA
<213> ORGANISM: Mus musculus

<400> SEQUENCE: 163
tcaagaggga ttggttgata 20

<210> SEQ ID NO 164
<211> LENGTH: 20
<212> TYPE: DNA
<213> ORGANISM: Mus musculus

<400> SEQUENCE: 164
ataactcttc ccagagtcaa 20

<210> SEQ ID NO 165
<211> LENGTH: 20
<212> TYPE: DNA
<213> ORGANISM: Homo sapiens

<400> SEQUENCE: 165
tttagattct cgataaggaa 20

<210> SEQ ID NO 166
<211> LENGTH: 20
<212> TYPE: DNA
<213> ORGANISM: Homo sapiens

<400> SEQUENCE: 166
gttagtttag attctcgata 20

<210> SEQ ID NO 167
<211> LENGTH: 20
<212> TYPE: DNA
<213> ORGANISM: Homo sapiens

<400> SEQUENCE: 167
ggattctagt tagtttagat 20

<210> SEQ ID NO 168
<211> LENGTH: 20
<212> TYPE: DNA
<213> ORGANISM: Mus musculus

<400> SEQUENCE: 168
gagaatcttg caggattcta 20

<210> SEQ ID NO 169
<211> LENGTH: 20
<212> TYPE: DNA
<213> ORGANISM: Homo sapiens

<400> SEQUENCE: 169
attatagatg ttcttgtacg 20

<210> SEQ ID NO 170
<211> LENGTH: 20
<212> TYPE: DNA
<213> ORGANISM: Homo sapiens

<400> SEQUENCE: 170
gttgcaatta tagatgttct 20

<210> SEQ ID NO 171
<211> LENGTH: 20
<212> TYPE: DNA
<213> ORGANISM: Homo sapiens

<400> SEQUENCE: 171
cagagtttcc tcaagattga 20

<210> SEQ ID NO 172
<211> LENGTH: 20
<212> TYPE: DNA
<213> ORGANISM: Homo sapiens

<400> SEQUENCE: 172
gtactcagag tttcctcaag 20

<210> SEQ ID NO 173
<211> LENGTH: 20
<212> TYPE: DNA
<213> ORGANISM: Homo sapiens

<400> SEQUENCE: 173
ccaatgtact cagagtttcc 20

<210> SEQ ID NO 174
<211> LENGTH: 20
<212> TYPE: DNA
<213> ORGANISM: Homo sapiens

<400> SEQUENCE: 174
atattccaat gtactcagag 20

<210> SEQ ID NO 175
<211> LENGTH: 20
<212> TYPE: DNA
<213> ORGANISM: Homo sapiens

<400> SEQUENCE: 175
tgagcatatt ccaatgtact 20

<210> SEQ ID NO 176
<211> LENGTH: 20
<212> TYPE: DNA
<213> ORGANISM: Homo sapiens

<400> SEQUENCE: 176
ctccttaata agagcttttt 20

<210> SEQ ID NO 177
<211> LENGTH: 20
<212> TYPE: DNA
<213> ORGANISM: Homo sapiens

<400> SEQUENCE: 177
gtatactcct taataagagc 20

<210> SEQ ID NO 178
<211> LENGTH: 20
<212> TYPE: DNA
<213> ORGANISM: Mus musculus

<400> SEQUENCE: 178
caagatctcg cttcaaacgc 20

<210> SEQ ID NO 179
<211> LENGTH: 20
<212> TYPE: DNA
<213> ORGANISM: Homo sapiens

<400> SEQUENCE: 179
tacactccat ttttctcacg 20

<210> SEQ ID NO 180
<211> LENGTH: 20
<212> TYPE: DNA
<213> ORGANISM: Mus musculus

<400> SEQUENCE: 180
attcatggct ctaaaacttt 20

<210> SEQ ID NO 181
<211> LENGTH: 20
<212> TYPE: DNA
<213> ORGANISM: Mus musculus

<400> SEQUENCE: 181
ctcctcctca agaacagcga 20

<210> SEQ ID NO 182
<211> LENGTH: 20
<212> TYPE: DNA
<213> ORGANISM: Mus musculus

<400> SEQUENCE: 182
agttcgttct tactatccat 20

<210> SEQ ID NO 183
<211> LENGTH: 20
<212> TYPE: DNA
<213> ORGANISM: Homo sapiens

<400> SEQUENCE: 183
gatttacact ggtcaagttc 20

<210> SEQ ID NO 184
<211> LENGTH: 20
<212> TYPE: DNA
<213> ORGANISM: Homo sapiens -continued

<400> SEQUENCE: 184
ggtcagattt acactggtca 20

<210> SEQ ID NO 185
<211> LENGTH: 20
<212> TYPE: DNA
<213> ORGANISM: Homo sapiens

<400> SEQUENCE: 185
ttgcaggtca gatttacact 20

<210> SEQ ID NO 186
<211> LENGTH: 20
<212> TYPE: DNA
<213> ORGANISM: Mus musculus

<400> SEQUENCE: 186
tgtttctgag tggtttcaag 20

<210> SEQ ID NO 187
<211> LENGTH: 20
<212> TYPE: DNA
<213> ORGANISM: Mus musculus

<400> SEQUENCE: 187
tccaaggctg aagagacata 20

<210> SEQ ID NO 188
<211> LENGTH: 20
<212> TYPE: DNA
<213> ORGANISM: Mus musculus

<400> SEQUENCE: 188
tcggttcttt ccaaggctga 20

<210> SEQ ID NO 189
<211> LENGTH: 20
<212> TYPE: DNA
<213> ORGANISM: Mus musculus

<400> SEQUENCE: 189
tgctggccgt gtcatgcagt 20

<210> SEQ ID NO 190
<211> LENGTH: 20
<212> TYPE: DNA
<213> ORGANISM: Mus musculus

<400> SEQUENCE: 190
ttctttaacc gtgttaagca 20

<210> SEQ ID NO 191
<211> LENGTH: 20
<212> TYPE: DNA
<213> ORGANISM: Mus musculus

<400> SEQUENCE: 191
atcaatcaat ccttgcagaa 20

<210> SEQ ID NO 192
<211> LENGTH: 20
<212> TYPE: DNA
<213> ORGANISM: Mus musculus

<400> SEQUENCE: 192
tatttatgtt caagatggaa 20

<210> SEQ ID NO 193
<211> LENGTH: 20
<212> TYPE: DNA
<213> ORGANISM: Mus musculus

<400> SEQUENCE: 193
aagaaactgt gttttctcgg 20

<210> SEQ ID NO 194
<211> LENGTH: 20
<212> TYPE: DNA
<213> ORGANISM: Mus musculus

<400> SEQUENCE: 194
agcttttgtg attcaaccaa 20

<210> SEQ ID NO 195
<211> LENGTH: 20
<212> TYPE: DNA
<213> ORGANISM: Mus musculus

<400> SEQUENCE: 195
catacttctt ctccaaagca 20

<210> SEQ ID NO 196
<211> LENGTH: 20
<212> TYPE: DNA
<213> ORGANISM: Mus musculus

<400> SEQUENCE: 196
tagacctccg ctctgtattt 20

<210> SEQ ID NO 197
<211> LENGTH: 20
<212> TYPE: DNA
<213> ORGANISM: Mus musculus

<400> SEQUENCE: 197
cttgtaataa tccatcagat 20

<210> SEQ ID NO 198
<211> LENGTH: 20
<212> TYPE: DNA
<213> ORGANISM: Mus musculus

<400> SEQUENCE: 198
ttaaagtgtc tgagttcttg 20

<210> SEQ ID NO 199
<211> LENGTH: 20
<212> TYPE: DNA
<213> ORGANISM: Mus musculus

<400> SEQUENCE: 199
caggttgctg ttgagtgaac 20

<210> SEQ ID NO 200
<211> LENGTH: 20
<212> TYPE: DNA

-continued

<213> ORGANISM: Mus musculus

<400> SEQUENCE: 200
cagtctccag gttgctgttg 20

<210> SEQ ID NO 201
<211> LENGTH: 20
<212> TYPE: DNA
<213> ORGANISM: Mus musculus

<400> SEQUENCE: 201
aggcaggatg cccactgatc 20

<210> SEQ ID NO 202
<211> LENGTH: 20
<212> TYPE: DNA
<213> ORGANISM: Mus musculus

<400> SEQUENCE: 202
actccattaa attctcaagt 20

<210> SEQ ID NO 203
<211> LENGTH: 20
<212> TYPE: DNA
<213> ORGANISM: Mus musculus

<400> SEQUENCE: 203
caacacgtgc gctctgttct 20

<210> SEQ ID NO 204
<211> LENGTH: 20
<212> TYPE: DNA
<213> ORGANISM: Mus musculus

<400> SEQUENCE: 204
tgtgctggtt cgcaacacgt 20

<210> SEQ ID NO 205
<211> LENGTH: 20
<212> TYPE: DNA
<213> ORGANISM: Mus musculus

<400> SEQUENCE: 205
aagcaattca gctttgttaa 20

<210> SEQ ID NO 206
<211> LENGTH: 20
<212> TYPE: DNA
<213> ORGANISM: Mus musculus

<400> SEQUENCE: 206
tttcagaaag caattcagct 20

<210> SEQ ID NO 207
<211> LENGTH: 20
<212> TYPE: DNA
<213> ORGANISM: Mus musculus

<400> SEQUENCE: 207
gtgtcatacc tgttgggata 20

<210> SEQ ID NO 208
<211> LENGTH: 20

<212> TYPE: DNA
<213> ORGANISM: Mus musculus

<400> SEQUENCE: 208
tcctctctgg tgtcatacct 20

<210> SEQ ID NO 209
<211> LENGTH: 20
<212> TYPE: DNA
<213> ORGANISM: Mus musculus

<400> SEQUENCE: 209
ctcacaagtg ttgttggata 20

<210> SEQ ID NO 210
<211> LENGTH: 20
<212> TYPE: DNA
<213> ORGANISM: Mus musculus

<400> SEQUENCE: 210
ctgagctgtt tagcatcatt 20

<210> SEQ ID NO 211
<211> LENGTH: 20
<212> TYPE: DNA
<213> ORGANISM: Mus musculus

<400> SEQUENCE: 211
tgtctctgga cttacaagtt 20

<210> SEQ ID NO 212
<211> LENGTH: 20
<212> TYPE: DNA
<213> ORGANISM: Mus musculus

<400> SEQUENCE: 212
gggtagttca gttgtctctg 20

<210> SEQ ID NO 213
<211> LENGTH: 20
<212> TYPE: DNA
<213> ORGANISM: Mus musculus

<400> SEQUENCE: 213
aaatggaaga cctctgctgg 20

<210> SEQ ID NO 214
<211> LENGTH: 20
<212> TYPE: DNA
<213> ORGANISM: Mus musculus

<400> SEQUENCE: 214
gctggaaaaa tggaagacct 20

<210> SEQ ID NO 215
<211> LENGTH: 20
<212> TYPE: DNA
<213> ORGANISM: Mus musculus

<400> SEQUENCE: 215
ctcagatcag ctagaggttt 20

<210> SEQ ID NO 216

<211> LENGTH: 20
<212> TYPE: DNA
<213> ORGANISM: Mus musculus

<400> SEQUENCE: 216
taagcctcag atcagctaga 20

<210> SEQ ID NO 217
<211> LENGTH: 20
<212> TYPE: DNA
<213> ORGANISM: Mus musculus

<400> SEQUENCE: 217
gttgtatttt aaagatgaca 20

<210> SEQ ID NO 218
<211> LENGTH: 20
<212> TYPE: DNA
<213> ORGANISM: Mus musculus

<400> SEQUENCE: 218
agactttcag ttcaactaca 20

<210> SEQ ID NO 219
<211> LENGTH: 20
<212> TYPE: DNA
<213> ORGANISM: Mus musculus

<400> SEQUENCE: 219
acacacacac atattcaatg 20

<210> SEQ ID NO 220
<211> LENGTH: 20
<212> TYPE: DNA
<213> ORGANISM: Mus musculus

<400> SEQUENCE: 220
atacttactt gttacagaag 20

<210> SEQ ID NO 221
<211> LENGTH: 20
<212> TYPE: DNA
<213> ORGANISM: Mus musculus

<400> SEQUENCE: 221
aaaagggaga caggagtcga 20

<210> SEQ ID NO 222
<211> LENGTH: 20
<212> TYPE: DNA
<213> ORGANISM: Mus musculus

<400> SEQUENCE: 222
ttccaggtaa aaccctgcgt 20

<210> SEQ ID NO 223
<211> LENGTH: 20
<212> TYPE: DNA
<213> ORGANISM: Mus musculus

<400> SEQUENCE: 223
agacttaaag accttttaag 20

<210> SEQ ID NO 224
<211> LENGTH: 20
<212> TYPE: DNA
<213> ORGANISM: Mus musculus

<400> SEQUENCE: 224
ctctctgcat acacttttag 20

<210> SEQ ID NO 225
<211> LENGTH: 20
<212> TYPE: DNA
<213> ORGANISM: Mus musculus

<400> SEQUENCE: 225
ctgtgccaaa accacatcac 20

<210> SEQ ID NO 226
<211> LENGTH: 20
<212> TYPE: DNA
<213> ORGANISM: Mus musculus

<400> SEQUENCE: 226
tagtgagtcc aaagccagcc 20

<210> SEQ ID NO 227
<211> LENGTH: 20
<212> TYPE: DNA
<213> ORGANISM: Mus musculus

<400> SEQUENCE: 227
ggatgactgt cctgctgcat 20

<210> SEQ ID NO 228
<211> LENGTH: 20
<212> TYPE: DNA
<213> ORGANISM: Mus musculus

<400> SEQUENCE: 228
gtctgtattc ccaggccttg 20

<210> SEQ ID NO 229
<211> LENGTH: 20
<212> TYPE: DNA
<213> ORGANISM: Mus musculus

<400> SEQUENCE: 229
agatcaggct ggcctcgaaa 20

<210> SEQ ID NO 230
<211> LENGTH: 20
<212> TYPE: DNA
<213> ORGANISM: Mus musculus

<400> SEQUENCE: 230
ctctttgtta caaagttcta 20

<210> SEQ ID NO 231
<211> LENGTH: 20
<212> TYPE: DNA
<213> ORGANISM: Mus musculus

<400> SEQUENCE: 231
taatttttat taaaataacg 20

```
<210> SEQ ID NO 232
<211> LENGTH: 20
<212> TYPE: DNA
<213> ORGANISM: Mus musculus

<400> SEQUENCE: 232

tcctctttct tcttcaaaga                                                  20


<210> SEQ ID NO 233
<211> LENGTH: 20
<212> TYPE: DNA
<213> ORGANISM: Homo sapiens

<400> SEQUENCE: 233

atctcaccac cacctggatg                                                  20


<210> SEQ ID NO 234
<211> LENGTH: 20
<212> TYPE: DNA
<213> ORGANISM: Mus musculus

<400> SEQUENCE: 234

actgagtggg cattagcttt                                                  20


<210> SEQ ID NO 235
<211> LENGTH: 25
<212> TYPE: DNA
<213> ORGANISM: Artificial Sequence
<220> FEATURE:
<223> OTHER INFORMATION: Primer

<400> SEQUENCE: 235

gcttcaagtt cggagatcac taaga                                            25


<210> SEQ ID NO 236
<211> LENGTH: 22
<212> TYPE: DNA
<213> ORGANISM: Artificial Sequence
<220> FEATURE:
<223> OTHER INFORMATION: Primer

<400> SEQUENCE: 236

cggaagtcat ctgagcaaca aa                                               22


<210> SEQ ID NO 237
<211> LENGTH: 23
<212> TYPE: DNA
<213> ORGANISM: Artificial Sequence
<220> FEATURE:
<223> OTHER INFORMATION: Probe

<400> SEQUENCE: 237

agaacagagc gcacgtgttg cga                                              23


<210> SEQ ID NO 238
<211> LENGTH: 19
<212> TYPE: RNA
<213> ORGANISM: Artificial Sequence
<220> FEATURE:
<223> OTHER INFORMATION: Antisense compound

<400> SEQUENCE: 238

cgagaggcgg acgggaccg                                                   19
```

-continued

<210> SEQ ID NO 239
<211> LENGTH: 21
<212> TYPE: DNA
<213> ORGANISM: Artificial Sequence
<220> FEATURE:
<223> OTHER INFORMATION: Antisense compound
<220> FEATURE:
<221> NAME/KEY: misc_feature
<222> LOCATION: (1)...(19)
<223> OTHER INFORMATION: bases at these positions are RNA

<400> SEQUENCE: 239
cgagaggcgg acgggaccgt t 21

<210> SEQ ID NO 240
<211> LENGTH: 21
<212> TYPE: DNA
<213> ORGANISM: Artificial Sequence
<220> FEATURE:
<223> OTHER INFORMATION: Antisense compound
<220> FEATURE:
<221> NAME/KEY: misc_feature
<222> LOCATION: (3)...(21)
<223> OTHER INFORMATION: bases at these positions are RNA

<400> SEQUENCE: 240
ttgcucuccg ccugcccugg c 21

<210> SEQ ID NO 241
<211> LENGTH: 19
<212> TYPE: RNA
<213> ORGANISM: Artificial Sequence
<220> FEATURE:
<223> OTHER INFORMATION: Antisense compound

<400> SEQUENCE: 241
gcucuccgcc ugcccuggc 19